US009393430B2

(12) United States Patent
Demers et al.

(10) Patent No.: US 9,393,430 B2
(45) Date of Patent: Jul. 19, 2016

(54) METHODS AND APPARATUSES FOR CONTROL OF A WEARABLE TRANSDERMAL NEUROSTIMULATOR TO APPLY ENSEMBLE WAVEFORMS

(71) Applicant: Thync Global, Inc., Los Gatos, CA (US)

(72) Inventors: Remi Demers, Saint-Nicolas (CA); Sumon K. Pal, Boston, MA (US); Jonathan Charlesworth, Boston, MA (US); Jay Frederick Hamlin, Santa Cruz, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

(21) Appl. No.: 14/715,483

(22) Filed: May 18, 2015

(65) Prior Publication Data

US 2015/0328467 A1 Nov. 19, 2015

Related U.S. Application Data

(60) Provisional application No. 61/994,860, filed on May 17, 2014, provisional application No. 62/100,029, filed on Jan. 5, 2015.

(51) Int. Cl.
*A61N 1/372* (2006.01)
*A61N 1/36* (2006.01)

(52) U.S. Cl.
CPC .......... *A61N 1/3727* (2013.01); *A61N 1/36025* (2013.01); *A61N 1/36082* (2013.01); *A61N 1/37217* (2013.01)

(58) Field of Classification Search
CPC ............ A61N 1/37252; A61N 1/3727; A61N 1/36025; A61N 1/37217; A61N 1/36082
See application file for complete search history.

(56) References Cited

U.S. PATENT DOCUMENTS 4,431,000 A    2/1984   Butler et al.
4,646,744 A    3/1987   Capel
(Continued)

FOREIGN PATENT DOCUMENTS

EP    502919 B1    11/1993
EP    801957 A1    10/1997
(Continued)

OTHER PUBLICATIONS

Tyler et al.; U.S. Appl. No. 14/826,776 entitled "Transcranial ultrasound systems," filed Aug. 14, 2015.
(Continued)

*Primary Examiner* — Rex R Holmes
(74) *Attorney, Agent, or Firm* — Shay Glenn LLP

(57) ABSTRACT

Methods and apparatuses for controlling a wearable neurostimulator from a control apparatus. Described herein are methods and apparatuses for controlling the application of ensemble waveforms using a transdermal electrical stimulation by a neurostimulator having a processor. The controller may provide specifically configured commands to efficiently and accurately control the delivery of an ensemble waveform by the neurostimulator, wherein the ensemble waveform includes a sequence of component biphasic current waveforms in which one or more parameters (such as frequency, current amplitude, percent duty cycle, and percent charge imbalance) vary between sequential component waveforms particularly effective at evoking a desired cognitive state by TES.

29 Claims, 25 Drawing Sheets

(56) References Cited

U.S. PATENT DOCUMENTS

| | | | |
|---|---|---|---|
| 4,664,117 A | 5/1987 | Beck | |
| 5,144,952 A | 9/1992 | Frachet et al. | |
| 5,183,041 A | 2/1993 | Toriu et al. | |
| 5,342,410 A | 8/1994 | Braverman | |
| 5,397,338 A | 3/1995 | Grey et al. | |
| 5,476,481 A | 12/1995 | Schondorf | |
| 5,487,759 A | 1/1996 | Bastyr et al. | |
| 5,514,175 A | 5/1996 | Kim et al. | |
| 5,540,736 A | 7/1996 | Haimovich et al. | |
| 5,573,552 A | 11/1996 | Hansjurgens | |
| 5,578,065 A | 11/1996 | Hattori et al. | |
| 5,593,427 A | 1/1997 | Gliner et al. | |
| 6,066,163 A | 5/2000 | John | |
| 6,324,432 B1 | 11/2001 | Rigaux et al. | |
| 6,445,955 B1 | 9/2002 | Michelson et al. | |
| 6,463,328 B1 | 10/2002 | John | |
| 6,526,318 B1 | 2/2003 | Ansarinia | |
| 6,567,702 B1 | 5/2003 | Nekhendzy et al. | |
| 6,623,430 B1 | 9/2003 | Slayton et al. | |
| 6,731,987 B1 | 5/2004 | McAdams et al. | |
| 6,983,184 B2 | 1/2006 | Price | |
| 7,120,499 B2 | 10/2006 | Thrope et al. | |
| 7,146,217 B2 | 12/2006 | Firlik et al. | |
| 7,376,467 B2 | 5/2008 | Thrope et al. | |
| 7,422,555 B2 | 9/2008 | Zabara | |
| 7,577,481 B2 | 8/2009 | Firlik et al. | |
| 7,660,636 B2 | 2/2010 | Castel et al. | |
| 7,891,615 B2 | 2/2011 | Bevirt | |
| 7,949,403 B2 | 5/2011 | Palermo et al. | |
| 8,086,318 B2 | 12/2011 | Strother et al. | |
| 8,097,926 B2 | 1/2012 | De Graff et al. | |
| 8,121,695 B2 | 2/2012 | Gliner et al. | |
| 8,150,537 B2 | 4/2012 | Tanaka et al. | |
| 8,190,248 B2 | 5/2012 | Besio et al. | |
| 8,204,601 B2 | 6/2012 | Moyer et al. | |
| 8,239,030 B1 | 8/2012 | Hagedorn et al. | |
| 8,265,761 B2 | 9/2012 | Siever | |
| 8,280,502 B2 | 10/2012 | Hargrove et al. | |
| 8,380,315 B2 | 2/2013 | DeGiorgio et al. | |
| 8,428,738 B2 | 4/2013 | Valencia | |
| 8,494,627 B2 | 7/2013 | Bikson et al. | |
| 8,506,469 B2 | 8/2013 | Dietrich et al. | |
| 8,560,075 B2 | 10/2013 | Covalin | |
| 8,639,343 B2 | 1/2014 | De Vos | |
| 8,688,239 B2 | 4/2014 | Hartlep et al. | |
| 8,843,210 B2 | 9/2014 | Simon et al. | |
| 8,903,494 B2 | 12/2014 | Goldwasser et al. | |
| 9,002,458 B2 | 4/2015 | Pal et al. | |
| 9,014,811 B2 | 4/2015 | Pal et al. | |
| 2002/0116036 A1 | 8/2002 | Daignault et al. | |
| 2003/0225323 A1 | 12/2003 | Kiani et al. | |
| 2004/0098065 A1 | 5/2004 | Hagglof et al. | |
| 2004/0267333 A1 | 12/2004 | Kronberg | |
| 2005/0165460 A1 | 7/2005 | Erfan | |
| 2005/0267388 A1 | 12/2005 | Hanna | |
| 2006/0064139 A1 | 3/2006 | Chung et al. | |
| 2007/0088419 A1 | 4/2007 | Fiorina et al. | |
| 2007/0173890 A1 | 7/2007 | Armstrong | |
| 2007/0213790 A1 | 9/2007 | Nolan et al. | |
| 2007/0276451 A1 | 11/2007 | Rigaux | |
| 2008/0045882 A1 | 2/2008 | Finsterwald | |
| 2008/0132974 A1 | 6/2008 | Strother et al. | |
| 2008/0208266 A1 | 8/2008 | Lesser et al. | |
| 2008/0215113 A1 | 9/2008 | Pawlowicz | |
| 2008/0275293 A1 | 11/2008 | Lattner et al. | |
| 2008/0281368 A1 | 11/2008 | Bulkes et al. | |
| 2008/0319505 A1 | 12/2008 | Boyden et al. | |
| 2009/0048642 A1 | 2/2009 | Goroszeniuk | |
| 2009/0099623 A1 | 4/2009 | Bentwich | |
| 2009/0112280 A1 | 4/2009 | Wingeier et al. | |
| 2009/0177243 A1 | 7/2009 | Lebedev et al. | |
| 2009/0210028 A1 | 8/2009 | Rigaux et al. | |
| 2009/0240303 A1 | 9/2009 | Wahlstrand et al. | |
| 2009/0270947 A1 | 10/2009 | Stone et al. | |
| 2009/0287108 A1 | 11/2009 | Levy | |
| 2010/0057154 A1 | 3/2010 | Dietrich et al. | |
| 2010/0145399 A1 | 6/2010 | Johari et al. | |
| 2010/0152817 A1 | 6/2010 | Gillbe | |
| 2010/0256436 A1 | 10/2010 | Partsch et al. | |
| 2011/0082326 A1 | 4/2011 | Mishelevich et al. | |
| 2011/0082515 A1 | 4/2011 | Libbus et al. | |
| 2011/0093033 A1 | 4/2011 | Nekhendzy | |
| 2011/0112394 A1 | 5/2011 | Mishelevich | |
| 2011/0114191 A1 | 5/2011 | Wheater et al. | |
| 2011/0137381 A1 | 6/2011 | Lee et al. | |
| 2011/0144716 A1 | 6/2011 | Bikson et al. | |
| 2011/0160811 A1 | 6/2011 | Walker | |
| 2011/0190846 A1 | 8/2011 | Ruffini et al. | |
| 2011/0230701 A1 | 9/2011 | Simon et al. | |
| 2011/0230702 A1 | 9/2011 | Honour | |
| 2011/0230938 A1 | 9/2011 | Simon et al. | |
| 2011/0270345 A1 | 11/2011 | Johnston et al. | |
| 2011/0276112 A1 | 11/2011 | Simon et al. | |
| 2011/0288610 A1 | 11/2011 | Brocke | |
| 2011/0319950 A1 | 12/2011 | Sullivan | |
| 2012/0016431 A1 | 1/2012 | Paul et al. | |
| 2012/0029591 A1 | 2/2012 | Simon et al. | |
| 2012/0029601 A1 | 2/2012 | Simon et al. | |
| 2012/0101366 A1 | 4/2012 | Ruohonen et al. | |
| 2012/0109251 A1 | 5/2012 | Lebedev et al. | |
| 2012/0149973 A1 | 6/2012 | Holloway | |
| 2012/0165759 A1 | 6/2012 | Rogers et al. | |
| 2012/0185020 A1 | 7/2012 | Simon et al. | |
| 2012/0209346 A1 | 8/2012 | Bikson et al. | |
| 2012/0245653 A1 | 9/2012 | Bikson et al. | |
| 2012/0302912 A1 | 11/2012 | Moffitt et al. | |
| 2013/0035734 A1 | 2/2013 | Soler et al. | |
| 2013/0041235 A1 | 2/2013 | Rogers et al. | |
| 2013/0060304 A1 | 3/2013 | La Tendresse et al. | |
| 2013/0066395 A1 | 3/2013 | Simon et al. | |
| 2013/0079659 A1 | 3/2013 | Akhadov et al. | |
| 2013/0158627 A1 | 6/2013 | Gozani et al. | |
| 2013/0184779 A1 | 7/2013 | Bikson et al. | |
| 2013/0204315 A1 | 8/2013 | Wongsarnpigoon et al. | |
| 2013/0226275 A1 | 8/2013 | Duncan | |
| 2013/0267761 A1 | 10/2013 | Bentwich | |
| 2013/0282095 A1 | 10/2013 | Mignolet et al. | |
| 2013/0318168 A1 | 11/2013 | Demain et al. | |
| 2013/0325096 A1 | 12/2013 | Dupelle et al. | |
| 2014/0031895 A1 | 1/2014 | Rahimi et al. | |
| 2014/0277324 A1 | 9/2014 | DiUbaldi et al. | |
| 2014/0336728 A1 | 11/2014 | Franke et al. | |
| 2015/0088224 A1 | 3/2015 | Goldwasser et al. | |
| 2015/0174403 A1 | 6/2015 | Pal et al. | |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 10-108913 A | 4/1998 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2009-85901 A | 4/2009 |
| JP | 2011-118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |

(56) References Cited

FOREIGN PATENT DOCUMENTS

| WO | WO2009/147599 A1 | 12/2009 |
|---|---|---|
| WO | WO2010/047834 A1 | 4/2010 |
| WO | WO2010/067145 A1 | 6/2010 |
| WO | WO2011/147546 A1 | 12/2011 |
| WO | WO2012/082960 A2 | 6/2012 |
| WO | WO2012/089588 A1 | 7/2012 |
| WO | WO 2012/116407 A1 | 9/2012 |
| WO | WO2012/129574 A2 | 9/2012 |
| WO | WO2012/150600 A2 | 11/2012 |
| WO | WO2012/156052 A2 | 11/2012 |
| WO | WO2013/071307 A1 | 5/2013 |

OTHER PUBLICATIONS

Pal et al.; U.S. Appl. No. 14/634,551 entitled "Methods for user control of neurostimulation to modify a cognitive state," filed Feb. 27, 2015.

Jeffery et al.; U.S. Appl. No. 14/634,664 entitled; "Cantilever electrodes for transdermal and transcranial stimulation," filed Feb. 27, 2015.

Jeffery et al.; U.S. Appl. No. 14/634,661 entitled "Methods for attaching and wearing a neurostimulator," filed Feb. 27, 2015.

Goldwasser et al.; U.S. Appl. No. 14/715,461 entitled "Wearable transdermal neurostimulator having cantilevered attachment," filed May 18, 2015.

Charlesworth et al.; U.S. Appl. No. 14/715,476 entitled "Methods and apparatuses for amplitude-modulated ensemble waveforms for neurostimulation," filed May 18, 2015.

Demers et al.; U.S. Appl. No. 14/715,470 entitled "Transdermal neurostimulator adapted to reduce capacitive build-up," filed May 18, 2015.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Chaieb et al.; Transcranial alternating current stimulation in the low kHz range increases motor cortex excitability; Restor Neurol Neurosci; 29(3); pp. 167-175; Mar. 2011.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feburary 2011.

GoFLOW; tDCS Kit; product information; 9 pgs . . . ; printed Feb. 10, 2014 (http://flowstateengaged.com/).

Gracenote; Timeline-metadata-api; 3 pages; retrieved from the internet Jul. 7, 2015; (https://github.com/gracenote/timeline-metadata-api/blob/master/README.md).

Grindhouse Wetware; Thinking Cap; product information; 1 pg.; printed Feb. 10, 2014 (http://www.grindhousewetware.com/thinkingcap.html).

Kanai et al.; Frequency-dependent electrical stimulatioin of the visual cortex; Curr. Biol.; 18(23); pp. 1839-1843; Dec. 9, 2008.

Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.

Rossini et al.; Non-invasive electrical and magnetic stimulation of the brain, spinal cord and roots: basic principles and procedures for routine clinical application; Electroenceph. Clin. Neurophysiol.; 91(2); pp. 79-92; Aug. 1994.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

STD Pharmaceutical Products; Idrostar intophoresis machine (product and use information); 9 pgs.; Dec. 2011 (printed Feb. 11, 2014 from http://www.iontophoresis.info/instructions/).

Terney et al.; Increasing human brain excitability by transcranial high-frequency random noise stimulation; The Journal of Neuroscience; 28(52); pp. 14127-14155; Dec. 2008.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filed and any foreign priority date).

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 61/550,334 entitled "Improvement of Direct Communication," filed Oct. 21, 2011.

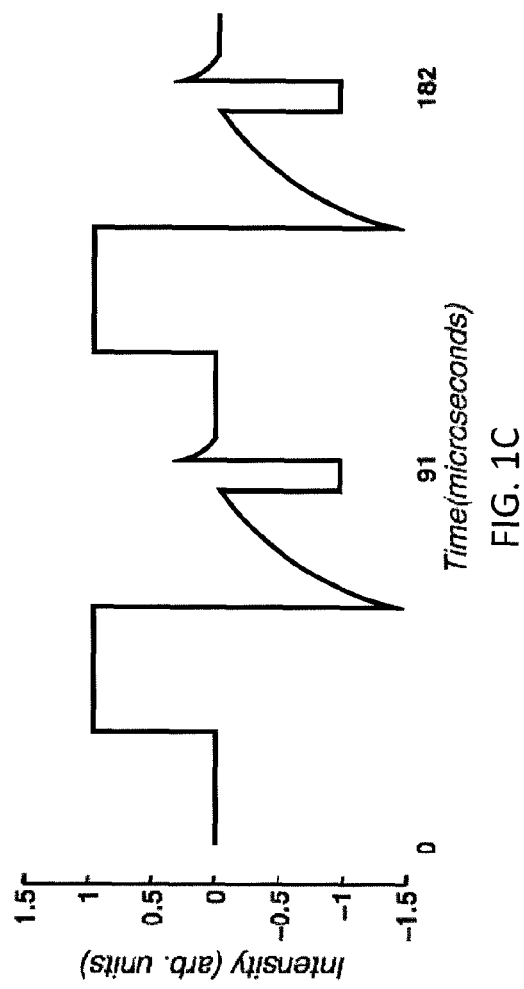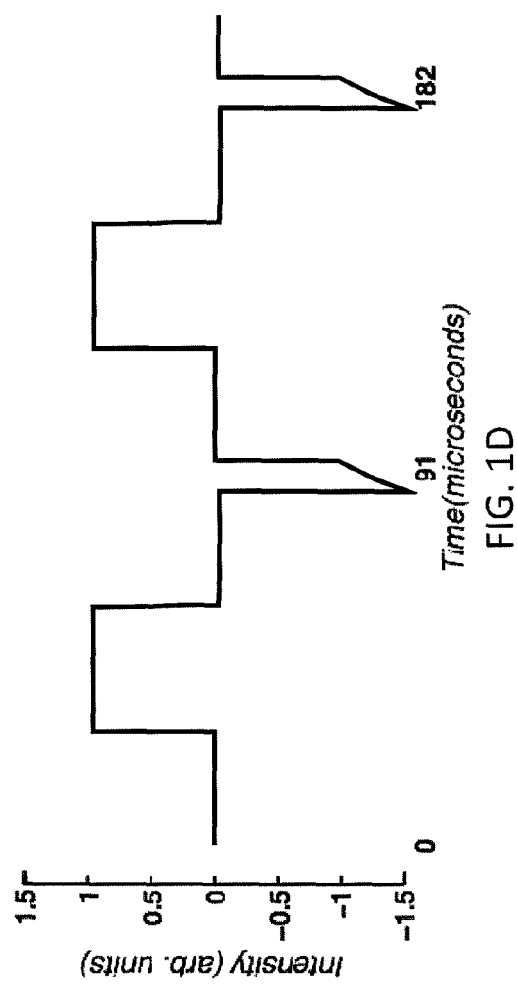

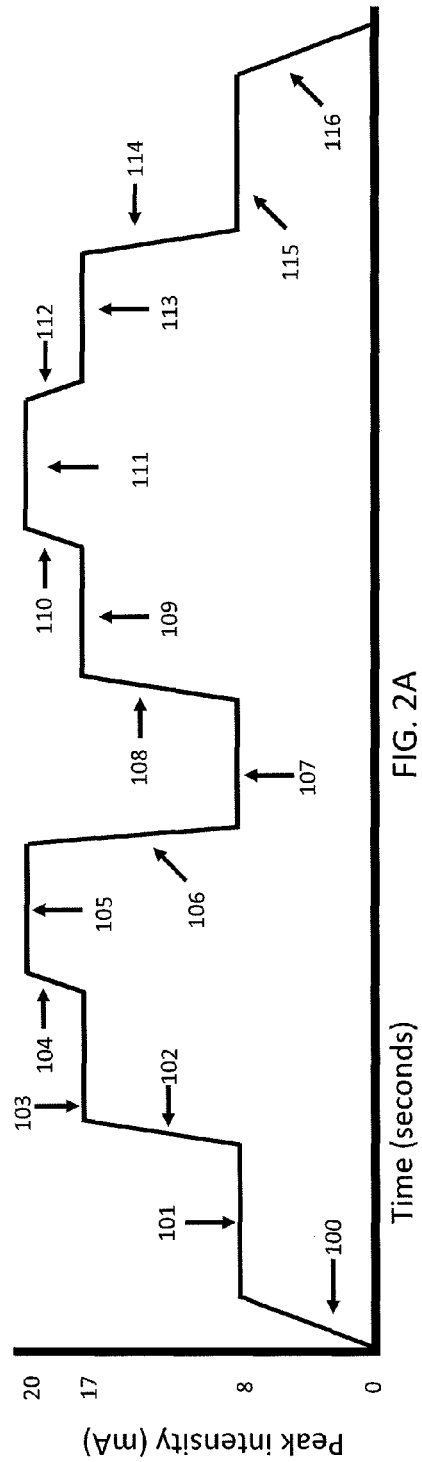
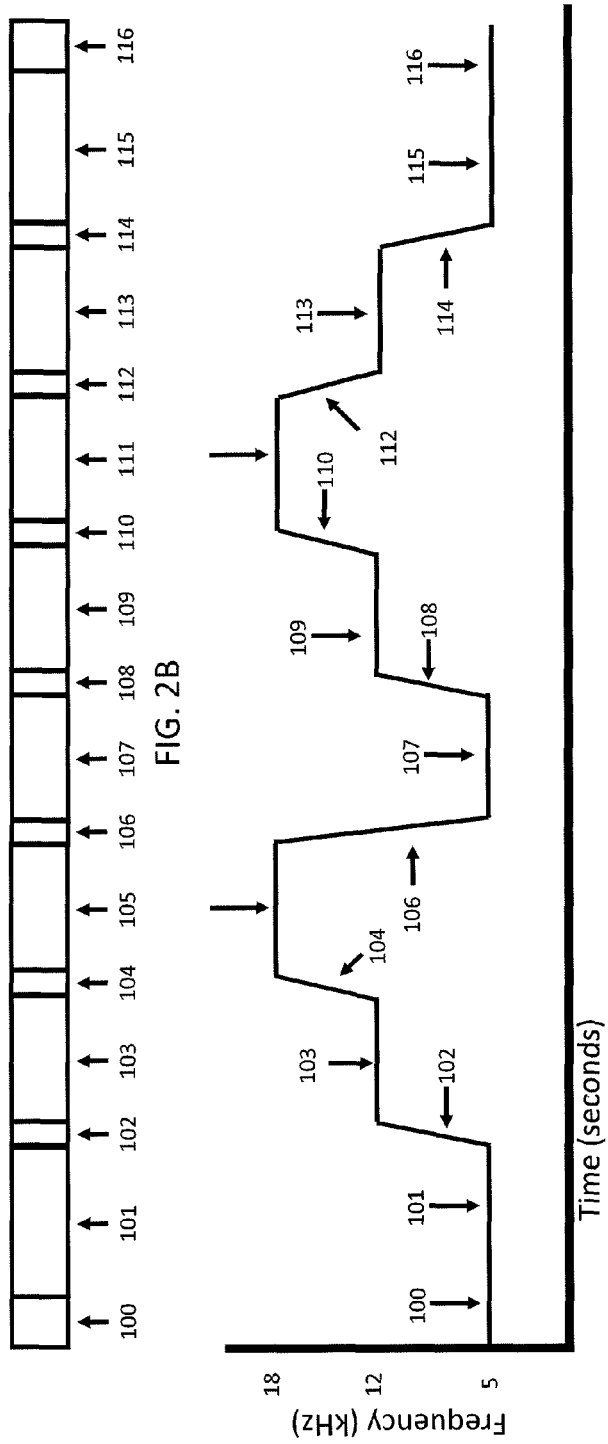
FIG. 2A
FIG. 2B
FIG. 2C

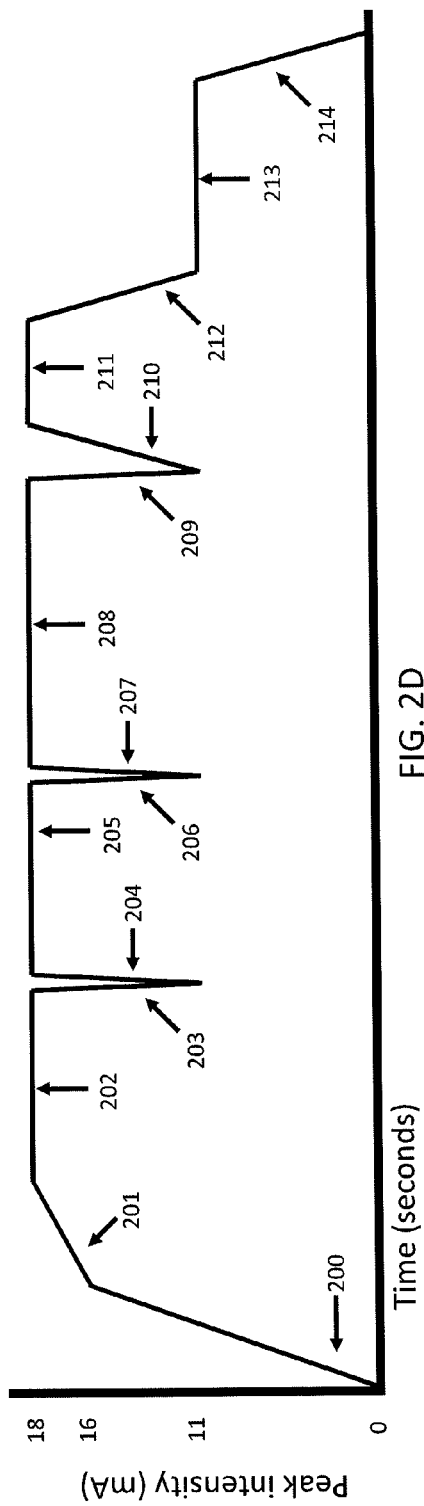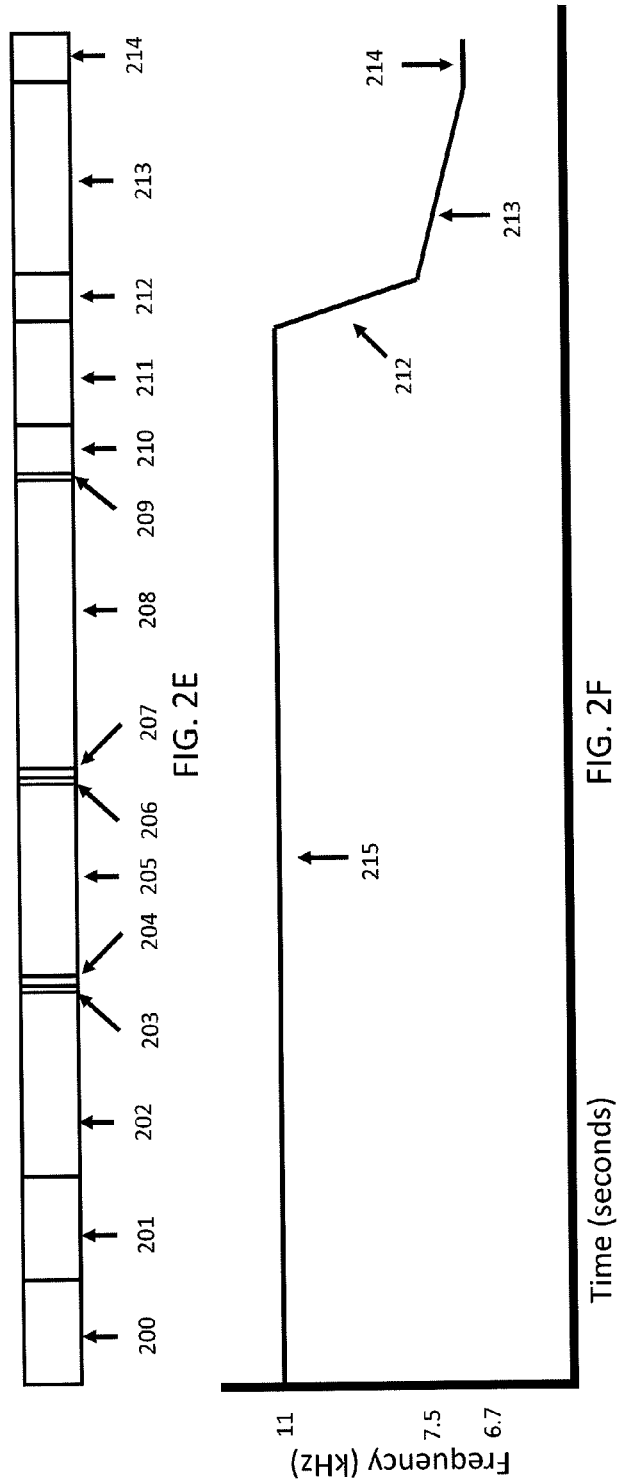
FIG. 2D
FIG. 2E
FIG. 2F

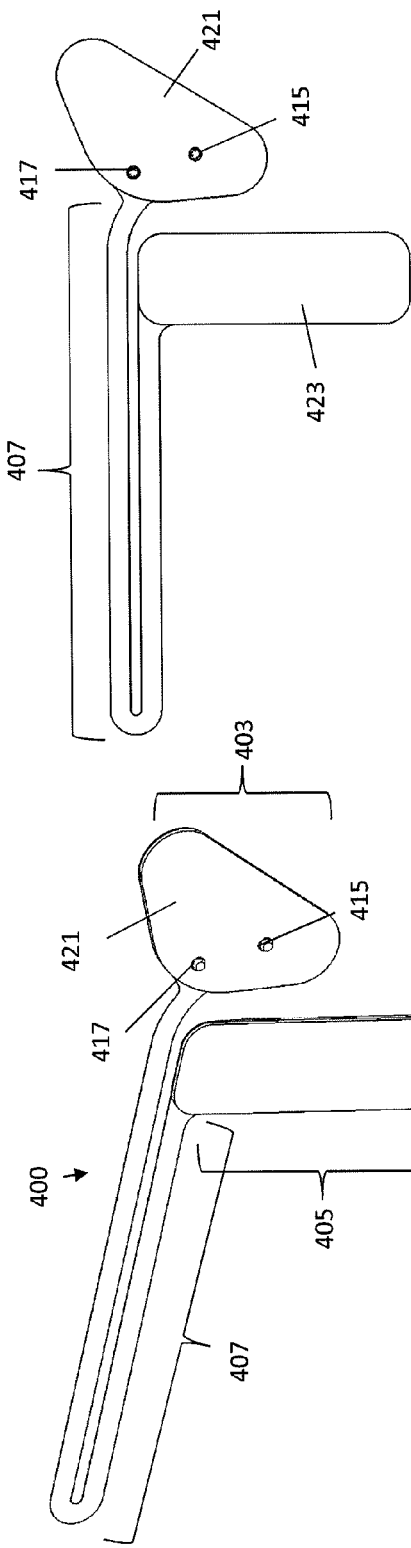
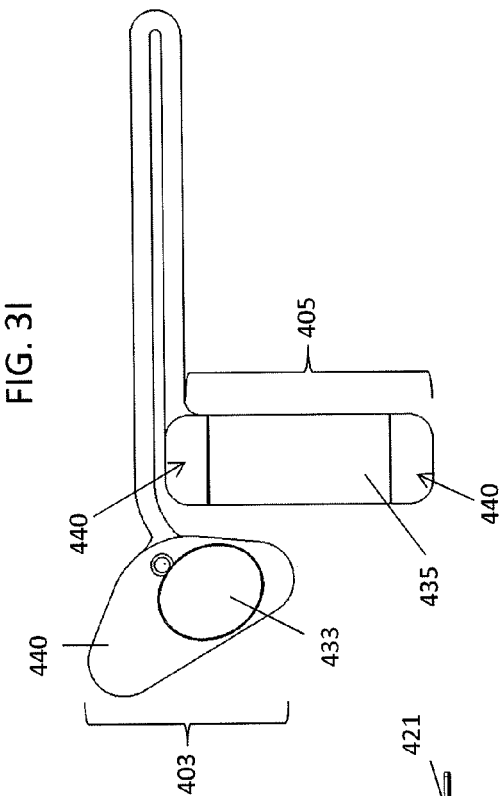
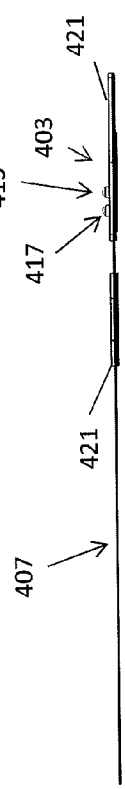

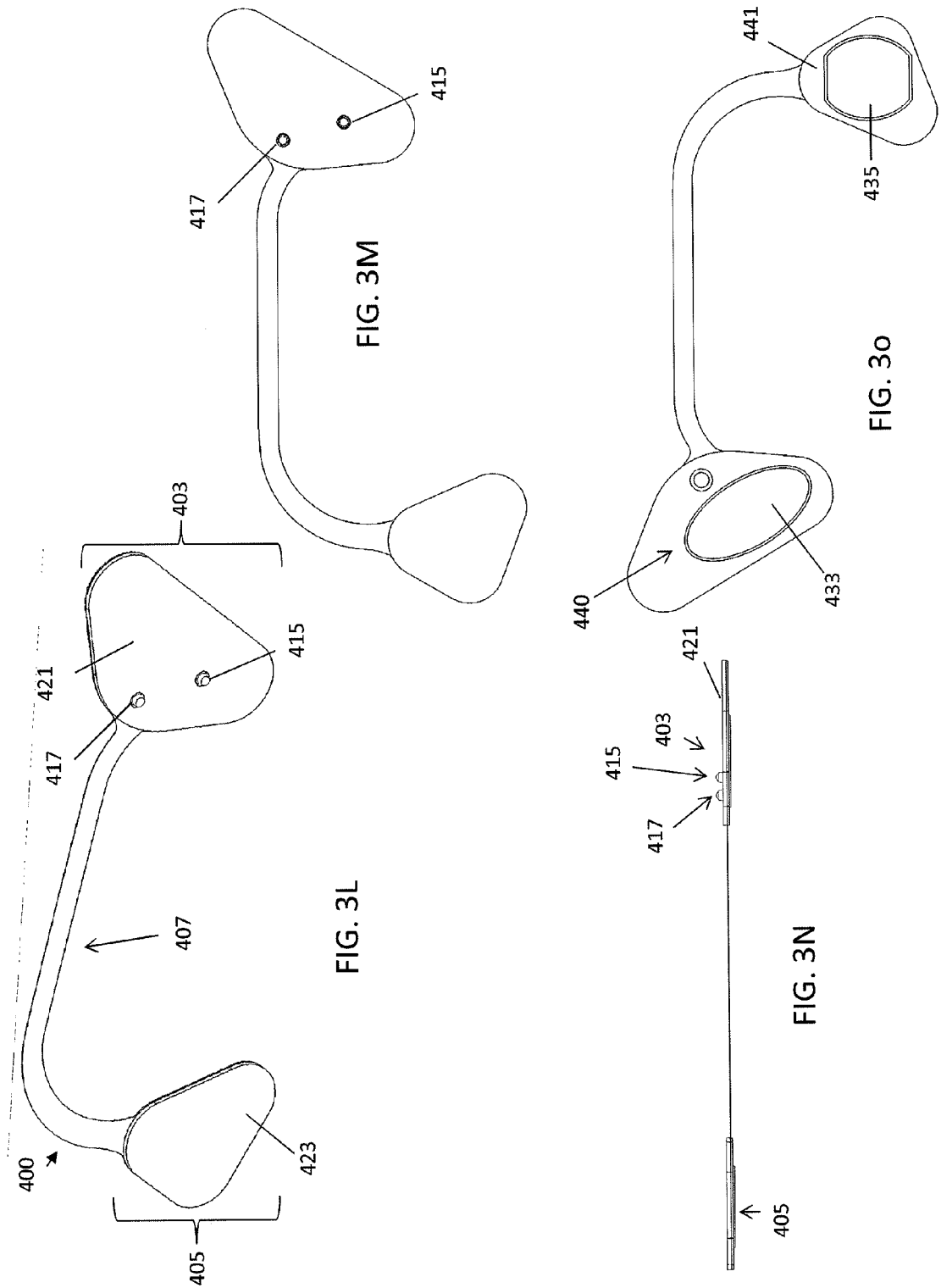

FIG. 4A

| Duration (sec) | 3 | 27 | 60 | 60 | 2 | 3 | 63 | 2 | 30 | 58 | 2 | 18 | 28 | 10 | 60 | 5 |
|---|---|---|---|---|---|---|---|---|---|---|---|---|---|---|---|---|
| Frequency (Hz) | 11000 | 11000 | 11000 | 11000 | 11000 | 11000 | 11000 | 11000 | 11000 | 11000 | 11000 | 11000 | 11000 | 7500 | 6700 | 6700 |
| Current (mA) | 0 | 16 | 18 | 18 | 11 | 18 | 18 | 11 | 18 | 18 | 11 | 18 | 18 | 11 | 11 | 0 |
| Percent charge imbalance | 85 | 85 | 85 | 85 | 85 | 85 | 85 | 85 | 85 | 85 | 85 | 85 | 85 | 100 | 100 | 0 |
| Percent Duty Cycle | 41 | 41 | 41 | 41 | 41 | 41 | 41 | 41 | 41 | 41 | 41 | 41 | 41 | 38 | 38 | 0 |
| End time | 3 | 30 | 90 | 150 | 152 | 155 | 218 | 220 | 250 | 308 | 310 | 328 | 356 | 366 | 426 | 431 |

FIG. 4B

| Component Waveform # | 1 | 2 | 3 | 4 | 5 | 6 | 7 | 8 | 10 | 11 | 12 | 13 | 14 | 15 | 16 | 17 |
|---|---|---|---|---|---|---|---|---|---|---|---|---|---|---|---|---|
| Duration | 2 | 28 | 30 | 60 | 1 | 4 | 65 | 1 | 20 | 69 | 1 | 20 | 59 | 1 | 20 | 59 |
| Freq. (Hz) | 11000 | 11000 | 11000 | 11000 | 11000 | 11000 | 11000 | 11000 | 11000 | 11000 | 11000 | 11000 | 11000 | 11000 | 11000 | 11000 |
| Current (mA) | 1 | 16 | 19 | 19 | 12 | 19 | 19 | 11 | 19 | 19 | 12 | 19 | 19 | 12 | 19 | 19 |
| % Charge imb. | 85 | 85 | 85 | 85 | 85 | 85 | 85 | 85 | 85 | 85 | 85 | 85 | 85 | 85 | 85 | 85 |
| % Duty Cycle | 39 | 41 | 41 | 41 | 41 | 41 | 41 | 41 | 41 | 41 | 41 | 41 | 41 | 41 | 41 | 41 |
| End time | 2 | 30 | 60 | 120 | 121 | 125 | 190 | 191 | 211 | 280 | 281 | 301 | 360 | 361 | 381 | 440 |

| Component Waveform # | 18 | 19 | 20 | 21 | 22 | 23 | 24 | 25 | 26 | 27 |
|---|---|---|---|---|---|---|---|---|---|---|
| Duration | 30 | 30 | 60 | 0.4 | 59.6 | 0.4 | 59.6 | 0.4 | 39.6 | 5 |
| Freq. (Hz) | 7500 | 7500 | 6800 | 7500 | 6700 | 7500 | 6700 | 7500 | 6800 | 6800 |
| Current (mA) | 0 | 12 | 12 | 12 | 12 | 12 | 12 | 12 | 12 | 0 |
| % Charge imb. | 100 | 100 | 100 | 100 | 100 | 100 | 100 | 100 | 100 | 100 |
| % Duty Cycle | 38 | 38 | 38 | 38 | 38 | 38 | 38 | 38 | 38 | 38 |
| End time | 470 | 500 | 560 | 560.4 | 620 | 620.4 | 680 | 680.4 | 720 | 725 |

| Component Waveform # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Duration | 2 | 28 | 60 | 60 | 4 | 6 | 60 | 4 | 26 | 26 | 60 | 4 | 26 | 60 | 4 | 26 | 30 |
| Freq. (Hz) | 11000 | 11000 | 11000 | 10600 | 11000 | 11000 | 10600 | 11000 | 11000 | 11000 | 10600 | 11000 | 11000 | 10600 | 11000 | 11000 | 7500 |
| Current (mA) | 1 | 16 | 19 | 19 | 11 | 16 | 19 | 11 | 19 | 19 | 19 | 11 | 19 | 19 | 11 | 19 | 1 |
| % Charge imb. | 90 | 90 | 90 | 90 | 90 | 90 | 90 | 85 | 90 | 90 | 90 | 85 | 90 | 90 | 85 | 90 | 100 |
| % Duty Cycle | 41 | 41 | 41 | 41 | 41 | 41 | 41 | 41 | 41 | 41 | 41 | 41 | 41 | 41 | 41 | 41 | 41 |
| End time | 2 | 30 | 90 | 150 | 154 | 160 | 220 | 224 | 250 | 250 | 310 | 314 | 340 | 400 | 404 | 430 | 460 |

| Component Waveform # | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|
| Duration | 40 | 60 | 2 | 58 | 2 | 58 | 2 | 58 | 10 | 30 | 30 | 30 | 4 | 16 | 80 | 5 |
| Freq. (Hz) | 7500 | 6700 | 7500 | 6700 | 7600 | 6700 | 7500 | 6700 | 11000 | 11000 | 11000 | 10500 | 11000 | 11000 | 10500 | 10800 |
| Current (mA) | 11 | 11 | 11 | 11 | 11 | 11 | 11 | 11 | 1 | 16 | 19 | 19 | 11 | 19 | 19 | 0 |
| % Charge imb. | 100 | 100 | 100 | 100 | 100 | 100 | 100 | 100 | 85 | 90 | 90 | 90 | 85 | 90 | 90 | 85 |
| % Duty Cycle | 39 | 39 | 39 | 39 | 39 | 39 | 39 | 39 | 39 | 41 | 41 | 41 | 43 | 41 | 41 | 41 |
| End time | 500 | 560 | 562 | 620 | 622 | 680 | 682 | 740 | 750 | 780 | 810 | 840 | 844 | 860 | 940 | 945 |

FIG. 4C

| Component Waveform # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Duration | 1 | 30 | 105 | 15 | 105 | 15 | 105 | 15 | 105 | 15 | 105 | 15 | 30 | 105 | 120 |
| Freq. (Hz) | 9000 | 5000 | 5000 | 12000 | 12000 | 18000 | 18000 | 18000 | 18000 | 5000 | 5000 | 5000 | 5000 | 5000 | 12000 |
| Current (mA) | 0 | 8 | 8.2 | 17.3 | 17.7 | 17.7 | 18.1 | 18.1 | 18.5 | 8.8 | 9 | 0 | 9.1 | 9.2 | 19.8 |
| % Charge imb. | 0 | 40 | 40 | 40 | 40 | 40 | 40 | 40 | 40 | 40 | 40 | 40 | 40 | 40 | 40 |
| % Duty Cycle | 40 | 40 | 40 | 45 | 45 | 60 | 60 | 45 | 45 | 40 | 40 | 40 | 40 | 40 | 45 |
| End time | 1 | 31 | 136 | 151 | 256 | 271 | 376 | 391 | 496 | 511 | 616 | 631 | 661 | 766 | 886 |

| Component Waveform # | 16 | 17 | 18 | 19 | 20 | 21 |
|---|---|---|---|---|---|---|
| Duration | 15 | 105 | 15 | 105 | 15 | 105 |
| Freq. (Hz) | 18000 | 18000 | 12000 | 12000 | 5000 | 5000 |
| Current (mA) | 19.8 | 20.2 | 20.2 | 20.6 | 9.8 | 10 |
| % Charge imb. | 40 | 40 | 40 | 40 | 40 | 40 |
| % Duty Cycle | 60 | 60 | 45 | 45 | 40 | 40 |
| End time | 901 | 1006 | 1021 | 1126 | 1141 | 1246 |

FIG. 5A

| Component Waveform # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Duration | 1 | 59 | 75 | 30 | 90 | 30 | 120 | 30 | 90 | 30 | 30 | 60 | 30 | 90 | 30 | 120 |
| Freq. (Hz) | 9000 | 9000 | 9000 | 750 | 750 | 3600 | 3600 | 750 | 750 | 9000 | 9000 | 9000 | 750 | 750 | 3600 | 3600 |
| Current (mA) | 0 | 9.1 | 10.9 | 3 | 3.1 | 8 | 9.3 | 3.2 | 3.3 | 3 | 9.5 | 11.4 | 3.3 | 3.4 | 8.5 | 9.8 |
| % Charge imb. | 30 | 30 | 30 | 30 | 35 | 40 | 40 | 35 | 35 | 30 | 30 | 30 | 30 | 35 | 40 | 40 |
| % Duty Cycle | 50 | 50 | 50 | 35 | 40 | 40 | 40 | 35 | 40 | 50 | 50 | 50 | 35 | 40 | 40 | 40 |
| End time | 1 | 60 | 135 | 165 | 255 | 285 | 405 | 435 | 525 | 555 | 585 | 645 | 675 | 765 | 795 | 915 |

| Component Waveform # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Duration | 30 | 90 | 60 | 0.4 | 1.2 | 0.4 | 2 | 0.4 | 1.2 | 0.4 | 2 | 0.4 | 1.2 | 0.4 | 2 | 0.4 |
| Freq. (Hz) | 750 | 750 | 750 | 1300 | 1300 | 750 | 750 | 1600 | 1600 | 750 | 750 | 1800 | 1800 | 750 | 750 | 2000 |
| Current (mA) | 3.4 | 3.5 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 | 35 |
| % Duty Cycle | 35 | 40 | 40 | 40 | 40 | 40 | 40 | 40 | 40 | 40 | 40 | 40 | 40 | 40 | 40 | 40 |
| End time | 945 | 1035 | 1095 | 1095.4 | 1096.6 | 1097 | 1099 | 1099.4 | 1100.6 | 1101 | 1103 | 1103 | 1104.6 | 1105 | 1125 | 1125 |

| Component Waveform # | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|
| Duration | 1.2 | 0.4 | 2 | 0.4 | 1.2 | 0.4 | 2 | 0.4 | 1.2 | 0.4 | 2 | 0.4 | 1.2 | 0.4 | 101 |
| Freq. (Hz) | 2000 | 750 | 750 | 2000 | 2000 | 750 | 750 | 2000 | 2000 | 750 | 750 | 2000 | 2000 | 750 | 750 |
| Current (mA) | 4 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 |
| % Duty Cycle | 40 | 40 | 40 | 40 | 40 | 40 | 40 | 40 | 40 | 40 | 40 | 40 | 40 | 40 | 45 |
| End time | 1127 | 1127 | 1129 | 1129.4 | 1130.6 | 1131 | 1133 | 1133.4 | 1134.6 | 1135 | 1137 | 1137 | 1138.6 | 1139 | 1240 |

FIG. 5B

Add-in example

| Component Waveform # | 1 | 2 | 3 | 4 | 5 | 6 |
|---|---|---|---|---|---|---|
| Duration (s) | 0.8 | 0.8 | 0.8 | 0.8 | 4 | 2 |
| Intensity Factor (%) | 80 | 60 | 40 | 20 | 0 | 100 |
| End time (s) | 0.8 | 1.6 | 2.4 | 3.2 | 7.2 | 9.2 |

FIG. 6

| Component Waveform # | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Duration (s) | 5 | 25 | 30 | 30 | 30 | 2 | 28 | 30 | 30 | 30 | 60 | 30 | 30 | 30 | 30 | 5 | 75 | 30 | 30 | 40 |
| Freq. (kHz) | 11 | 11 | 11 | 11 | 11 | 11 | 11 | 11 | 11 | 11 | 11 | 7.5 | 7.5 | 7.5 | 7.5 | 11 | 11 | 10.6 | 11 | 11 |
| Current (mA) | 1 | 18 | 18 | 18 | 18 | 11 | 19 | 19 | 19 | 19 | 19 | 14 | 14 | 14 | 14 | 5 | 18 | 18 | 18 | 18 |
| % Charge imb. | 90 | 90 | 90 | 90 | 90 | 90 | 90 | 90 | 90 | 90 | 90 | 90 | 90 | 90 | 90 | 90 | 90 | 90 | 90 | 90 |
| % Duty cycle | 37 | 37 | 37 | 37 | 37 | 37 | 37 | 37 | 37 | 37 | 37 | 37 | 37 | 37 | 37 | 37 | 37 | 37 | 37 | 37 |
| AM Freq. (Hz) | 800 | 800 | 800 | 800 | 500 | 500 | 500 | 500 | 500 | 500 | 500 | 800 | 500 | 500 | 800 | 800 | 700 | 700 | 500 | 500 |
| AM % duty cycle | 80 | 80 | 80 | 45 | 45 | 45 | 80 | 80 | 45 | 80 | 45 | 80 | 45 | 70 | 70 | 70 | 80 | 40 | 40 | 80 |
| End time (s) | 5 | 30 | 60 | 90 | 120 | 122 | 150 | 180 | 210 | 240 | 300 | 330 | 360 | 390 | 420 | 425 | 500 | 530 | 560 | 600 |

FIG. 7

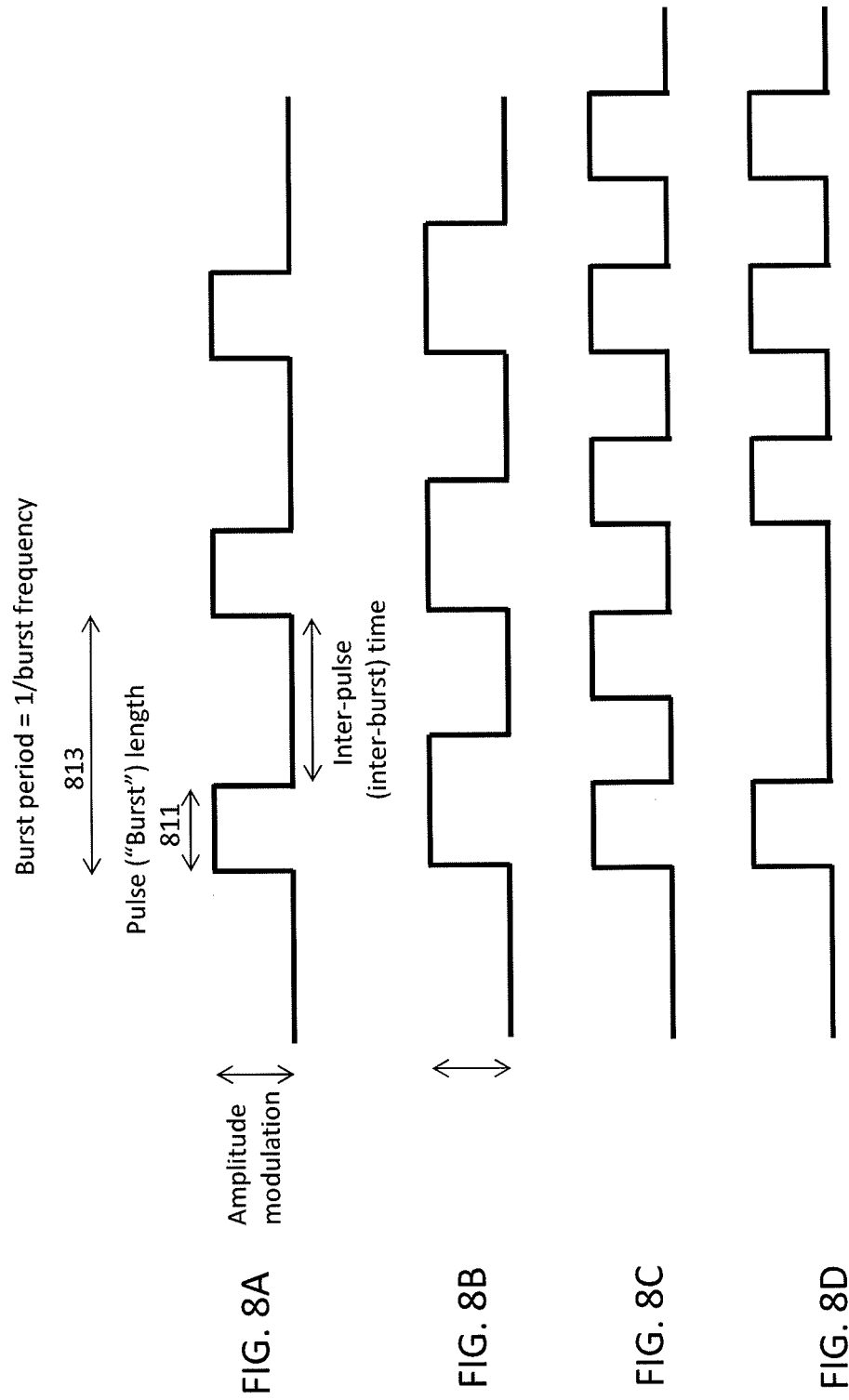

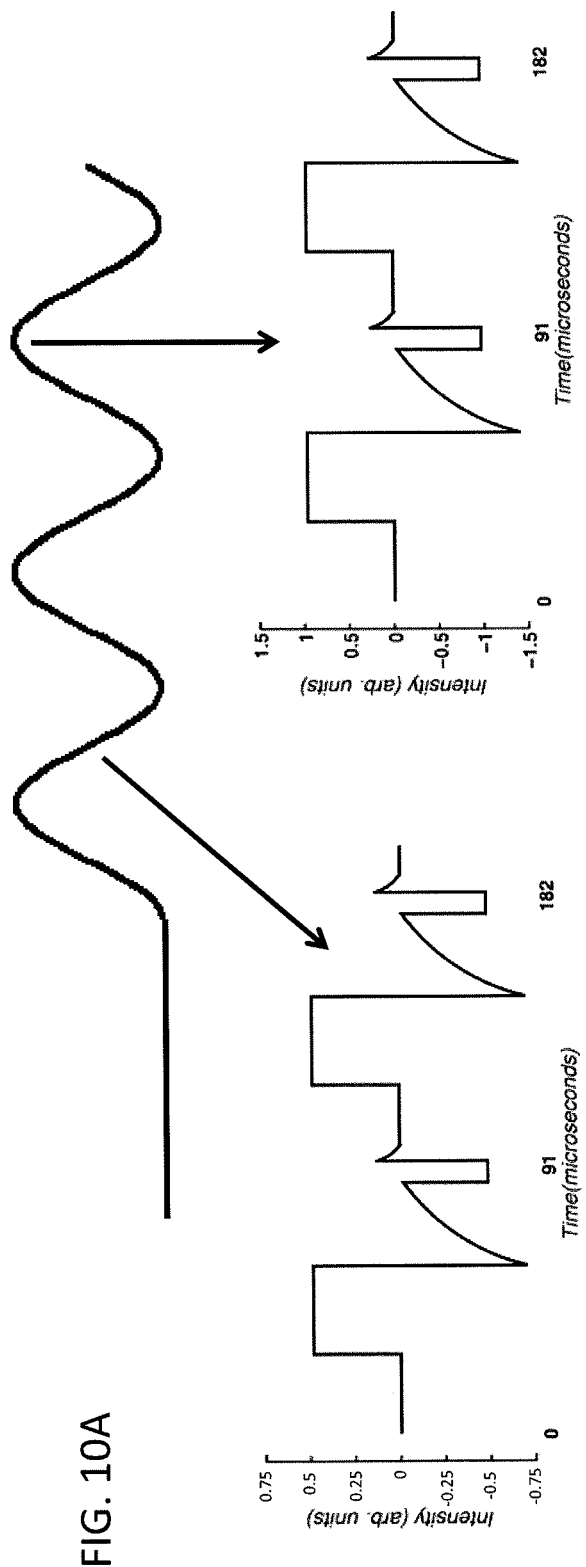
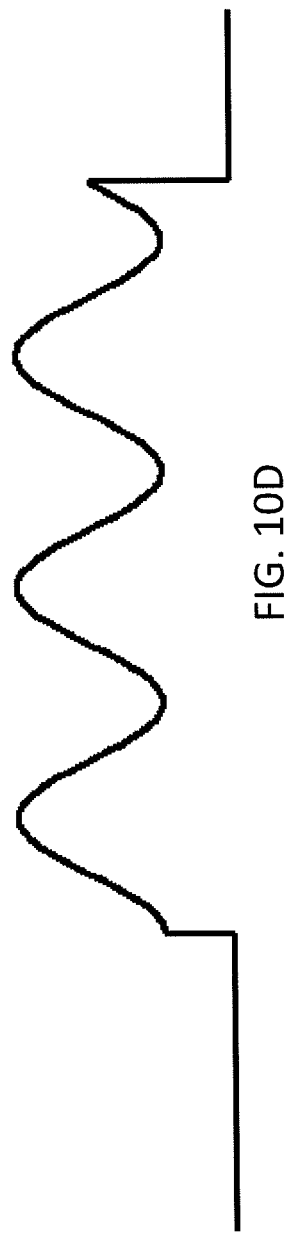
FIG. 10A
FIG. 10B
FIG. 10C
FIG. 10D

| Component waveform # | 1 | 2 | 3 |
|---|---|---|---|
| Duration | 1 | 59 | 540 |
| End Time | 1 | 60 | 600 |
| Frequency (Hz) | 7000 | 7000 | 7000 |
| Current (ma) | 1 | 11 | 11 |
| Percentage DC | 85 | 85 | 85 |
| Duty Cycle % | 49 | 49 | 70 |
| AM Frequency (Hz) | 70 | 70 | 70 |
| AM Duty Cycle % | 35 | 35 | 35 |

FIG. 13

| | 1 | 2 | 3 | 4 | 5 | 6 | 7 | 8 | 9 | 10 | 11 |
|---|---|---|---|---|---|---|---|---|---|---|---|
| Duration | 5 | 55 | 30 | 30 | 30 | 30 | 30 | 30 | 60 | 30 | 30 |
| End Time | 5 | 60 | 90 | 120 | 150 | 180 | 210 | 240 | 300 | 330 | 360 |
| Frequency (Hz) | 11000 | 11000 | 11000 | 11000 | 11300 | 11000 | 11000 | 11300 | 11000 | 11300 | 11000 |
| Current (ma) | 1 | 19 | 19 | 19 | 19 | 19 | 19 | 19 | 19 | 19 | 19 |
| Percentage DC | 90 | 90 | 90 | 90 | 90 | 90 | 90 | 90 | 90 | 90 | 90 |
| Duty Cycle % | 39 | 39 | 39 | 39 | 39 | 39 | 39 | 39 | 39 | 39 | 39 |
| AM Freq. (Hz) | 800 | 800 | 800 | 350 | 350 | 750 | 350 | 750 | 350 | 750 | 350 |
| AM Duty Cycle % | 90 | 90 | 45 | 45 | 90 | 90 | 45 | 90 | 45 | 90 | 45 |

FIG. 14

|  | 1 | 2 | 3 | 4 | 5 | 6 | 7 | 8 | 9 | 10 |
|---|---|---|---|---|---|---|---|---|---|---|
| Duration | 5 | 25 | 30 | 30 | 30 | 2 | 28 | 30 | 30 | 30 |
| End Time | 5 | 30 | 60 | 90 | 120 | 122 | 150 | 180 | 210 | 240 |
| Freq. (Hz) | 11000 | 11000 | 11000 | 11000 | 11000 | 11000 | 11000 | 11000 | 11000 | 11000 |
| Current(ma) | 1 | 18 | 18 | 18 | 18 | 11 | 19 | 19 | 19 | 19 |
| Percentage DC | 90 | 90 | 90 | 90 | 90 | 90 | 90 | 90 | 90 | 90 |
| Duty Cycle % | 37 | 37 | 37 | 37 | 37 | 37 | 37 | 37 | 37 | 37 |
| AM Freq. (Hz) | 800 | 800 | 800 | 800 | 500 | 500 | 500 | 800 | 500 | 800 |
| AM Duty Cycle % | 80 | 80 | 80 | 45 | 45 | 45 | 80 | 80 | 45 | 80 |

|  | 11 | 12 | 13 | 14 | 15 | 16 | 17 | 18 | 19 | 20 |
|---|---|---|---|---|---|---|---|---|---|---|
| Duration | 60 | 30 | 30 | 30 | 30 | 5 | 75 | 30 | 30 | 40 |
| End Time | 300 | 330 | 360 | 390 | 420 | 425 | 500 | 530 | 560 | 600 |
| Freq. (Hz) | 11000 | 7500 | 7500 | 7500 | 7500 | 11000 | 11000 | 10600 | 11000 | 11000 |
| Current(ma) | 19 | 14 | 14 | 14 | 14 | 5 | 18 | 18 | 18 | 18 |
| Percentage DC | 90 | 90 | 90 | 90 | 90 | 90 | 90 | 90 | 90 | 90 |
| Duty Cycle % | 37 | 37 | 37 | 37 | 37 | 37 | 37 | 37 | 37 | 37 |
| AM Freq. (Hz) | 500 | 800 | 500 | 500 | 800 | 800 | 700 | 700 | 500 | 500 |
| AM Duty Cycle % | 45 | 80 | 45 | 70 | 70 | 70 | 80 | 40 | 40 | 80 |

FIG. 15

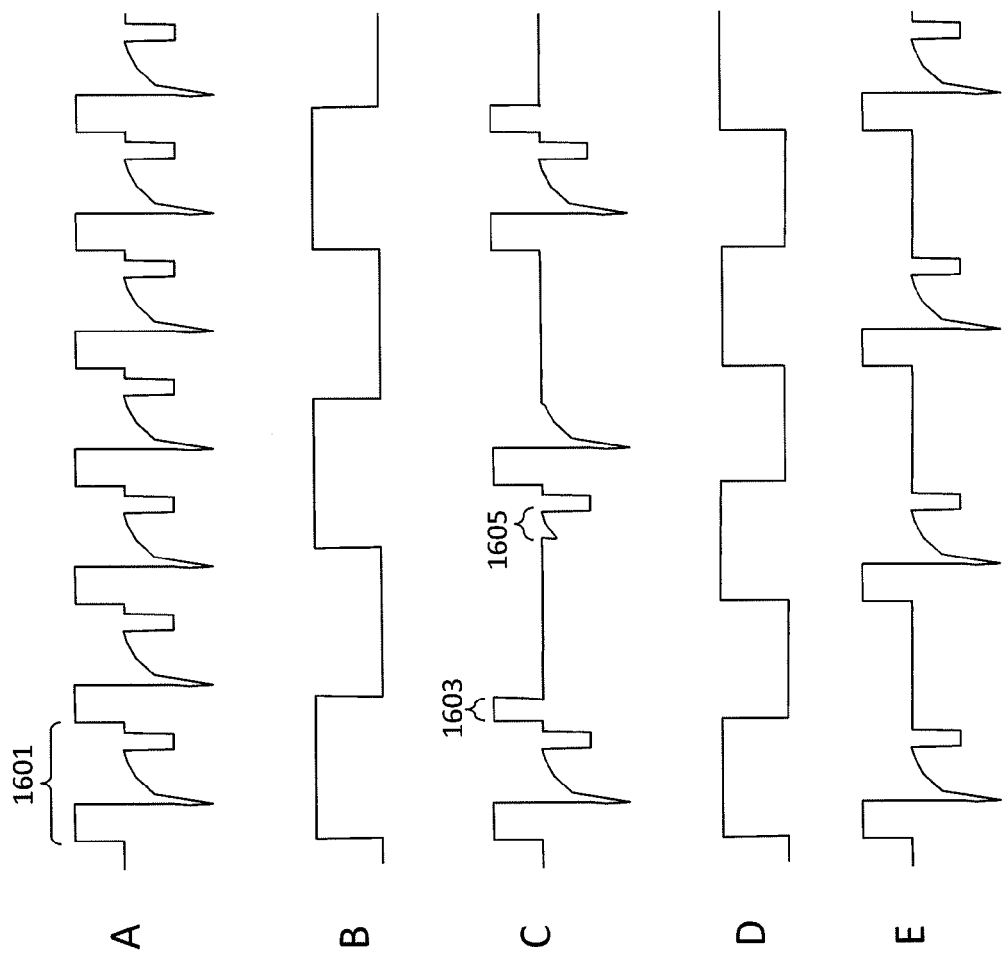
FIGS. 16A-E

METHODS AND APPARATUSES FOR CONTROL OF A WEARABLE TRANSDERMAL NEUROSTIMULATOR TO APPLY ENSEMBLE WAVEFORMS

CROSS REFERENCE TO RELATED APPLICATIONS

This application claims priority to the following provisional patent applications, each of which is herein incorporated by reference in its entirety: U.S. Provisional Patent Application No. 61/994,860, titled "SYSTEMS, DEVICES, AND METHODS FOR TRANSDERMAL ELECTRICAL STIMULATION WAVEFORM DESIGN AND USE," and filed on May 17, 2014; and U.S. Provisional Patent Application No. 62/100,029, titled "METHODS AND APPARATUSES FOR DELIVERY OF ENSEMBLE WAVEFORMS," and filed on Jan. 5, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates generally to methods and apparatuses for noninvasive neuromodulation, and more specifically to transdermal electrical stimulation systems using complex waveform compositions adapted to evoke a particular cognitive effect and control systems for controlling these systems so that they can deliver these complex waveform compositions.

BACKGROUND

Noninvasive neuromodulation technologies that affect neuronal activity can modulate the pattern of neural activity and cause altered behavior, cognitive states, perception, and motor output without requiring an invasive procedure. For example, transcranial/transdermal electric stimulation (hereinafter "TES") through scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Application Publication No. 2011/0144716; and Lebedev et al. U.S. Patent Application Publication No. 2009/0177243). tDCS systems with numerous electrodes and a high level of configurability have been disclosed (see for example Bikson et al. U.S. Patent Application Publication Nos. 2012/0209346, 2012/0265261, and 2012/0245653), as have portable TES systems for auto-stimulation (Brocke U.S. Pat. No. 8,554,324).

Typically, TES has been used therapeutically in various clinical applications, including treatment of pain, depression, epilepsy, and tinnitus. In at least some cases of TES therapeutic use, more data concerning the efficacy of TES in treatment is needed. Despite the research to date on TES neuromodulation, existing systems and methods for TES are lacking in at least some cases regarding the design and use of effective TES waveforms. Available systems are limited regarding the design and delivery of TES waveforms. Moreover, available systems do not permit the user to modulate a predetermined/preconfigured electrical stimulation protocol.

For example, U.S. Pat. No. 8,554,324 to Brocke discloses a mobile system for TES auto-stimulation by a user. Brocke further describes an embodiment wherein a wired or wireless remote control is used to control an electrical stimulation generator, as well as the use of smartphones, cellular telephones, or PDAs as a remote control. However, the systems and methods described by Brocke are lacking in at least some instances for defining, acquiring, and/or delivering effective TES waveforms to a user.

Indeed most TES systems are described with only rudimentary waveforms, and typically apply the same stimulation (or repeated versions of the same basic stimulation set), including simple ramps up and down. Such stimulation is not specific to a particular effect (e.g., cognitive effect such as calming or energizing a subject) and may not be universally effective. What is needed are detailed waveform patterns that are effective to modify a subject's cognitive state across a variety of subjects.

Thus, systems, devices, and methods for applying such complex waveforms by a wearable TES system would be advantageous. Described herein are methods and apparatuses (including devices and systems) for neurostimulation to apply waveforms, which may be referred to as ensemble waveforms, that include numerous sequential sub-components in which a subset of waveform parameters found by the inventors to be important for effective neuromodulation may be altered alone or in combinations at different portions of the delivered waveform to achieve high levels of efficacy and comfort in modulating a subject's (user's) cognitive state.

Also described herein are systems, devices, and methods for transmitting waveform parameters of an ensemble waveform to a neurostimulator controller that achieve robust, efficient, and reliable control of the neurostimulator with regard to transmitting various waveform parameters of an ensemble TES waveform.

SUMMARY OF THE DISCLOSURE

Described herein are methods and apparatuses for delivering neurostimulation using ensemble waveforms. In general, an ensemble waveform typically includes a series or ordered set of waveform parameters, where the set of waveform parameters may specify peak current amplitude (also referred to as peak current intensity, and which in general may refer to the peak positive-going current intensity and/or the peak negative-going current intensity), frequency, duty cycle, percent charge imbalance, and optionally, capacitive discharge state. Each set may also include a time specifying the duration that these waveform parameters are valid, and in some variations, a ramping value indicating the value that the parameter is ramped over and, optionally, the pattern of ramping (i.e., linear, step-wise linear, exponential, etc.). The set of these waveform parameters, duration, and ramping values may together define a stimulation protocol having a plurality of different waveform parameters that are arranged sequentially. For example, an ensemble waveform may include a series of 3 or more (e.g., 4 or more, 5 or more, 6 or more, 7 or more, 8 or more, 9 or more, 10 or more, etc.) component waveforms, wherein component waveforms are typically biphasic and each has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. Each component waveform may also include a ramping time or ramping indicator, indicating that any waveform parameter that changes from a preceding component waveform parameter is to be ramped to the new value over the duration of the component waveform (or over the duration of the ramping time in some variations). Functionally, a waveform ensemble may be created to evoke a particular cognitive effect, such as relaxation, calmness, energy, etc. A waveform ensemble may also be created to be comfortable and effective with a particular neurostimulator device and electrodes. Examples of waveform ensembles are described herein.

In general, also described herein are methods of modifying a subject's cognitive state by transdermal electrical stimulation (TES) using an ensemble waveform. For example, the methods described herein may be methods of modifying a subject's cognitive state by TES of an ensemble waveform comprising a series of (e.g., five or more) component waveforms, wherein each component waveform has a duration of between about 100 ms and 10 min, and wherein each component waveform has a predetermined ramping time between 0 sec and the duration of the component waveform and a predetermined set of waveform properties comprising an intensity, a frequency, a duty cycle, and a percent charge imbalance, and wherein each component waveform except a first component waveform differs from a component waveform that immediately precedes it in the series by one or more of the ramping time or waveform properties. Any of these methods may include delivering a current between a pair of electrodes configured to be placed on the subject's head or head and neck, wherein the delivered current is based on the ensemble waveform.

A method of modulating a subject's cognitive state by transdermal electrical stimulation (TES) may include: delivering a current based on an ensemble waveform between a pair of electrodes on the subject's head or head and neck, wherein the ensemble waveform comprises a series of 5 or more component waveforms, wherein each component waveform may be biphasic and each has a duration and a predefined set of waveform parameters including a frequency, an intensity, a duty cycle, and a percent charge imbalance, wherein at least one of the waveform parameters of each component waveform is different from the waveform parameters of a component waveform preceding it, following it, or preceding and following it in the series. In some variations, some of the component waveforms may be unipolar, rather than biphasic (e.g., may include very brief unipolar pulses, or even periods of direct current (non-pulsed) stimulation). However in general the component waveforms described herein are biphasic.

Methods of modulating a subject's cognitive state by transdermal electrical stimulation (TES) based on an ensemble waveform may generally include sequentially delivering the linked string of component waveforms forming the ensemble waveform. For example, an ensemble waveform may comprise a series of 5 or more component waveforms, wherein each component waveform is biphasic and has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. For example, a method of modulating a subject's cognitive state by transdermal electrical stimulation (TES) based on an ensemble waveform may include: delivering a current with delivered current waveform parameters comprising a frequency, an intensity, a duty cycle, and a percent charge imbalance, wherein delivering comprises: during a first time period that is equal to the duration of the first component waveform, setting the delivered current waveform parameters to the first waveform parameters, wherein one or more of the waveform parameters of the delivered current waveform parameters are scalable by a user adjustment; and during a set of subsequent and sequential time periods that are equal to the subsequent and sequential durations of the series of component waveforms, sequentially adjusting the delivered current waveform parameters to the waveform parameters of each component waveform of the series of component waveforms during each time period in the set of time periods corresponding to the duration of the component waveform, wherein one or more of the delivered current waveform parameters are scaled by a user adjustment.

As described herein an ensemble waveform may include three or more component waveforms (e.g., four or more, five or more, six or more, seven or more, eight or more, nine or more, etc.). Five or more component waveforms may be used, for example, in instances in which there are a minimum of component waveforms for ramping up at beginning of the neurostimulation, ramping down at end of the neurostimulation; and at least two transitions within the main waveform, such as a either a quick change in intensity, frequency etc., and then back to the previous value, or a shift between three waveform parameter sets.

As used herein the term ramping may refer to the transition between a previous predetermined set of waveform properties (including transitioning from or to no waveform properties or zero-value properties at the start and end of a neurostimulation, respectively), and a new predetermined set of waveform properties that occurs over time (ramping time). In some variations only a single property from the set of waveform properties is ramped during a component waveform (e.g., one of: current amplitude/intensity, frequency, duty cycle, percent charge imbalance). In some variations, ramping may transition between two or more properties (e.g., two or more of: current amplitude/intensity, frequency, duty cycle, percent charge imbalance). Ramping may be linear (e.g., constant change in the waveform property or properties being changed over time), or there may be a ramping profile, including smooth (e.g., exponential, etc.) or discrete (e.g., step-wise linear, etc.), or other more complex patterns that may include a stochastic (i.e., random, not pre-determined) feature, as well as a particular ramping time over which the ramping profile is applied. For variations in which the ramping time is zero, no ramping may occur, and instead the value may be stepped to the new value in the waveform parameters being applied for that period of time, although the transition to the new value may not be fully instantaneous, depending on the transitioning capabilities of the devices (e.g., the clock period, circuit capacitance, etc.). For example, for a ramping time of 0 sec, the change in waveform properties happens as soon as possible using the device, e.g., immediately (or in a brief period of time limited, for example, by the communication in the system and/or speed of processor on the neurostimulator device).

In general, sequential waveform components may differ from a preceding or following waveform by one or more property values of the component waveform, but may not necessarily differ from all previous waveform components that are not adjacent to it in the sequence forming the ensemble waveform (i.e. some waveform component sets may be repeated as non-sequential elements of an ensemble waveform).

Although the methods and apparatuses described herein are generally directed to methods and apparatuses for delivery to a subject's head or head and neck, any of the methods and apparatuses described herein may also be useful for other regions of the body. For example, the methods and apparatuses may be used with other electrode locations, including electrode locations that are only on the body below the neck (e.g., arms, legs, torso, etc.). In particular, the ensemble waveforms described herein may generally be useful when electrically stimulating regions of the body other than the head and neck. In addition the ensemble waveforms described herein for neurostimulation to change cognitive states may be used for other electrical stimulation methods (such as TENS, etc.).

In general, the methods and systems described herein may be used in a method or apparatus in which the user may self-adjust the perceived intensity of the applied waveform. As used herein perceived intensity refers to the perceived experience evoked by the applied waveform, including the cognitive effect (e.g., a state of calmness, a state of increased energy, etc.) and/or the physical effects of stimulation that may be localized to the region at and/or around the electrode contact site (e.g., tingling, stinging, burning, shocking, prickling, itching, etc.). A user may adjust the perceived intensity by adjusting a control (dial, knob, slider, button, etc.) that increases or decreases one or more of the waveform parameters (frequency, peak current, percent charge imbalance, duty cycle) either directly or indirectly. The control may adjust a percentage between, e.g., 0 and 100% or any subrange thereof, of the applied waveform parameters. The adjustment may adjust multiple waveform parameters using a relationship between different waveform parameters. As one non-limiting example, increasing the perceived intensity may increase the current amplitude (e.g., from 5 mA to 18 mA), while simultaneously increasing the frequency (e.g., from 7 kHz to 15 kHz). Thus, the user-selected modification of the perceived intensity may adjust one or more of the waveform parameters by applying a scaling formula. In some variations, the scaling may be based on the range, e.g., adjusting one or more parameters (or differently scaling them) over different ranges of the perceived intensity adjustment. For example, the current amplitude when adjusting the perceived intensity to be between 0% and 25% of the peak or target waveform parameter values, adjusting the frequency when adjusting between 25% and 50% of the peak or target waveform parameter values, adjusting the duty cycle when adjusting between 50% and 75% of the peak or target waveform parameter values, and adjusting the current amplitude and frequency when adjusting between 75% and 100% of the peak or target waveform parameter values.

In general, in systems and methods in which the user is permitted to adjust the perceived intensity (which may result in a multiplier/percent/modifier of the applied waveform parameters), as the ensemble waveform is being applied and transitioning from one component waveform to the next, the same user adjustment to the perceived intensity may be applied to the new parameters. For example, if the user adjustment to the perceived intensity is 50% of the applied perceived intensity during a first period (e.g., when applying one or more composite waveforms), the same 50% adjustment (e.g., to one or more of: current amplitude, frequency, duty cycle, percent charge imbalance) will be made to the next composite waveform, until and unless the user again adjusts the perceived intensity. For example, a user adjustment during a preceding component waveform time period may automatically be applied to the waveform parameters (frequency, peak current amplitude, or frequency and peak current amplitude, etc.) of subsequent time periods. In some variations the system or device may be configured to initially set the value of the adjustment to perceived intensity as 50% (e.g., half of the maximum perceived intensity set by the waveform parameters of the ensemble waveform). In other variations, the system or device may be configured to initially set the value of perceived intensity to a custom value for a particular user based on their control of perceived intensity during previous TES sessions.

Any of the methods and apparatuses described herein, e.g., ensemble waveforms, may also be used with systems and methods that do not permit the user to adjust the perceived intensity.

In particular, the methods describe herein may be useful for delivering neurostimulation to modify a subject's cognitive state by applying electrodes in predetermined locations effective for inducing a perception of enhanced energy or a perception of increased calmness. For example, any of these methods may include placing a first electrode of a portable TES applicator on the subject's skin on a temple and/or forehead and a second electrode of a portable TES applicator on a second region (e.g., for calm, at the subject's neck and, for energy, behind the subject's ear over the mastoid region), e.g., placing a first electrode of a portable TES applicator on the subject's skin on a temple and/or forehead and placing a second electrode on the subject's skin on either the subject's mastoid region or on the subject's neck.

In general, each component waveform of a waveform ensemble may have a duration of between about 100 ms and 10 min. The component waveforms may include a ramping (or ramp) time of the values of the waveform parameters defining the component waveform (current amplitude, frequency, duty cycle, percent charge imbalance). In some variation, the ramp time is a ramp register, which may be 0 (if not ramped) or 1 if ramped (e.g., linearly to step-wise linearly) over the entire duration of the waveform. For example, the ramping time may be either 0 seconds or the duration of the component waveform. In other examples, a component waveform may maintain static values for each waveform parameter and thus not include any ramping. In any of the methods and apparatuses described herein, the waveform parameters may include start and stop values for each class of waveform parameter (e.g., current amplitude, frequency, duty cycle, percent charge imbalance, etc.) where, if the start and stop values are different, a system may ramp between them using a predefined ramping parameter.

In some variations, the set of waveform parameters (or waveform properties) may generally comprises a peak intensity of between about 5 mA and 25 mA, a frequency between about 500 Hz and 30 kHz (e.g., having a lower bound of greater than 550, 600, 650, 700, 750, etc. Hz), a duty cycle of between about 20 and 80%, and a percent charge imbalance of between about 10% and 100%.

As mentioned, in any of these variations, the method (or an apparatus configured to perform or apply the method) may include receiving a user adjustment to the delivered current (e.g., adjusting the perceived intensity). For example, the method may include receiving a user adjustment to the delivered current, and delivering the current may include adjusting the frequency, intensity, duty cycle, percent charge imbalance, or more than one of these parameters based on the user adjustment.

The ensemble current waveforms (e.g., ensemble waveforms), methods of applying them to treat a user, and methods of controlling neurostimulator devices described herein may be used for virtually any type of stimulation, but are particularly helpful in preventing or reducing habituation which may otherwise occur with TES neurostimulation/neuromodulation, as will be described in greater detail below.

For example, a method of modifying a subject's cognitive state by transdermal electrical stimulation (TES) to a subject's head or head and neck from two or more electrodes that are coupled to a neurostimulator may include: applying an ensemble current waveform between the two or more electrodes, wherein the ensemble current waveform comprises a series of component waveforms that are sequentially applied, wherein each component waveform comprises a duration (e.g., between about 100 milliseconds and about 600 seconds, between about 100 milliseconds and about 300 seconds, between about 100 milliseconds and about 150 seconds, or any range between a lower value of about: 100, 125, 150, 175, 200, 225, 250, 275, 300, 350, 400, 450, 500, 1000, 1500, 2000, 2500, etc. msec, and an upper value of about: 600, 450, 300, 250, 200, 150, 100, 75, 50, 25, 20, 15, 14, 13, 12, 11, 10, 9, 8, 7, 6, 5 etc. seconds), a current amplitude, a frequency, a percent charge imbalance, and a percent duty cycle; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

A method of modifying a subject's cognitive state by transdermal electrical stimulation (TES) may include applying TES to a subject's head or head and neck from two or more electrodes that are coupled to a neurostimulator. Such methods may include: attaching the first electrode to the user's temple and/or forehead region; attaching the second electrode to a second location on the user's head and/or neck; applying an ensemble current waveform between the two or more electrodes, wherein the ensemble current waveform comprises a series of component waveforms that are sequentially applied, wherein each component waveform comprises a duration between about 100 milliseconds and about 600 seconds, a current amplitude between about 3 mA and 25 mA, a frequency between about 700 Hz and 30 kHz, a percent charge imbalance between about 10% and 100%, and a percent duty cycle between about 20 and 80%; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

Applying the ensemble current waveform may include applying component waveforms that are biphasic. For example, applying the ensemble current waveform may comprise applying a series of greater than 5 component waveforms. Applying the ensemble current waveform may comprise applying the series of component waveforms wherein a component waveform in the series differs from another component waveform immediately before and/or immediately after the component waveform in the series by two or more of: the current amplitude, the frequency, the percent charge imbalance, and the percent duty cycle. Applying the ensemble current waveform may comprise sequentially applying component waveforms in the series for their duration and, during the duration of each component waveform, ramping one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

Any of the methods described herein may include placing a first electrode of a portable TES applicator on the subject's skin on a temple or forehead, for example, and placing a second electrode on the subject's skin on either the subject's mastoid region or on the subject's neck.

Applying an ensemble current waveform may include sequentially applying the series of component waveforms wherein the absolute value of the peak current amplitude of the component waveforms is between about 3 mA and 30 mA (e.g., between about 4 mA and 30 mA, between about 3 mA and 25 mA, between about 5 mA and 30 mA, etc., including any range between a lower limit of about 2, 3, 4, 5, 6, 7, etc. mA and an upper range of about 15, 20, 22, 23, 24, 25, 26, 27, 28, 29, 30, 31, 32, 33, 34, 35, etc. mA). Applying an ensemble current waveform may comprise sequentially applying the series of component waveforms wherein the frequency of the component waveforms is between about 700 Hz and 30 kHz (e.g., between about 550 Hz and about 50 kHz, between about 600 Hz and about 40 kHz, between about 650 Hz and about 35 kHz, etc., including any range between a lower limit of about 500, 550, 575, 600, 625, 650, 675, 700, 725, 750, 775, 800, 825, 850, 875, 900, etc. Hz, and an upper limit of about 10 kHz, 15 kHz, 20 kHz, 25 kHz, 30 kHz, 35 kHz, 40 kHz, 45 kHz, 50 kHz, etc.). Applying an ensemble current waveform may include sequentially applying the series of component waveforms wherein the duty cycle of the component waveforms is between about 20 and 80% (e.g., any range between a lower limit of about 20, 25, 30, 35, 40, 45, 50, etc., percent, and an upper limit of about 50, 55, 60, 65, 70, 75, 80, 85, etc., percent, where the lower limit is always less than the upper limit). Applying an ensemble current waveform may include sequentially applying the series of component waveforms wherein the percent charge imbalance of component waveforms is between about 10% and 100% (or any sub-range between a lower limit of about 5, 10, 15, 20, 25, 30, 35, 40, 45, 50, etc., percent, and an upper limit of about 50, 55, 60, 65, 70, 75, 80, 85, 90, 95, etc., percent, where the lower limit is always less than the upper limit, and the upper limit may be 100%, in which case the pulsed signal is all positive-going or all negative going, as described below).

In any of the variations described herein, applying an ensemble current waveform may comprise modifying the ensemble waveform during application by a user intensity adjustment factor. For example, a user (operating a control device) may manually, and dynamically, adjust the perceived intensity by moving a control to adjust the applied energy; the output of the control may be transmitted to the neurostimulator and used to adjust the intensity of the actual applied signal, by adjusting (e.g., scaling) one or more of peak current, percent duty cycle, and/or frequency. For example, any of the methods described herein may include receiving a user intensity adjustment factor in the neurostimulator (i.e. via a user interface such as a touchscreen or button) and adjusting the ensemble waveform delivered by the user intensity adjustment factor; any of the methods described herein may also include receiving a user intensity adjustment factor in the neurostimulator and adjusting the ensemble waveform delivered by the user intensity adjustment factor by scaling one or more of the frequency, duty cycle, and intensity of the applied ensemble current.

Any of the methods described herein may be performed by a device (e.g., a dedicated device) that includes one or more structures to perform the recited methods. For example, a transdermal electrical stimulation (TES) applicator apparatus for modifying a subject's cognitive state, may include: a body; a first connector configured to connect to a first electrode; a second connector configured to connect to a second electrode; and a TES controller at least partially within the body configured to apply an ensemble current waveform between the two electrode connectors, wherein the ensemble current waveform comprises a series of component waveforms that are sequentially applied, wherein each ensemble waveform comprises a duration between about 100 milliseconds and about 600 seconds, a current amplitude, a frequency, a percent charge imbalance, and a percent duty cycle; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

In any of these variations, the TES controller may be configured to apply an ensemble current waveform comprising biphasic pulses. In any variation of these controllers, the TES controller may be configured to apply the series, wherein the series comprises 5 or more (e.g., more than 4, 5, 6, 7, 8, 9, 10, 11, 12, 13, 14, 15, 16, 17, 18, 19, 20, 25, 30, 35, 40, 45, 50, etc.) ensemble current waveforms.

In any of the variations described herein, the TES controller may be configured to apply the series of component waveforms wherein a component waveform in the series differs from another component waveform immediately before and/or immediately after the component waveform in the series by two or more of: the current amplitude, the frequency, the percent charge imbalance, and the percent duty cycle.

The TES controller may be configured to sequentially apply component waveforms in the series for their duration and, during that duration, ramp one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

As suggested above, the TES controller may be configured to apply an ensemble current waveform by sequentially applying the series of component waveforms wherein the current amplitude of the component waveforms is between about 3 mA and 25 mA (or the current amplitude is within the ranges discussed above, which may refer to peak current amplitude during the duration of the component waveform). The TES controller may be configured to apply an ensemble current waveform by sequentially applying the series of component waveforms wherein the frequency of the component waveforms is between about 700 Hz and 30 kHz (or any of the frequency ranges discussed above). The TES controller may be configured to apply an ensemble current waveform by sequentially applying the series of component waveforms wherein the duty cycle of the component waveforms is between about 20% and 80% (or any of the percent duty cycle ranges described above). The TES controller may be configured to apply an ensemble current waveform by sequentially applying the series of component waveforms wherein the percent charge imbalance of component waveforms is between about 10% and 100%.

In any of the variations described herein, the TES controller may be configured to apply an ensemble current waveform by sequentially applying the series of component waveforms wherein applying an ensemble current waveform comprises modifying the ensemble waveform during application by a user intensity adjustment factor. Any of the apparatuses described herein may include a wireless receiver circuit, the wireless receiver circuit configured to receive an intensity adjustment factor and further wherein the TES controller is configured to adjust the ensemble waveform delivered by the user intensity adjustment factor.

Further, any of these apparatuses may include a wireless receiver circuit, the wireless receiver circuit configured to receive an intensity adjustment factor, wherein the TES controller is configured to adjust the ensemble waveform delivered by the user intensity adjustment factor by scaling one or more of the frequency, percent duty cycle, and intensity of the applied ensemble current.

Also described herein are methods of and systems for separately modulating any of the ensemble waveforms described herein, including applying an envelope or scaling signal (which may be herein referred to as an amplitude modulation) to all or, in some variations, one or more portions (e.g., one or more component waveforms) of the ensemble waveform. The envelope is typically a lower frequency (e.g., 1 Hz to 900 Hz, 1 Hz to 300 Hz, 1 Hz to 400 Hz, 1 Hz to 500 Hz, 1 Hz to 600 Hz, 1 Hz to 700 Hz, 1 Hz to 800 Hz, 1 Hz to 1 kHz, etc., and is typically lower than the frequency of the component waveforms that it is modulating) pulsed scaling waveform. The low-frequency pulsed signal (envelope signal or amplitude modulation signal, also referred to as a burst signal) may be a square wave, sawtooth wave, etc., and may have a value of between 1 and 0 (or −1 and 1) so that the resulting signal includes bursts and/or modulated intensities of the higher-frequency component waveforms forming the ensemble waveform. As described in greater detail below, applying this amplitude modulation over even one or a few of the component waveforms forming the ensemble waveform may provide a tremendous advantage both in power efficiency for the system and efficacy for inducing a cognitive and/or physiological effect while potentially reducing or eliminating pain or discomfort associated with stimulation.

In general, any of the ensemble waveforms described herein may be fully or partially amplitude modulated. In particular, to reduce the potential for pain (e.g., from capacitive build-up, pH changes in the skin, and the like), the methods and apparatuses described herein that include amplitude modulation as described herein may also be adapted so that the amplitude modulation prevents truncation of the fundamental pulses being applied during a component waveform. The modulation frequency may be set and/or adjusted to prevent truncating the pulses (signals). One method to prevent truncating the (fundamental or unit) pulses of the ensemble waveform, which may be biphasic (see, e.g., FIG. 1A, described in greater detail below) is to set the amplitude modulation period (duration) so that it is a multiple of the time for one period of a component waveform to which the modulation is being applied, for example by setting the amplitude modulation duration to be a multiple of an inverse of the component waveform frequency. For example, when the amplitude modulation frequency is set (e.g., by a user) without necessarily avoiding truncating pulses of the component waveforms, it may be adjusted (e.g., either in the neurostimulator apparatus or before the parameters are transmitted to the neurostimulator) so that, for example, the amplitude modulation (AM) frequency is adjusted by subtracting time equivalent to the duration of the truncation that would occur if not adjusted For example, the number of fundamental pulses that occur per second of the component waveforms (the frequency of the component waveform being modulated) times the duration of the original/unadjusted modulation envelope (the inverse of the frequency of the original, or target, not yet adjusted, amplitude modulation frequency) gives the number of pulses within the duration of the original modulation envelope, which is a whole number plus the remaining fraction; the modulation frequency may be adjusted by multiplying this fraction by the duration of each fundamental pulse (the time for one period of a cycle, $t_c$) of the component waveform, and subtracting this time from the original/uncorrected duration of the amplitude modulation envelope (the period of the amplitude modulation pulse, which is the inverse of the amplitude modulation frequency), to give the adjusted/corrected duration of the modulation envelope. The adjusted or corrected amplitude modulation envelope frequency for this particular component waveform to avoid truncation is the inverse of the adjusted/corrected duration of the amplitude modulation envelope, and will be slightly shifted relative to the target, original (uncorrected) AM frequency. In another example adjustment to ensure fundamental pulses of a burst are not truncated, the amplitude modulation duty cycle (i.e. the proportion of the amplitude modulation period during which the fundamental pulses are delivered) is adjusted by adding or subtracting duty cycle percentage for rounding to a non-truncated fundamental pulse cycle.

Similarly, the duration of the non-zero portion of the envelope pulse (e.g., in a square pulse envelope, the duration of the "on" portion of the pulse within each period, may be set or adjusted to be a multiple of the duration of the period of the fundamental pulse ($t_c$) for the component waveform being amplitude modulated. When both the period of the envelope of the amplitude modulation and the pulse duration (the time spent above zero within each a pulse of the amplitude modulated envelope) are multiples of the time for the period of one cycle of the component waveform, the pulses of the component waveform will not be truncated.

For example, a method of modulating a user's cognitive state by transdermal electrical stimulation may include: delivering an ensemble current waveform for application between two or more electrodes, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; wherein, prior to delivery, one or more of the component waveforms of the ensemble current waveform is modulated (e.g., amplitude modulated) by setting the current amplitude to zero at a modulation frequency for a modulation duration that does not result in truncated pulses in the delivered waveform.

Thus, in any of the methods and apparatuses described herein, amplitude modulation may be applied to one or more of the component waveforms, and the duration of the envelope applied for amplitude modulation (e.g., the modulation duration, which may also be referred to as the modulation duty cycle) may be a multiple of an inverse of the component waveform frequency. In some variations, and particularly but not exclusively amplitude modulation square waveforms, the duration of the non-zero portion of the pulse (also referred to herein as burst length) is also set or adjusted to be a multiple of an inverse of the component waveform frequency. The inverse of the component waveform frequency is the duration of each cycle of the component waveform. For example, the duration of the modulation pulse is the time for one period of a cycle of the modulation pulse and may also be referred to equivalently as the burst period (or bursting period) of amplitude modulation, and/or the time for one period of the amplitude modulation envelope may be set to or may otherwise equal a multiple of the time for one period of a cycle (one fundamental pulse) of the component waveform.

For example, the modulation duration is generally the inverse of the modulation frequency, and in some examples may comprises a bursting duty cycle divided by the modulation frequency, further wherein the modulation duration is adjusted to prevent truncation of pulses in the delivered waveform. The modulation duration may comprise a bursting duty cycle divided by the modulation frequency, further wherein the modulation duration is adjusted to prevent truncation of pulses in the delivered waveform.

Amplitude modulation may be applied (and devices for delivering current to a user may be adapted to include amplitude modulation) to any ensemble waveform as described herein, including ensemble waveforms having more than 2 component waveforms, e.g., more than 3 component waveforms, more than 4 component waveforms, more than 5 component waveforms, more than 6 component waveforms, more than 7 component waveforms, more than 8 component waveforms, more than 9 component waveforms, more than 10 component waveforms, etc. Each component waveform may be longer than 100 ms as discussed above.

The ensemble current waveform may be modulated by turning off the current for a portion of the amplitude modulation envelope. For example, when applying a square wave envelope for amplitude modulation, the component waveform to which this bursting (amplitude modulation) is applied may be zeroed when the pulse is low (or zero) and it may be multiplied by 1 (passed) when the pulse is high. Alternatively, in some variations, the burst may be modified by scaling, e.g., when using sawtooth, sinusoidal, or other amplitude modulation pulses.

In general, any of the methods described herein may include applying the ensemble current waveform to a user wearing the two or more electrodes, e.g., applying the ensemble current waveform to a user wearing a first electrode of the two or more electrodes on the user's temple and/or forehead region and a second electrode of the two or more electrodes on the neck or mastoid region.

Also in general, the ensemble waveforms may include a plurality (e.g., 2 or more, 3 or more, 4 or more, 5 or more, 6 or more, etc.) component waveforms each having a defined amplitude, frequency, percent duty cycle, and percent charge imbalance. Each component waveform may also have amplitude modulation (e.g., AM on/off) including an amplitude duty cycle frequency (which may be referred to herein as an amplitude modulation frequency, AM frequency). In some variations the amplitude modulation may also include an amplitude modulation duty cycle (AM % duty cycle), which may indicate the percentage of time that the amplitude modulation pulse is "on" during the period of a single amplitude modulation pulse, and may be between 0% (signal totally suppressed, or set to 0) and 100% (all of the signal passed). The amplitude modulation percent duty cycle may be set and/or adjusted to adjust as mentioned above to prevent truncation of the pulses of the component waveform (of the ensemble waveform) being amplitude modulated. For example, percent duty cycle may be adjusted by increasing or decreasing the duration of the non-zero pulse (within the amplitude modulation envelope waveform) so that it is a multiple of the duration of the time for one period of a cycle (e.g., the inverse of the frequency of stimulation) of the component waveform.

Thus, each component waveform may be specified by: current amplitude (typically in mA), frequency (e.g., of the fundamental pulses, typically biphasic), percent duty cycle (e.g., the time spent in the negative peak current plus the time spent in the positive peak current, divided by the time for one period of a cycle of a fundamental pulse), and the percent charge imbalance (e.g., the difference between the time spent in the positive peak current and the time spent in the negative peak current, divided by the sum of the time spent in the positive and negative peak current of a fundamental pulse). The percent charge imbalance may also be referred to as the "percent DC" (or percent direct current). Each component waveform may also specific if capacitive discharging current is to be applied (capacitive discharge "on" or "off") and/or how the capacitive discharge is to be applied (e.g., where in the cycle it is to be discharge, and/or for how long). In addition or alternatively, any of the component waveforms may also include an indicator indicating if amplitude modulation is on and/or the frequency for amplitude modulation and/or the amplitude modulation percent duty cycle (e.g., the duration of a, e.g., square wave, pulse within a single period of the amplitude modulation cycle divided by the total time for the single period of the amplitude modulation cycle (e.g., 1/frequency of the amplitude modulation)). Thus, the apparatuses described herein may be configured to operate with all or some of these parameters specifying each component waveform of the ensemble waveform.

In any of the methods and apparatuses described herein, the ensemble waveform is delivered by sequentially delivering the sequence of component waveforms forming the ensemble waveforms. In general, the duration of each component waveform is between about 100 milliseconds and 600 seconds. Delivering may include sequentially delivering the component waveforms wherein the amplitude of each component waveform is between about 3 mA and about 25 mA. Delivering may include sequentially delivering the component waveforms, wherein the frequency of each, some or any of the component waveform is between about 700 Hz and about 30 kHz. Delivering may comprise sequentially delivering the component waveforms wherein the percent charge imbalance of each component waveform is between about 10% and 100%. Delivering may comprise sequentially delivering the component waveforms wherein the percent duty cycle of each component waveform is between about 20% and 80%.

Methods of modulating a user's cognitive state that include the use of amplitude modulation are also described. For example, a method of modulating a user's cognitive state by transdermal electrical stimulation (TES) to a subject's head or head and neck from two or more electrodes that are coupled to a neurostimulator may include: applying an ensemble current waveform between the two or more electrodes, wherein the ensemble current waveform comprises a series of component waveforms that are sequentially applied, wherein the component waveforms comprise biphasic pulses and wherein each component waveform in the series is different from a component waveform immediately before it and/or immediately after it in the series by one or more of: a duration, wherein the duration is between about 100 milliseconds and about 600 seconds, a current amplitude, a frequency, a percent charge imbalance, and a percent duty cycle; wherein, prior to application, one or more of the component waveforms of the ensemble current waveform is modulated by setting the current amplitude to zero at a modulation frequency for a modulation duration that is a multiple of an inverse of the component waveform frequency.

A method of modulating a user's cognitive state by transdermal electrical stimulation may include: delivering an ensemble current waveform for application between two or more electrodes, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; wherein, prior to delivery, one or more of the component waveforms of the ensemble current waveform is modulated by setting the current amplitude to zero at a modulation frequency for a modulation duration.

Any of the methods described herein may be performed by apparatuses, including hardware, software and firmware, for performing all or some of the steps described. For example a method of modulating a subject's cognitive state using TES as described, and particularly for applying an ensemble waveform and separately (and in some cases independently) amplitude modulating one or more component waveforms forming the ensemble waveform may be performed using a wearable transdermal electrical stimulation (TES) apparatus with control circuitry (e.g. controller) that is adapted for the application of the ensemble waveforms described herein.

For example, a transdermal electrical stimulation (TES) applicator apparatus for modifying a subject's cognitive state may include: a body; a first connector configured to connect to a first electrode; a second connector configured to connect to a second electrode; and a TES controller at least partially within the body and comprising a processor, a timer and a waveform generator, wherein the TES controller is adapted to deliver an ensemble current waveform for application between the first and second connectors, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; further wherein, prior to delivery, the controller is configured to modulate one or more of the component waveforms of the ensemble current waveform by setting the current amplitude to zero at a modulation frequency for a modulation duration that does not result in truncated biphasic pluses in the delivered waveform.

The controller may be configured to modulate one or more of the component waveforms of the ensemble current waveform by setting the current amplitude to zero at a modulation frequency for the modulation duration, wherein the modulation duration is a multiple of an inverse of the component waveform frequency. The controller may be configured to modulate one or more of the component waveforms of the ensemble current waveform by setting the current amplitude to zero at a modulation frequency for the modulation duration, wherein the modulation duration comprises a bursting duty cycle divided by the modulation frequency, further wherein the modulation duration is adjusted to prevent truncation of biphasic pulses in the delivered waveform.

The TES controller may be adapted to deliver the ensemble current waveform for application between the first and second connectors, wherein the ensemble current waveform comprises a series of five or more component waveforms. The TES controller may generally be adapted to deliver an ensemble current waveform by sequentially delivering the component waveforms wherein the amplitude of each, some or any of the component waveforms is between about 3 mA and about 25 mA, wherein the frequency of each component waveform is between about 700 Hz and about 30 kHz, wherein the percent charge imbalance of each component waveform is between about 10% and 100%, and/or wherein the percent duty cycle of each component waveform is between about 20% and 80%.

Any of the apparatuses described herein may include a wireless receiver circuit, the wireless receiver circuit configured to receive an intensity adjustment factor, wherein the TES controller is configured to adjust the ensemble current waveform delivered by the user intensity adjustment factor by scaling one or more of the frequency, percent duty cycle and intensity of the applied ensemble current.

Also described herein are methods and apparatuses for controlling a wearable neurostimulator (or other wearable electrical stimulators) by transmitting control information instructing the wearable neurostimulator to deliver an ensemble waveform having any of the properties described herein. In particular, described herein are methods and apparatuses for transmitting from a controller to a processor of a wearable neurostimulator to cause the neurostimulator to deliver an ensemble waveform. This may generally be achieved by transmitting a series of predefined messages from a controller to the processor of the wearable neurostimulator, where the series of messages includes a first message telling the processor to prepare to receive a number of segments that specify the component waveform properties described above (e.g., segment number, current amplitude, duration, and a state code that defines the direction and/or type of current applied, e.g., positive, negative, capacitive discharge, zero (ground) current, etc.).

The controller may be remote from the wearable neurostimulator, e.g., it may be held by the user or included as part of personal computing device (e.g., smartphone, tablet, smartwatch, wearable electronics, desktop, laptop, etc.), or it may be integrated into the wearable apparatus. For example, a remote controller may communicate wirelessly with the wearable device (e.g., by Bluetooth, UWB, ultrasound, WiFi, near-field electrical communication, or any other wireless modality); the apparatus may be configured for this type of communication and may be paired or otherwise connected to the device. The wearable neurostimulator may be configured to monitor and/or receive transmissions. For example, when wireless transmission is used, the wearable neurostimulator may be adapted to receive and process the transmitted information, and may therefore include wireless transmission circuitry and/or memory for storing this information.

In some variations, the controller is not remote to the processor, but may be part of the same device, and/or connected by one or more transmission lines, e.g., electrical traces, wires, etc. For example, the controller may be part of an integrated electrode assembly and neurostimulator that can be worn by the user. When the controller is remotely located and wirelessly communicates with the neurostimulator apparatus, the communication between the remotely located controller and the processor of the neurostimulator may be one way (e.g., from the remotely located controller to the neurostimulator) or two-way. In general, communication between the two may be specifically encoded (and in some cases may be encrypted), to optimize the speed, power usage and efficiency of the communication between the controller and the processor of the neurostimulator apparatus, to allow the quick and accurate transfer of instructions for stimulation between a controller and a neurostimulator. Although there are numerous ways that these instructions may be encoded and/or processed, described herein are particularly advantageous methods and apparatuses embodying these methods.

For example, a method of controlling a wearable neurostimulator from a control apparatus (either remote or local to the processor of the wearable neurostimulator apparatus) may include: transmitting a first message from the control apparatus instructing the wearable neurostimulator to prepare to receive a new set of waveform parameters or a modification of a stored set of waveform parameters; and transmitting one or more segment messages from the control apparatus, the segment messages defining segments of the new waveform parameters or the modification to the stored waveform parameters, the segment messages each comprising a message encoding: a segment index number, a segment duration, a current amplitude, and a state code, wherein the state code indicates one of: positive current, negative current, capacitive discharge, and open circuit.

In any of these variations, the first message may typically include a message identification code identifying the first message as containing instructions instructing the wearable neurostimulator to prepare to receive the new set of waveform parameters or the modification of the stored waveform parameters. The one or more segment messages may comprise a message identification code identifying them as segment messages.

Transmission of the first message may include transmitting the first message comprising a four byte message. The segment messages may each comprise a seven byte message.

In any of the variations described herein, transmitting the first message and the one or more segment messages may include wirelessly transmitting from the control apparatus to the wearable neurostimulator. Alternatively, transmitting from the first message and the one or more segment messages may include transmitting through a physical connection between the control apparatus and the wearable neurostimulator.

In any of these methods described herein, the method may include pairing or synchronizing the wearable neurostimulator and the remote control apparatus.

In general, in any of these methods, the first message may include one or more of: a code indicating transmission of a new waveform or transmission of a modification of a stored waveform, a number of segments to expect, and an indication that the waveform will be burst modulated.

The control apparatus may transmit at regular intervals, which may be matched with receiving intervals at the neurostimulator. For example, a neurostimulator may transmit the first message and/or the one or more segment messages about every 400 milliseconds. In any of the methods and apparatuses described, a message may not be sent (or a null message sent, or messages not specific to the control of the waveform) at each communication interval (e.g., 400 msec intervals, etc.).

As mentioned above, any appropriate communication protocol may be used; for example, the control apparatus may transmit the first message and the one or more segment messages by Bluetooth.

A method of controlling a wearable neurostimulator from a control apparatus may include: transmitting a first message from the control apparatus instructing the wearable neurostimulator to prepare to receive a new set of waveform parameters or a modification of a stored set of waveform parameters, the first message comprising a four byte message, wherein the first message includes: a code indicating transmission of a new waveform or transmission of a modification of a stored waveform, a number of segments to expect, and an indication whether the waveform will be burst modulated; and transmitting one or more segment messages from the control apparatus, the segment messages defining segments of the new waveform parameters or the modification to the stored waveform parameters, the segment messages each comprising a seven byte message encoding: a segment index number, a segment duration, a current amplitude, and a state code, wherein the state code indicates one of: positive current, negative current, capacitive discharge, and open circuit (zero).

As mentioned above, the first message may include a message identification code identifying the first message as containing instructions instructing the wearable neurostimulator to prepare to receive the new set of waveform parameters or the modification of the stored waveform parameters. The one or more segment messages comprise a message identification code identifying them as segment messages.

Also described herein are apparatuses configured to control a wearable neurostimulator. These apparatuses may include software, firmware or the like for communicating with a wearable neurostimulator. For example, a control may comprise a smartphone, watch, or wearable electronic (glasses, etc.) that can wirelessly communicate with a wearable neurostimulator, and is adapted to run control logic (e.g., software, firmware, etc.) for structuring and controlling communication with a neurostimulator. For example, a control apparatus for controlling a wearable neurostimulator may include a processor, the processor configured to: transmit a first message instructing the wearable neurostimulator to prepare to receive a new set of waveform parameters or a modification of a stored set of waveform parameters, the first message comprising: a code indicating transmission of a new waveform or transmission of a modification of a stored waveform, a number of segments to expect, and an indication whether the waveform will be burst modulated; and transmit one or more segment messages from the control apparatus, the segment messages defining segments of the new waveform parameters or the modification to the stored waveform parameters, the segment messages each encoding: a segment index number, a segment duration, a current amplitude, and a state code, wherein the state code indicates one of: positive current, negative current, capacitive discharge, and open circuit.

As mentioned, the processor may be configured to transmit the first message as a four byte message (message payload), e.g., a first message alerting the neurostimulator processor to prepare to receive and/or modify a component waveform. The four bytes message payload typically including: a code indicating transmission of a new waveform or transmission of a modification of a stored waveform, a number of segments to expect, and an indication whether the waveform will be burst modulated. The message may include additional bytes indicating, for example, the message ID (e.g., a code specifying the type of message), the routing information (destination, source, etc.), The processor may be configured to transmit the one or more segment messages including a seven byte message payload (segment payload). The processor may be configured to transmit the first message to include a message identification code identifying the first message as containing instructions instructing the wearable neurostimulator to prepare to receive the new set of waveform parameters or the modification of the stored waveform parameters. The processor may be configured to transmit the one or more segment messages to each include a message identification code identifying them as segment messages. The processor may be configured to wirelessly transmit the first message and the one or more segment messages on a wireless circuit. The processor may be connected via a physical connection to the wearable neurostimulator, and/or may be integrated into the wearable neurostimulator, so that the processor transmits the first message and the one or more segment messages through the physical connection between the control apparatus and the wearable neurostimulator.

The processor may be configured to wirelessly transmit the first message and the one or more segment messages from the control apparatus. The control apparatus may be configured to transmit the first message and/or the one or more segment messages about every 400 msec or multiples of 400 msec.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1C illustrates one variation of a pair of base waveforms including a first variation of a capacitive discharge.

FIG. 1D illustrates a second variation of a pair of base waveforms including a second variation of capacitive discharge.

FIGS. 2A, 2B and 2C schematically illustrate another example of an ensemble waveform (configured as an 'energy' ensemble waveform) as described herein. FIG. 2A illustrates the current parameter of the ensemble waveform. FIG. 2B schematically indicates the durations of the component waveforms forming the ensemble waveform. FIG. 2C illustrates the frequency parameter of the ensemble waveform.

FIGS. 2D, 2E and 2F schematically illustrate another example of an ensemble waveform (configured as a 'calm' ensemble waveform) as described herein. FIG. 2D illustrates the current parameter of the ensemble waveform. FIG. 2E schematically indicates the durations of the component waveforms forming the ensemble waveform. FIG. 2F illustrates the frequency parameter of the ensemble waveform.

FIGS. 3H-3K illustrates a first example of one variation of an electrode assembly, configured as a "calm" electrode assembly.

FIGS. 3L-3o illustrate a second example of one variation of an electrode assembly, configured as an "energy" electrode assembly.

FIG. 4A is a table with waveform parameters of another example of a calm ensemble waveform.

FIG. 4B is a table with another variation of a calm ensemble waveform.

FIG. 4C is a table with another variation of a calm ensemble waveform.

FIG. 5A is a table listing waveform parameters of another example of an energy ensemble waveform.

FIG. 5B is a table listing waveform parameters of another example of an energy ensemble waveform.

FIG. 6 is a table describing one example of an "add-in" waveform, which may be selected by the user to evoke a predetermined effect, such as enhancing the cognitive effect. In this example, the add-in parameters modify the parameters of the ensemble waveform, for example by adjusting the intensity for a predetermined duration (having 6 component epochs or regions of the add-in, spanning 9.2 seconds). This example adjusts the stimulation intensity down gradually (over 7 seconds or so), then rapidly steps up back to its previous value.

FIG. 7 is a table showing values for one variation of an ensemble waveform that may be used for evoking a calming cognitive effect. This variation is a 10 minute compound or ensemble waveform having 20 component waveforms, where all of the component waveforms are amplitude modulated (e.g., using a square waveform) and each component waveform may be amplitude modulated with different AM frequencies and/or duty cycles.

FIGS. 8A-8D illustrate examples of the amplitude modulation (AM) waveforms that may be applied onto the ensemble waveforms (or component waveforms of the ensemble waveforms described herein). In FIGS. 8A-8D, amplitude modulation square pulses are used as the amplitude modulating waveform (typically having an amplitude of zero or 1, and an instantaneous or near-instantaneous rise/fall time).

FIGS. 10A-10C illustrate an example of amplitude modulation using a sinusoid waveform as the amplitude modulating waveform; FIGS. 10B and 10C illustrate expanded time scale views of the amplitude modulated component waveforms (note the different peak intensities).

FIG. 10D illustrates another example of a sinusoidal amplitude modulation signal that has a non-zero minimum, so that the ensemble (or component waveforms of the ensemble waveform) are dampened to a non-zero level.

FIG. 13 is a table showing one example of the component waveform parameters configured to evoke a calm cognitive state, having a five minute duration. This example is amplitude modulated (at a constant level across all 3 component waveforms). The waveform shape of the AM may be square, sinusoidal, etc.

FIG. 14 is a table showing an example of the component waveform parameters for an ensemble waveform configured to evoke a calm cognitive state, having a six minute duration. In this example the ensemble waveform is amplitude modulated and the amplitude modulation changes (e.g., at each component waveform beginning after the second component waveform).

FIG. 15 is a table showing an example of the component waveform parameters for an ensemble waveform configure to evoke a calm cognitive state, having a ten minute duration. In this example, the amplitude modulation also changes between some of the different component waveforms (e.g., changing AM frequency and/or percent duty cycle).

FIGS. 16A-16E illustrate the principle of correction, adjustment and/or selection of an amplitude modulation signal (e.g., frequency and/or percent duty cycle, also referred to as burst frequency and burst length) for an amplitude modulated component waveform, in order to prevent truncation of component waveforms. FIG. 16A illustrates one example of a component waveform. FIG. 16B illustrates one example of an amplitude modulation envelope waveform. FIG. 16C illustrates truncation of signals from the exemplary component waveform shown in FIG. 16A when amplitude modulated by the AM envelope shown in FIG. 16B. FIG. 16D illustrates a corrected AM envelope in which the AM frequency (the inverse of the amplitude modulation duration) of the envelope signal has been modified to prevent truncation of the component waveform signals, as shown in FIG. 16E.

DETAILED DESCRIPTION

Figure 1A:
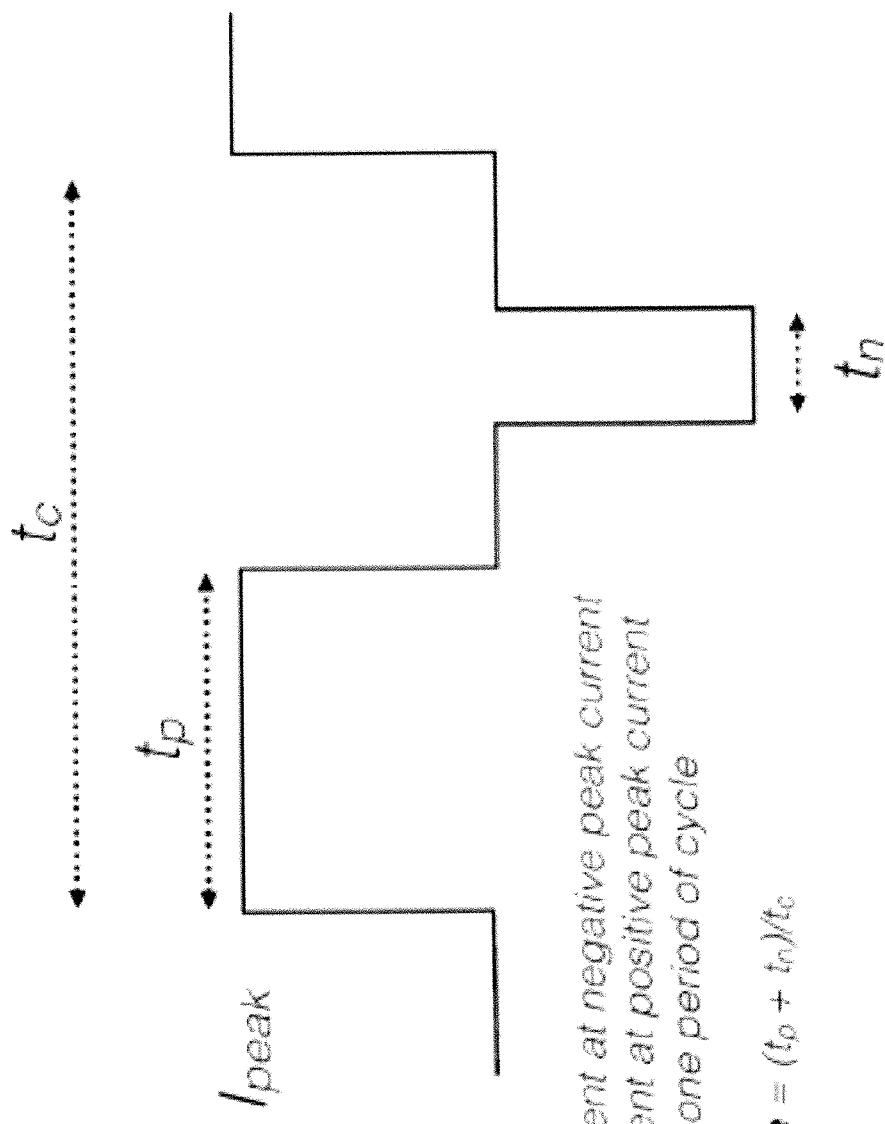
FIG. 1A schematically illustrates a base waveform which may be repeated and modified according to waveform parameters to form component waveforms which may be combined to form ensemble waveforms, as described herein.

Described herein are methods and apparatuses for transdermal electrical stimulation (e.g., neurostimulation) of a subject using ensemble waveforms that generally include a sequence of different periods (component waveforms) having predetermined values (e.g., peak values) for at least four waveform components, in which one or more (typically two) of these waveform components is changed between adjacent component waveforms in the series forming the ensemble waveform. Also described herein are methods of modulating a subject's cognitive state by applying ensemble waveforms, and apparatuses configured to apply these ensemble waveforms. Also described herein are methods and apparatuses (including devices and systems) for user control of ensemble waveforms, particularly transdermal electrical stimulation (TES) ensemble waveforms. In general, the methods and apparatuses may allow effective neuromodulation with electrical stimulation to induce a beneficial or desired change in cognitive function and/or cognitive state. Finally, described herein are methods and apparatuses for controlling a neurostimulator including transmitting waveform information (e.g., component waveform information) to a processor of a wearable neurostimulator where it may be used to set the parameter values necessary to deliver the ensemble waveform as described herein.

In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol. A system may include the wearable neuromodulation device, and the user computing device for control of the transdermal electrical stimulation (TES) waveforms.

A time-varying pattern of electrical stimulation delivered transdermally (and, optionally, to some extent, transcranially) to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g., amplitude modulation at one or more frequencies), pulsed current (e.g., amplitude modulation where part of the modulated cycle is at zero intensity), and more complex time-varying patterns of electrical stimulation (including repeated, random, pseudo-random, and chaotic patterns). In operation, the device may provide current flow at target areas (e.g., in the brain, facial nerves (cranial nerves and/or cervical spinal nerves), vagal nerve, or other neuronal targets) to induce neuromodulation when appropriate electrode configurations and stimulation protocols are delivered.

TES waveform parameters that may be used to invoke, enhance, or modify a variety of cognitive states may be considered compound waveforms including a number of different sub-portions that are temporally connected together and delivered to a user in sequence. In general, the ensemble waveform and the component portions can be defined by four waveform parameters that may be used by the neurostimulator to define the component waveforms and, in combination with the duration of each waveform component and in some variations a ramping parameter, may define an ensemble waveform. In some variations, more complex waveforms are used for TES, and additional components may be included, such as transient capacitive discharges, multiple pulses per cycle, phase relationships of two or more pulses per cycle, complex pulse shapes, non-sinusoidal alternating current, etc. In some variations, an ensemble waveform (or portion of an ensemble waveform) may be modulated by an envelope of slower-frequency amplitude modulation (e.g., modulation of the current amplitude parameter). For example different types of amplitude modulation may be applied (e.g., amplitude modulation at frequencies between 0.5 Hz and 1000 Hz may be applied on top of the ensemble waveform. In some variations the amplitude modulation is applied as a sinusoidal (e.g., pure sinusoid, sawtooth, square pulses, etc.); in some variations the amplitude modulation is bursting, and results in an amplitude modulation duty cycle, in which stimulation intensity is decreased or turned off for a pre-determined period and switched on for a pre-determined period (where the amplitude modulation duty cycle can be calculated as the on period duration divided by the sum of the on period duration and off period duration).

The TES waveform components described herein may generally be formed of a basic unit comprising a plurality of biphasic pulses that may be asymmetric with respect to positive and negative going phases and may be charge imbalanced (although one or more capacitive discharging pulses may also be included within each repeating pulse to offset a charge imbalance as described herein). The component waveforms described herein may be defined by a duration and a set of waveform parameters including: a peak current amplitude (in mA), a frequency (in Hz or kHz), a percent charge imbalance, and a duty cycle. FIG. 1A schematically illustrates a basic waveform unit. This example shows the basic unit as a combination of square-waves (steps), however, rounded (including sinusoid), sawtoothed, triangular, and other shapes may be used. The waveform parameters for this basic unit waveform are defined by a duty cycle (or percent duty cycle), percent charge imbalance (also referred to as percent direct current, or percent DC), ramping or other amplitude modulation, one or more multiple frequency components, phase relationship of biphasic current, flat or structured noise, wave shapes (i.e., sawtooth, triangular, sine wave, square wave, exponential, or other wave shape), capacitance compensation features, or other parameters as discussed in U.S. patent application Ser. No. 14/091,121, titled "Wearable Transdermal Electrical Stimulation Devices and Methods of Using Them", filed on Nov. 26, 2013, which is herein incorporated by reference in its entirety.

In FIG. 1A, the biphasic waveform includes a positive-going pulse having an amplitude $I_{peak}$, and a duration $t_p$ (time spent in the positive direction, relative to baseline), a negative-going pulse having an amplitude (in this example, $I_{peak}$ but in the negative direction) and a duration $t_n$ (time spent in the negative direction, relative to baseline). The total time of the base unit is $t_c$ (time for one period of a cycle).

As used herein, 'percent duty cycle' may refer to the proportion of a cycle of a waveform that causes non-zero (or nominally non-zero) current to be delivered transdermally (though for waveforms incorporating capacitive discharge, the nominally non-zero portion of the duty cycle may not include the non-zero portions of the cycle caused by capacitive discharge). For example, the duty cycle in FIG. 1A is the sum of $t_p$ and $t_n$ divided by $t_c$. Further, the percent charge imbalance (or 'percent direct current') refers to the non-zero portion of a waveform cycle that is positive-going or negative-going (again, excluding capacitive discharges, if present). In FIG. 1A, the percent charge imbalance is the ratio of the difference of $t_p$ and $t_n$ and the sum of $t_p$ plus $t_n$.

Inducing significant, robust, and/or reliable cognitive effects typically requires an appropriate ensemble waveform defined by a set of parameters for each component waveform. A stimulation protocol typically includes a composite waveform that defines the temporal pattern of current delivered to an anode-cathode set and can incorporate one or more waveform components including but not limited to: direct current, alternating current, pulsed current, linear current ramp, non-linear current ramp, exponential current ramp, modulation of current, and more complex patterns (including repeated, random, pseudo-random, and chaotic patterns). In operation, the device may provide current flow at target areas (e.g., in facial nerves, cranial nerves, vagal nerve, in the brain, etc.) to induce neuromodulation when appropriate electrode configurations and stimulation protocols are delivered.

Although the apparatuses and methods described herein may be used to provide TES to induce and/or modify a variety of cognitive states, two particular examples are described in detail herein: (1) enhancing attention, alertness, or mental focus and (2) inducing a calm or relaxed mental state. Configurations of apparatuses and methods for causing neuromodulation that specifically achieve enhanced attention, alertness, or mental focus as opposed to an increased calm or relaxed mental state are described in particular detail.

Thus, a generic neurostimulator for modifying a cognitive state may include a pair of electrodes (or two sets of electrodes), referred to herein for convenience as an anode and a cathode (where the anode and cathode may loosely refer to their function as primarily anode and primarily cathode for biphasic waveform components), that can be applied to specific regions of the subject's body and used to provide TES stimulation within the relatively high-intensity, high-frequency ranges described as effective herein. Current is typically applied between the anode and cathode electrodes (or groups of anode and cathode electrodes). Without being bound by a particular theory of operation, the current may be passed through the body between the anode and cathode electrodes (or groups of anode and cathode electrodes), potentially applying energy in an appropriate treatment regime to underlying neural tissue (nerves, e.g., cranial, cervical spinal, vagal, etc., brain, etc.) in a particular neural pathway to result in the desired target effect (e.g., attention, alertness, or mental focus; inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus may include a first electrode applied to the subject near the temple and/or forehead area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity stimulation (as described in greater detail below) of this region may result in enhanced attention, alertness, or mental focus.

Another configuration of electrode positions may include an electrode positioned on the subject's skin near the subject's temple and/or forehead area (e.g., above and to the right of the right eye) and a second electrode on the subject's neck (e.g., on a superior portion of the neck centered at or near the midline and at least partially overlapping the midline). Appropriate TES stimulation of this region may result in enhancing a calm or relaxed mental state. Either of these configurations may also be used with an appropriate TES stimulation regime (waveform) to induce phosphenes by noninvasive transdermal electrical stimulation using the apparatuses described herein.

Generally speaking, peak stimulation intensities above at least 3 mA (e.g., greater than 5 mA, e.g., between 5 mA and 25 mA, etc.) may be advantageous for transdermal electrical stimulation that causes neuromodulation by targeting the brain, nerves (e.g., cranial nerves, vagal nerve, peripheral nerves, spinal nerves), and/or spinal cord. To achieve these peak intensities without causing significant pain, irritation, or discomfort in a subject may require appropriate electrodes and appropriate ensemble waveforms as described herein. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g., transdermally). Although there may be variations (optimizations) of these waveforms and electrical protocols for each configuration (electrode placement) and each target cognitive state, in general, the patterns may be within the same range of values to provide biphasic, high-intensity, high-frequency and asymmetric with regard to the positive-going and negative-going phases of the waveform (in some cases not charge balanced) signals that are applied to robustly evoke a response in most individuals while causing at most a low level (e.g., minimal or none) of discomfort and/or pain.

These waveforms may be ensemble waveforms including a plurality (e.g., 3 or more) of component waveforms having a predetermined value for each of: current amplitude ("intensity"), frequency, percent charge imbalance, duty cycle, and in some variations capacitive discharge. These component waveforms may each have a duration (time), and may be connected together in a sequence to evoke the desired cognitive effect. Some of these component waveforms forming the ensemble waveform are ramps, in which one or more waveform parameter (current amplitude, frequency, duty cycle, percent charge imbalance) of the waveform is ramped up to the target/peak value of the waveform components from the previous value of the waveform components after transitioning to the new component waveform when delivering the ensemble waveform.

Generally, tDCS studies have used between about 1 mA and about 2 mA peak currents for longer stimulation periods (e.g., more than a few minutes or seconds), and tACS typically uses relatively low frequencies (e.g., <650 Hz). However, these current levels and frequencies are sub-threshold for at least some forms of neuromodulation. In particular, the inventors have found that higher currents may be necessary for inducing significant and beneficial cognitive effects. Unfortunately, such higher currents may lead to pain, irritation, and damage to skin under high current stimulation conditions. Higher currents than have traditionally been used for TES are required for inducing a change in a cognitive state in at least some instances. Described herein are systems configured to deliver higher currents (optimally 3 mA or higher), at relatively high frequency (>750 Hz, e.g., between 750 Hz and 30 kHz, between 1 kHz and 30 kHz, etc.) to achieve a desired cognitive effect. The ensemble waveforms described herein may reduce irritation, pain, and burning sensations in the dermis, muscles, and other tissues of users receiving TES. These embodiments permit higher current intensities to be transmitted comfortably so that desirable changes in a subject's cognitive function, cognitive state, mood, and/or energy levels can be attained. In addition to the high current amplitudes, high frequency (e.g., repeating the base waveform of FIG. 1A between about 650 Hz and about 50 kHz (e.g., between about 750 Hz and about 40 kHz, between about 1 kHz and about 35 kHz, etc.) may provide biphasic pulsed and/or alternating current stimulation that minimally activates sensory pathways and minimizes pH changes in tissue due to stimulation.

In addition to the waveform parameters described herein, it may be helpful to achieve higher transdermal currents while minimizing pain and irritation by using electrodes that distribute current evenly across the electrode and/or mitigate pH changes known to occur in tissue due to direct current stimulation or other charge imbalanced stimulation waveforms. Embodiments include TES systems and methods that use appropriate electrodes configured to reduce pain, irritation, itching, and burning sensations in a subject due to one or more of: mitigation of pH changes in tissue due to direct current stimulation or charge imbalanced stimulation; hydrogels or other electrically conductive media for more effectively coupling an electrode to a user's skin with low impedance; and components of an electrode assembly that achieve a more even distribution of current across the face of the dermally coupled electrode. Examples of electrode designs that may be used are provided herein, but additional examples may include Axelgaard Manufacturing Co., LTD., Axelgaard Little PALS (neonatal pediatric ECG electrodes) and PALS Platinum Blue (conductive cloth neurostimulation electrodes designed for peripheral transcutaneous electrical nerve stimulation (TENS) and muscle stimulation), which are particularly effective for delivering higher tDCS currents while minimizing pain, irritation, and tissue damage. Electrodes configured to spread current evenly across the face of the electrode and mitigate pH changes due to direct current stimulation and/or charge imbalanced stimulation are advantageous for safely and comfortably delivering higher current intensities (e.g., direct currents above about 1.5 mA) that would otherwise be painful, irritating, or damaging to a subject. One skilled in the art will recognize that other commercially available and custom-designed electrodes that mitigate pH changes in tissue and/or spread current evenly across the electrode surface in dermal contact are advantageous for high current TES.

The waveforms described herein may minimize pain and irritation by delivering ensemble waveforms in which one or more of the waveform parameters (current intensity, frequency, duty cycle and percent charge imbalance) is varied and/or changed and held fixed or ramped for predetermined time intervals as the ensemble waveform progresses. The duration of each component waveform may be between 100 ms and 30 minutes (e.g., 20 min), e.g., between 1 second and 240 seconds and an ensemble waveform may include a gradual ramping of the one (or more than one) parameter being changed between component waveforms, with intermittent periods of stable current delivery (which may habituate a subject to the current level delivered and accordingly reduce or eliminate perceptions of pain and/or irritation due to electrical stimulation, though these static waveforms may also cause habituation to the induced cognitive effect intended from the waveform). Ramping strategies that deliver component portions of the TES waveforms with gradually changing current amplitude, frequency, duty cycle and/or percent charge imbalance can cause habituation or otherwise inhibit a user's sensory receptors or other components of a user's nervous system that transmit painful stimuli or transduce the subjective feeling of pain or discomfort, allowing relatively higher intensities of current (previously considered just to be a function of current amplitude, rather than the timecourse of the stimulation waveform).

For example, pain and irritation from TES may be reduced by ramping the changing waveform parameter gradually (e.g., over tens of seconds to a few minutes) up or down. This can be done various ways: e.g., with a linear ramp, a ramp with a different temporal profile, or a series of ramps between intermediate levels of static current delivery (e.g., ramp and hold, ramp and hold, etc.).

Figure 1B:
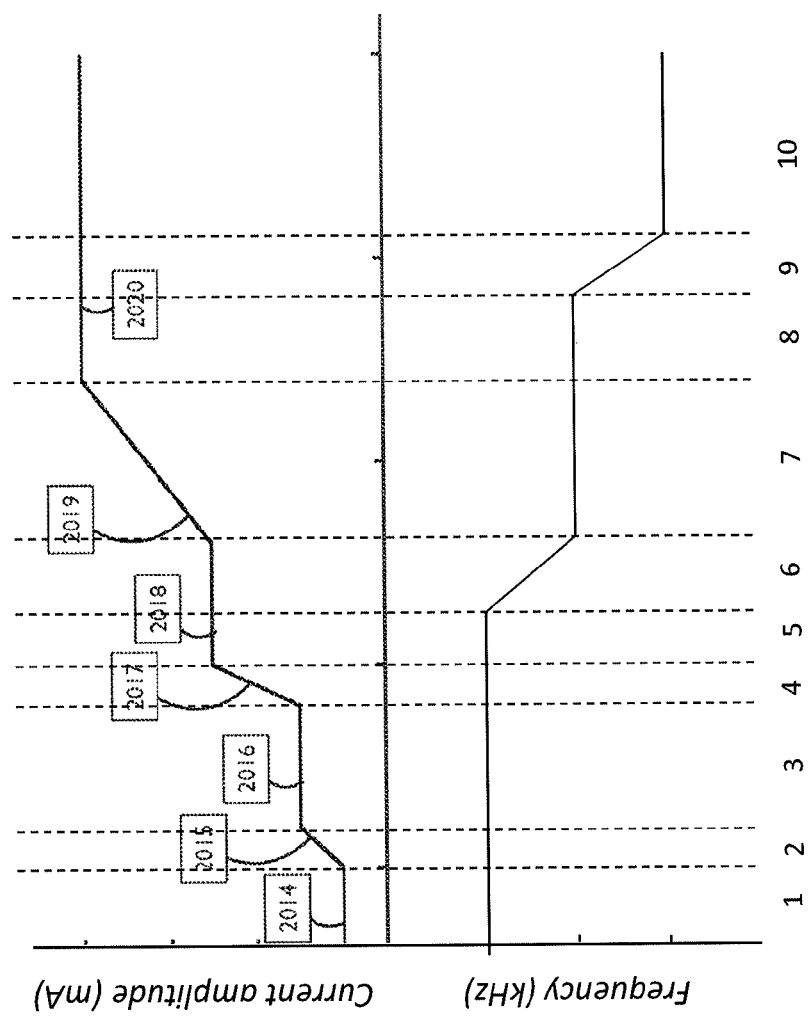
FIG. 1B illustrates one variation of an ensemble waveform, graphically depicted to show the current amplitude and frequency waveform components (but not percent charge imbalance or duty cycle).

As an illustrative example, a TES system configured for applying an ensemble waveform according to a protocol to minimize pain and irritation while evoking a robust response in a subject is illustrated in FIG. 1B. In this example, there are ten waveform components shown (time is on the x-axis, not shown to scale). The first component waveform has a zero current amplitude 2014, but a first frequency (e.g., 10 kHz), and duty cycle (e.g., 40%), and percent charge imbalance (e.g., 80%). Thus, once the ensemble waveform is applied, there is initially no current (since current is 0 mA). After a few seconds duration, the second component waveform starts 2015. The second component waveform has a value for the peak current amplitude (e.g., 5 mA), a frequency (e.g., 10 kHz, in this example, the same as the first component waveform), a percent charge imbalance (e.g., 80%, in this example, the same as the first component waveform), and a percent duty cycle (e.g., 40%, in this example, also the same as the first component waveform). This second component waveform also has a predetermined duration (e.g., 1 min), and ramping is on, so that the parameter that changes from the first component waveform (amplitude) is ramped over the 1 minute duration to the peak value. In some variations the waveform components may indicate which parameters (amplitude, frequency, etc.) are to be ramped and/or a separate duration and/or a method of ramping for each of the waveform components that has changed. The third component waveform 2016 has all of the same waveform parameters as the second, but with ramping off (or ramping time set to zero) and a duration of about 3 minutes. The fourth component waveform 2017 has ramping on again, a duration of one minute, and an increase in the peak current amplitude (e.g., 10 mA). The fifth component waveform 2018 has the same waveform parameter values as the fourth, but with ramping off, maintaining the waveform parameters for several minutes until the sixth component 2019, in which the frequency is increased (e.g., to 15 kHz) and ramping is on. The seventh component waveform 2020 increases the current value (e.g., to 12 mA), while keeping the frequency and other waveform parameters the same, with ramping on for the duration of the component (e.g., 5 min). The 8th component waveform 2020 has the same waveform parameters, but with ramping off for the duration (e.g., 2 min). The 9th component waveform has an increase in the frequency (e.g., to 17 kHz) and ramping on, while all other parameters stay the same. The 10th component waveform has all the same waveform parameters as the 9th, but with ramping off. Also not shown in this example, a capacitive discharge may be "on" during all of the component waveforms (or some of them).

This example shows primarily increasing current and frequency, however, any of the other components may be modified (e.g., duty cycle, percent current imbalance), or decreased as well as increased.

In any of the ensemble waveforms described herein, a capacitive discharge may be incorporated into any or all of the composite waveforms. As used herein, a capacitive discharge may be referred to as a controlled transient short circuiting of the electrodes at some point (or more than one point) during the pulsing waveform (e.g., every cycle, after every pulse, etc.). Capacitive discharge may be a beneficial feature for TES waveforms, because it may relieve capacitance built up in the subject's body (and electrodes coupled to the subject's skin) that can lead to pH changes and discomfort. Reducing capacitance in the subject's body also may improve the efficiency of stimulation by decreasing the voltage required for delivering a current (i.e., a high current such as one greater than 5 mA) transdermally. For example, FIGS. 1C and 1D illustrate two kinds or types of capacitive discharge that may be used. In FIG. 1C the basic waveform unit, such as the one shown and described above in FIG. 1A, includes a pair of capacitive discharges that occur following each positive-going or negative-going pulse. In some variations, e.g., the "calm" ensemble waveforms described herein, a capacitive discharge occurs at the end of the positive-going pulse and at the end of the negative-going pulse. The time constant for the return of the capacitive discharge may be sufficiently long so that the adjacent negative-going pulse rides on the return portion of the capacitive discharge, as shown in FIG. 1C. In some variations, such as the "energy" ensemble waveforms described herein, the capacitive discharge may occur at the start of a pulse. For example, in FIG. 1D, each base unit includes at least one capacitive pulse that occurs at the start of the negative-going pulse. These examples are not meant to be limiting with regard to the types of capacitive discharge that may be used in component waveforms for TES. Thus, in general, any of the ensemble waveforms may also include a parameter (e.g., an overall parameter and/or an individual parameter for each composite waveform) indicating if a capacitive pulse (or pulses) is included. In some variations, the capacitive pulse parameter may also indicate the type of capacitive pulse (e.g., positive-going, negative-going). The capacitive pulse parameter may also indicate the timing of a capacitive discharge during a cycle (i.e., relative to pulses or other features of the waveform, including after each positive-going pulse, after each negative-going pulse, before each positive-going pulse, before each negative-going pulse, etc.). The capacitive pulse parameter may also indicate the time constant for the capacitive pulse parameter and/or it may be set by the system. The capacitive pulse parameter may also indicate the number of capacitive discharges during a cycle (including values less than one, i.e., those that occur on every other cycle; every 3$^{rd}$ cycle; every 4$^{th}$ cycle; every n$^{th}$ cycle, etc.; and also including capacitive discharge that occurs on cycles selected randomly or pseudo-randomly). The capacitive pulse parameter may also indicate the maximum current (and/or maximum voltage) of the capacitive discharge, which is defined by elements of the electric circuit of the neurostimulator device configured for allowing the capacitive discharge to occur.

These ensemble waveforms may be delivered to the subject wearing the neurostimulator, or in some variations they may be modified (e.g., by scaling them down) as mentioned above. Scaling or otherwise modifying a waveform may be controlled in real-time or near-real-time by the user (subject) during a TES session, for instance as discomfort develops or to increase the strength of an intended cognitive effect. Scaling will typically change (e.g., by a percentage) one or more of the waveform parameters (e.g., current amplitude, frequency, duty cycle, charge imbalance, etc.). When a subject modifies a waveform to reduce discomfort (e.g., by one or more of: reducing current amplitude, increasing frequency, decreasing duty cycle, decreasing charge imbalance), the modified waveform may allow habituation to the current delivered so that the subject experiences reduced irritation or discomfort.

Biphasic transcranial alternating current stimulation (and biphasic pulsed current stimulation as shown in FIGS. 1A, 1C, and 1D) may yield stronger cognitive effects compared to transcranial direct current stimulation due to dramatically reducing discomfort in the skin under the electrodes (and, in at least some cases, enabling higher peak stimulation currents). Putative mechanisms for reduced irritation include: (1) reduced pH changes in tissue relative to pH changes occurring from direct current stimulation; and (2) reduced skin impedance at higher stimulation frequencies.

Another example of a composite waveform that may be used as described herein is shown in FIGS. 2A-2C. FIG. 2A shows the peak intensity for each of the component waveforms forming the ensemble waveform. This waveform may be used to evoke a cognitive state referred to herein as a "calm" ensemble waveform (e.g., for evoking a feeling of calm when applied with electrodes positioned at the temple (and/or forehead) and back of the neck). FIG. 2B shows labels for the component waveforms indicating their order, duration, and timing. FIG. 2C shows the carrier frequency of stimulation for each of the component waveforms. For all waveform segments shown, the peak intensity listed is the maximum peak intensity, which may be delivered at a reduced level (i.e., percentage of the peak intensity) based on automatic or manual (user-controlled) intensity selection, as mentioned above. Also, this example shows that not all waveform parameters need to change during an ensemble waveform. In this example, the duty cycle is fixed at 40% for all component waveforms.

The waveform begins with component waveform 100 during which stimulation is turned on gradually to improve the comfort of the experience for the user and thus increase the likelihood that a cognitive effect can be induced without causing undue discomfort, pain, or tissue damage. Similarly, at the end of the waveform, component waveform 116 gradually ramps down the intensity of stimulation gradually as the ensemble waveform completes. In the intervening time period, the ensemble waveform comprises three primary waveform components, as well as waveform components that provide transition periods between the primary waveform components.

A first primary waveform component ('primary waveform component X') 101, 107, 115 is defined by a maximum peak intensity of 8 mA, 40% duty cycle, 40% charge imbalance, and 5 kHz carrier frequency.

A second primary waveform component ('primary waveform component Y') 103, 109, 113 is defined by a maximum peak intensity of 17 mA, 40% duty cycle, 45% charge imbalance, and 12 kHz carrier frequency.

A third primary waveform component ('primary waveform component Z') 105, 111 is defined by a maximum peak intensity of 20 mA, 40% duty cycle, 55% charge imbalance, and 18 kHz carrier frequency.

In this example, the waveform parameters for the component waveforms making up this ensemble waveform are shown, in order, in Table 1, below:

TABLE 1

| First ensemble waveform example | | | | | | | | | | |
|---|---|---|---|---|---|---|---|---|---|---|
| FIGS. 2A-C label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
| 100 | 0 | 30 | 0 | 8 | 40 | 40 | 40 | 40 | 5 | 5 |
| 101 | 30 | 90 | 8 | 8 | 40 | 40 | 40 | 40 | 5 | 5 |
| 102 | 120 | 15 | 8 | 17 | 40 | 40 | 40 | 45 | 5 | 12 |

TABLE 1-continued

First ensemble waveform example

| FIGS. 2A-C label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
|---|---|---|---|---|---|---|---|---|---|---|
| 103 | 135 | 75 | 17 | 17 | 40 | 40 | 45 | 45 | 12 | 12 |
| 104 | 210 | 15 | 17 | 20 | 40 | 40 | 45 | 55 | 12 | 18 |
| 105 | 225 | 75 | 20 | 20 | 40 | 40 | 55 | 55 | 18 | 18 |
| 106 | 300 | 15 | 20 | 8 | 40 | 40 | 55 | 40 | 18 | 5 |
| 107 | 315 | 75 | 8 | 8 | 40 | 40 | 40 | 40 | 5 | 5 |
| 108 | 390 | 15 | 8 | 17 | 40 | 40 | 40 | 45 | 5 | 12 |
| 109 | 405 | 75 | 17 | 17 | 40 | 40 | 45 | 45 | 12 | 12 |
| 110 | 480 | 15 | 17 | 20 | 40 | 40 | 45 | 55 | 12 | 18 |
| 111 | 495 | 75 | 20 | 20 | 40 | 40 | 55 | 55 | 18 | 18 |
| 112 | 570 | 15 | 20 | 17 | 40 | 40 | 55 | 45 | 18 | 12 |
| 113 | 585 | 75 | 17 | 17 | 40 | 40 | 45 | 45 | 12 | 12 |
| 114 | 660 | 15 | 17 | 8 | 40 | 40 | 45 | 40 | 12 | 5 |
| 115 | 675 | 90 | 8 | 8 | 40 | 40 | 40 | 40 | 5 | 5 |
| 116 | 765 | 30 | 8 | 0 | 40 | 40 | 40 | 40 | 5 | 5 |

In the exemplary waveform of FIG. 2A, the first component waveform has a 30 second ramp phase 100 from 0 to 8 mA with primary waveform component X. The second component waveform is a 90 second maintenance component waveform 101 with primary waveform component X at 8 mA maximum peak intensity. The third component waveform is a 15 second ramp phase 102 that gradually changes the peak intensity, percent charge imbalance, and carrier frequency between primary waveform component X and primary waveform component Y. The fourth component waveform is a 75 second maintenance component waveform 103 with primary waveform component Y at 17 mA maximum peak intensity. The fifth component waveform is a 15 second ramp phase 104 that gradually changes the peak intensity, percent charge imbalance, and carrier frequency between primary waveform component Y and primary waveform component Z. The sixth component waveform is a 75 second maintenance component waveform 105 with primary waveform component Z at 20 mA maximum peak intensity. The seventh component waveform is a 15 second ramp phase 106 that gradually changes the peak intensity, percent charge imbalance, and carrier frequency between primary waveform component Z and primary waveform component X. The eighth component waveform is a 75 second maintenance component waveform 107 with primary waveform component X at 8 mA maximum peak intensity. The ninth component waveform is a 15 second ramp phase 108 that gradually changes the peak intensity, percent charge imbalance, and carrier frequency between primary waveform component X and primary waveform component Y. The 10th component waveform is a 75 second maintenance component waveform 109 with primary waveform component Y at 17 mA maximum peak intensity. The 11th component waveform is a 15 second ramp phase 110 that gradually changes the peak intensity, percent charge imbalance, and carrier frequency between primary waveform component Y and primary waveform component Z. The 12th component waveform is a 75 second maintenance component waveform 111 with primary waveform component Z at 20 mA maximum peak intensity. The 13th component waveform is a 15 second ramp phase 112 that gradually changes the peak intensity, percent charge imbalance, and carrier frequency between primary waveform component Z and primary waveform component Y. The 14th component waveform is a 75 second maintenance component waveform 113 with primary waveform component Y at 17 mA maximum peak intensity. The 15th component waveform is a 15 second ramp phase 114 that gradually changes the peak intensity, percent charge imbalance, and carrier frequency between primary waveform component Y and primary waveform component X. The 16th component waveform is a 90 second maintenance component waveform 115 with primary waveform component X at 8 mA maximum peak intensity The final, $17^{th}$, component waveform is a 30 second ramp phase 116 from 8 to 0 mA with primary waveform component X.

FIGS. 2D-2F illustrate another example of an ensemble waveform that may be particularly effective as an "energy" waveform (inducing or enhancing focus and attention, enhancing alertness, enhancing wakefulness, increasing subjective feeling of energy, etc.), with electrodes positioned on the temple (and/or forehead) and mastoid region. For example, FIGS. 2D, 2E, and 2F schematically illustrate the ensemble waveform, which is composed of 15 component waveforms, of which several are repeating (i.e., have identical waveform parameters and duration), with a composite duration of 417 seconds. This ensemble waveform also includes a number of rapid transitions.

For example, FIG. 2D shows the peak intensity for each of the component waveforms, FIG. 2E shows labels for the component waveforms indicating their order, duration, and timing, and FIG. 2F shows the carrier frequency of stimulation for each of the component waveforms. The long period of the ensemble waveform at the 11 kHz frequency 215 is the frequency for all component waveform segments 200-211. Table 2, below, illustrates the waveform parameters for the individual component waveforms, in order, making up this ensemble waveform:

TABLE 2 second Ensemble waveform example

| FIGS. 2D-F label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
|---|---|---|---|---|---|---|---|---|---|---|
| 200 | 0 | 30 | 0 | 16 | 41 | 41 | 85 | 85 | 11 | 11 |
| 201 | 30 | 30 | 16 | 18 | 41 | 41 | 85 | 85 | 11 | 11 |
| 202 | 60 | 60 | 18 | 18 | 41 | 41 | 85 | 85 | 11 | 11 |
| 203 | 120 | 2 | 18 | 11 | 41 | 41 | 85 | 85 | 11 | 11 |
| 204 | 122 | 3 | 11 | 18 | 41 | 41 | 85 | 85 | 11 | 11 |
| 205 | 125 | 60 | 18 | 18 | 41 | 41 | 85 | 85 | 11 | 11 |
| 206 | 185 | 2 | 18 | 11 | 41 | 41 | 85 | 85 | 11 | 11 |
| 207 | 187 | 3 | 11 | 18 | 41 | 41 | 85 | 85 | 11 | 11 |
| 208 | 190 | 90 | 18 | 18 | 41 | 41 | 85 | 85 | 11 | 11 |
| 209 | 280 | 2 | 18 | 11 | 41 | 41 | 85 | 85 | 11 | 11 |
| 210 | 282 | 15 | 11 | 18 | 41 | 41 | 85 | 85 | 11 | 11 |
| 211 | 297 | 30 | 18 | 18 | 41 | 41 | 85 | 85 | 11 | 11 |
| 212 | 327 | 15 | 18 | 11 | 41 | 38 | 85 | 100 | 11 | 7.5 |
| 213 | 342 | 60 | 11 | 11 | 38 | 38 | 100 | 100 | 7.5 | 6.7 |
| 214 | 402 | 15 | 11 | 0 | 38 | 38 | 100 | 100 | 6.7 | 6.7 |

In the example shown in FIGS. 2D-2F, as in FIGS. 2A-2C, the current amplitude shown is a peak current amplitude or maximum peak intensity, which may be delivered at a reduced level (i.e., percentage) based on automatic or manual (user-controlled) adjustment of the perceived intensity.

In this example, the ensemble waveform begins with component waveforms 200, 201 during which stimulation is turned on gradually to improve the comfort of the experience for the user and thus increase the likelihood that a cognitive effect can be induced without causing undue discomfort. Similarly, at the end of the ensemble waveform, component waveform 214 gradually ramps down the intensity of stimulation as the ensemble waveform completes. In the intervening time period, the ensemble waveform comprises four primary waveform components, as well as waveform components that provide transition periods between the primary waveform components.

In this example, a first primary waveform component ('primary waveform component T') 202, 205, 208, 211 is defined by a maximum peak intensity of 18 mA, 41% duty cycle, 85% charge imbalance, and 11 kHz carrier frequency. A second primary waveform component ('primary waveform component U') is defined by a maximum peak intensity of 11 mA, 41% duty cycle, 85% charge imbalance, and 11 kHz carrier frequency. A third primary waveform component ('primary waveform component V') is defined by a maximum peak intensity of 11 mA, 38% duty cycle, 100% charge imbalance, and 7.5 kHz carrier frequency. A fourth primary waveform component ('primary waveform component W') 213 is defined by a maximum peak intensity of 11 mA, 38% duty cycle, 100% charge imbalance, and 6.7 kHz carrier frequency.

As described in Table 2, above, the ensemble waveform is composed of 15 component waveforms each having a set of waveform parameters that differ from the immediately preceding set of waveform parameters in one or more of the frequency, peak current amplitude, percent duty cycle, or percent charge imbalance. For example, the first component waveform is a 30 second ramp phase 200 from 0 to 16 mA with primary waveform component T. The second component waveform is a 30 second ramp phase 201 from 16 to 18 mA with primary waveform component T. The third component waveform is a 60 second maintenance component waveform 202 with primary waveform component T at 18 mA maximum peak intensity. The fourth component waveform is a 2 second ramp phase 203 that rapidly changes the peak intensity between primary waveform component T and primary waveform component U. The fifth component waveform is a 3 second ramp phase 204 that rapidly changes the peak intensity between primary waveform component U and primary waveform component T. The sixth component waveform is a 60 second maintenance component waveform 205 with primary waveform component T at 18 mA maximum peak intensity. The seventh component waveform is a 2 second ramp phase 206 that rapidly changes the peak intensity between primary waveform component T and primary waveform component U. The eighth component waveform is a 3 second ramp phase 207 that rapidly changes the peak intensity between primary waveform component U and primary waveform component T. The ninth component waveform is a 90 second maintenance component waveform 208 with primary waveform component T at 18 mA maximum peak intensity. The $10^{th}$ component waveform is a 2 second ramp phase 209 that rapidly changes the peak intensity between primary waveform component T and primary waveform component U. The $11^{th}$ component waveform is a 15 second ramp phase 210 that gradually changes the peak intensity between primary waveform component U and primary waveform component T. The $12^{th}$ component waveform is a 30 second maintenance component waveform 211 with primary waveform component T at 18 mA maximum peak intensity. The $13^{th}$ component waveform is a 15 second ramp phase 212 that gradually changes the peak intensity, percent duty cycle, percent charge imbalance, and carrier frequency between primary waveform component T and primary waveform component V. The $14^{th}$ component waveform is a 60 second ramp phase 213 that gradually changes the carrier frequency between primary waveform component V and primary waveform component W; and the $15^{th}$ component waveform is a 15 second ramp phase 214 from 11 to 0 mA with primary waveform component W.

System Description

Figure 3A:
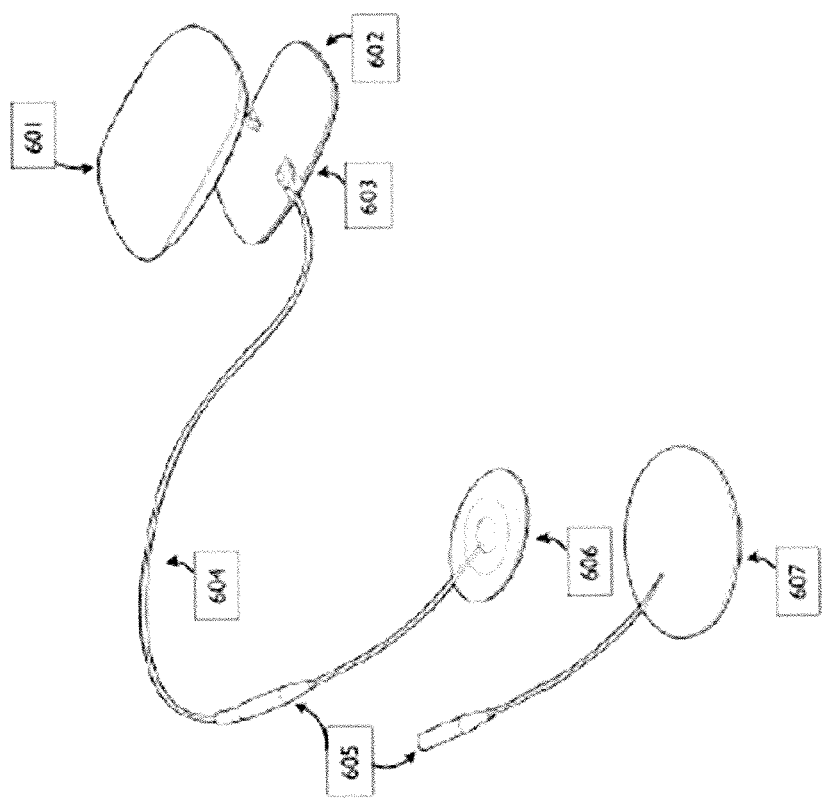
FIG. 3A illustrates one example of a neurostimulator that may be configured for use with (and may deliver) the ensemble waveforms described herein.
Figure 3F:
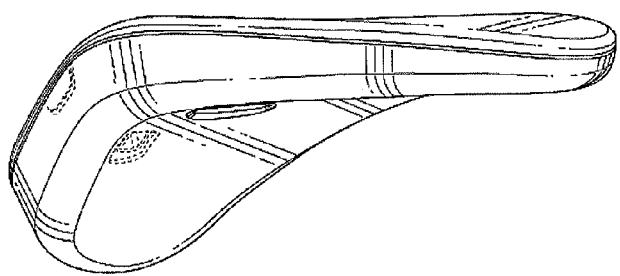
FIGS. 3B-3G illustrate another example of a neurostimulator as described herein.
Figure 3E:
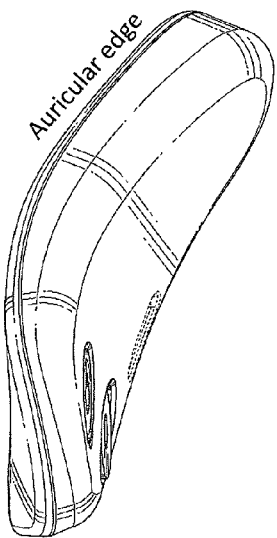
Figure 3D:
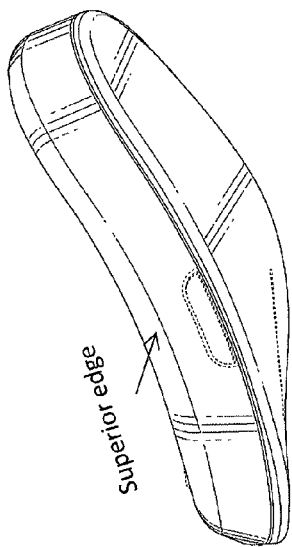
Figure 3G:
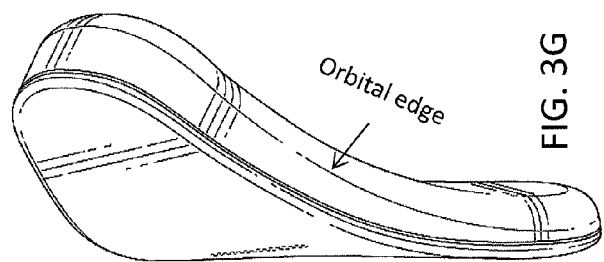
Figure 3B:
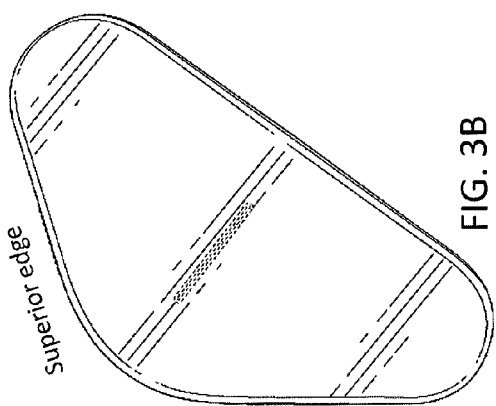
Figure 3C:
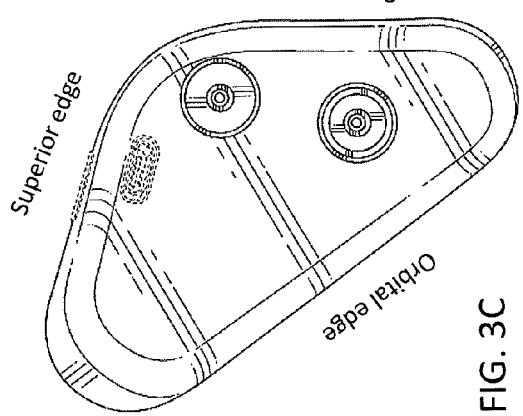
Figure 3Q:
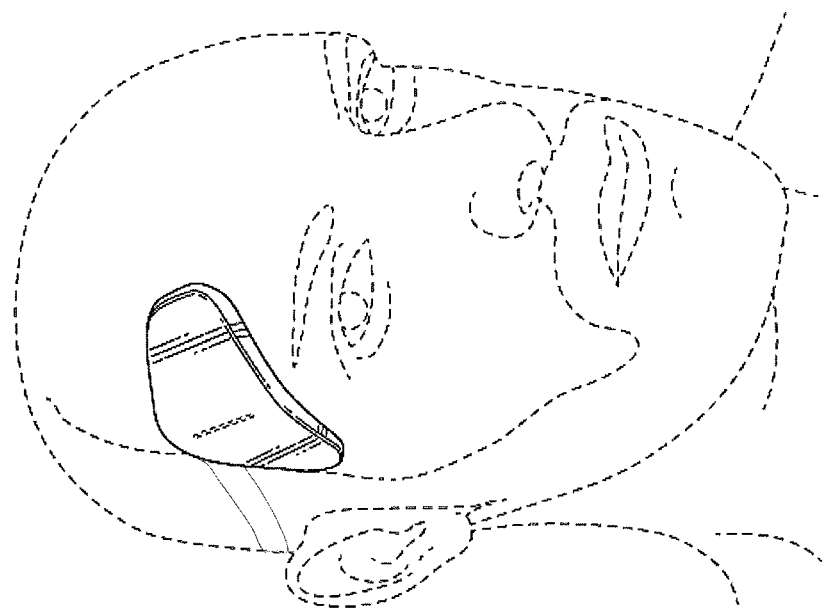
FIG. 3Q illustrates the neurostimulator device worn on the subject's head.

In general, any appropriate neurostimulation system may use (and/or be configured to use or operate with) the ensemble waveforms as described herein. FIGS. 3A-3Q describe and illustrate an example of a neurostimulation system (neurostimulator, electrodes, controller) that may be used. For example, a neurostimulation system may include a lightweight, wearable, neurostimulator device (neurostimulator) that is configured to be worn on the head and a consumable/ disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver the ensemble waveforms as described herein. For example, the user device may present a list of ensemble waveforms and allow the user to select among them in order to select a desired cognitive effect. The ensemble waveforms may be ordered by the desired effect (e.g., calm, energy, etc.) and/or by time and/or by ranking, etc. Further, the user device may be adapted to communicate with the wearable neurostimulator and may transmit an identifier of the selected ensemble waveform, and/or waveform parameters that define all of a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device maybe configured to send, and the neurostimulator to receive, the ensemble waveform parameters (duration, ramping parameter/ramping time, capacitive discharge parameters, current amplitude, frequency, percent duty cycle, percent charge imbalance, etc.).

The user device may also be referred to herein as a controller, and the controller (user device or user computing device) is typically separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smart watch, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e., by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein. The controller may be a component of the neurostimulator apparatus itself.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; an increase psychophysiological arousal associated with changes in the activity of the hypothalamic-pituitary-adrenal axis and/or the reticular activating system; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; maintaining a state of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heart beat.

For example, to induce energy, the electrode apparatus may be attached to the user's temple (and/or forehead) and behind the user's ear (e.g., mastoid region). To induce calm, the electrodes may be attached to the user's temple (and/or forehead) and the back of the user's neck. In both examples, the neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 3 mA and 22 mA, etc.), and a frequency of >700 Hz (e.g., between 700 Hz and 25 kHz, between 700 Hz and 20 kHz, between 700 Hz and 15 kHz, etc.), the current is typically biphasic and is charge imbalanced, and has a duty cycle of between 10-99% (e.g., between 20-95%, between 30-80%, between 30-60%, etc.). One or more of these characteristics may be changed during stimulation over timescales of every few seconds to minutes as the ensemble waveform shifts between subsequent component waveforms.

When worn, the system may resemble the system shown in FIG. 3Q, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g., enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind' of electrode it is (i.e., for the calm or the energy mode; or indicating the batch and/or source of manufacture, etc.). FIGS. 3A and 3B-3G illustrate two variations of a neurostimulator.

For example, FIG. 3A illustrates a first example of a neurostimulator as described herein. In FIG. 3A, the neurostimulator is shown with a pair of electrodes attached. A first electrode 601 is coupled directly to the body 603 of the TES applicator 602, and a second electrode 606 is connected by a cable or wire 604 to the body 603 of the applicator 602. These electrodes are separate from each other, and may be replaceable/disposable. Different shaped electrodes 607 may be used with the same re-usable neurostimulator. The neurostimulator in this example includes a rigid outer body, to which the pair of electrodes is attachable, making electrical contact via one or more plug-type connectors.

FIGS. 3B-3G illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 3B-3G illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 3B-3G the various edges of the neurostimulator are labeled, based on where the apparatus will be worn by the subject, as is illustrated in FIG. 3Q. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g., at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration).

The electrode apparatus may be printed (e.g., by flexographic printing, laser printing with conductive ink, silk-screening, etc.) on a flexible (e.g., plastic) substrate (flex substrate) and may also include a pair of connectors (snaps) on the side opposite the skin-facing electrodes. The electrode active regions on the back of the assembly may include a layer of conductor (e.g., silver), a layer of a higher resistance conductor than silver (e.g. a conductive carbon), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 3H-3K illustrate one variation of a cantilever electrode apparatus ("electrode apparatus") that may be used with a neurostimulator and may be worn on a subject's head. This variation may be referred to as a "calm" configuration, as it is adapted to connect to a user's temple or forehead and the back of a user's neck. In this example, the cantilever electrode apparatus 400 includes a plurality of electrode portions (two are shown) 403, 405. In FIG. 3H, a front perspective view is shown. The front side is the side that will face away from the subject when worn. The cantilever electrode apparatus is thin, so that the electrode portions include a front side (visible in FIGS. 3H and 3I) and a back side (visible in FIG. 3K). As shown in the side view of FIG. 3J, the device has a thin body that includes the electrode portions 403, 405 as well as an elongate body region 407 extending between the two electrode portions. The elongate body is also thin (having a much larger diameter and height than thickness). The thickness is shown in FIG. 3J.

In this example, two connectors 415, 417 (electrical and mechanical connectors, shown in this example as snaps) extend from the front of the cantilever electrode apparatus. The front of the first electrical portion 403 may also include an optional foam and/or adhesive material 421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 3H-3K as about 0.72 inches). The second electrode portion may also include a foam or backing portion 423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 3K shows a back view of this first example of a cantilever electrode apparatus. In this example, the first 403 and second 405 electrode portions are also shown and include active regions 433, 435. The active regions are bordered by adhesive 440. The first 403 electrode portion includes, on the back (patient-contacting) side, a first active region 433, which is bounded, e.g., around its entire circumference, or at least on, by an adhesive 440. The active region may include a conductive material (e.g., electrically conductive gel). Similarly, the back of the second electrode portion 405 includes the second active region 435 surrounded on two sides by an adhesive material 440 that extends to the edge of the electrode region. The adhesive may be any biocompatible adhesive that can releasably hold the material to the skin.

FIGS. 3L-3o illustrate another example of a cantilever electrode apparatus. This example is very similar to the variation shown in FIGS. 3H-3K, but may be referred to as an "energy" configuration as it is configured to contact both the user's temple or forehead and a region behind the user's ear, over the mastoid region. The connectors (snaps 417, 415) are in the same position as shown in FIGS. 3H-3K, as are the shape of the first electrode portion 403 and foam/backing material 421 (which may also or alternatively be an adhesive material). An advantage of having multiple electrode apparatuses with the same shape is that they can be used interchangeably with a single neurostimulator device. However, the example shown in FIGS. 3L-3o includes a different overall shape, and may be used to connect, for example, to different regions of the patient's head. In particular, the portion of the substrate forming the elongate body region 407 extending between the two electrode portions 403, 405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple or forehead and using the adhesive material 440 surrounding the electrically active region 433 to hold the electrically active region (and the attached neurostimulator) securely in position on the subject's skin, the second electrically active region may also be adhesively 441 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 3H-3K and 3L-3o. The bend or curve, in which the elongate body may even double back on itself, may allow the material to flex or bend to allow it to be adjustably positioned over and/or around the subject's head, as shown in FIGS. 3P and 3Q, for example.

Figure 3P:
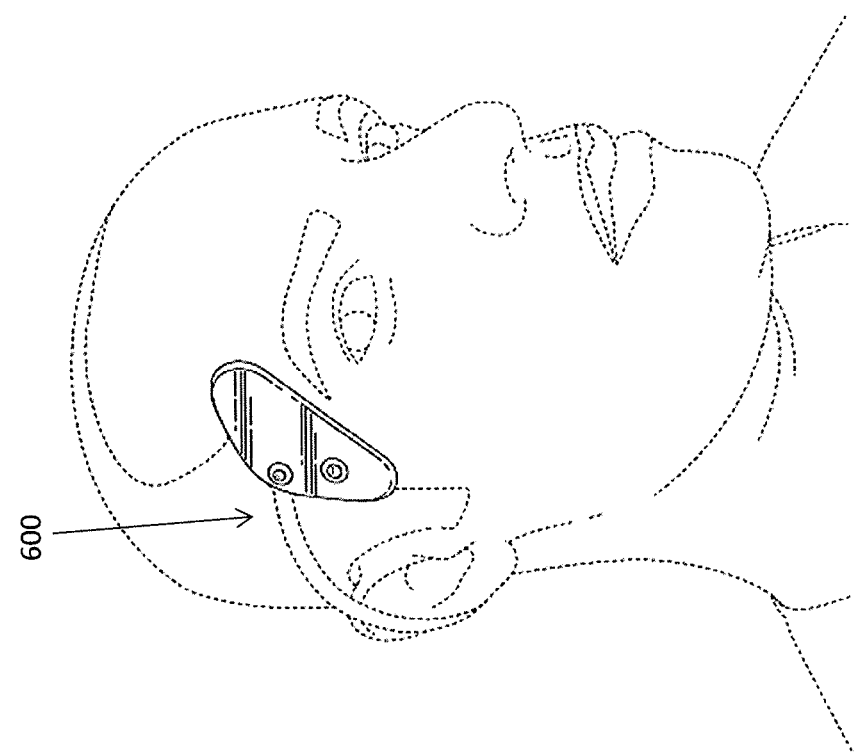
FIG. 3P illustrates the application of an electrode assembly that may be worn on the subject's head, and/or head and neck to induce a cognitive effect.

FIG. 3P illustrates a cantilever electrode apparatus (similar to those shown in FIGS. 1A and 4A) worn on a subject's head. As illustrated, the apparatus is positioned with the first electrode portion adhesively attached at the temple or forehead and a second electrode portion attached to a region behind the head (e.g., behind the ear or neck region, not shown). A neurostimulator (not shown in FIG. 3P) may be attached to the cantilever electrode apparatus either before or after it is applied to the subject. As shown in FIG. 3Q, the neurostimulator may be attached to the front side of the cantilever electrode apparatus by snapping onto the proud connectors, while the elongate body region 407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in application Ser. No. 14/320,443, titled "TRANSDERMAL ELECTRICAL STIMULATION METHODS FOR MODIFYING OR INDUCING COGNITIVE STATE" and filed on Jun. 30, 2014, and herein incorporated by reference in its entirety.

In use, a user may interact with a controller (e.g., a smartphone controlled by application software/firmware) that pairs with the neurostimulator (e.g., i.e., by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e., current amplitude, frequency, duty cycle, charge imbalance, shorting/capacitive discharge, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e., tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

EXAMPLES

Three additional examples of parameters for ensemble waveforms are described below. In these examples the waveforms may be implemented in the neurostimulation systems described above and illustrated in FIGS. 3A-3Q. These waveforms may be defined as a vector array including the duration and waveform parameters (frequency that the basic waveform unit is repeated, peak current amplitude, percent charge imbalance of the basic waveform unit, percent duty cycle of the basic waveform unit, and, optionally, capacitive discharge parameters and/or amplitude modulation or burst mode parameters). The basic waveform unit may be defined, or may be set by the system, e.g., as biphasic, square pulses having a predetermined or variable period cycle (i.e., by composing waveforms having chirped pulses).

Example 1 is shown in FIG. 4A, and is another example of a calm ensemble waveform. The table shown in FIG. 4A lists the waveform parameters for each of the component waveforms. In this example the ensemble waveform is configured with short circuiting on (meaning that a capacitive discharge pulse occurs in the opposite direction after each of the biphasic pulses).

In operation, the system transfers chunks (e.g., 400 ms segments) securely between the user device and the worn neurostimulator every about 400 ms (or on multiples of about 400 ms), including the neurostimulation start frequency, end frequency, starting amplitude, end amplitude, start duty cycle, end duty cycle, start percent charge imbalance, end charge imbalance, etc. The timing of wireless communication chunks at about 400 ms should not be construed as limiting the timing of communication between a controller unit and the neurostimulator.

FIG. 4B illustrates a second example of a calm ensemble waveform having a slightly longer running time, running over 12 minutes. Similarly, 4C illustrates a third example of a calm ensemble waveform having a yet longer running time (over 16 minutes).

FIG. 5A illustrates another example of an energy ensemble waveform. In these examples of ensemble waveforms for inducing enhanced energy, short circuiting (capacitive discharge) may be set to 'on' (or off). In this example, the capacitive discharge may also be configured to occur in the opposite direction after each of the biphasic pulses. In contrast, FIG. 5B illustrates an example of an energy ensemble waveform in which a capacitive discharge is formed in the negative going direction and occurs at the onset of each negative going pulse (see FIG. 1D, above).

The ensemble waveforms described herein may be divided up into at least two categories, including energy and calm types of ensemble waveforms. These two categories or classes of waveforms may have different characteristics, which may make them appropriate for the physiological delivery location and the induced effect. In some variations, the energy waveforms and/or the calm waveforms are specific in their effects; for example a calm ensemble waveform may not induce any effect when applied using an energy treatment regime, and vice versa. In general, the calm ensemble waveforms described herein may have higher frequency waveform parameters (for example, a larger percentage of ensemble waveforms may have a frequency above 10 kHz, e.g., 50%, 60%, 70%, etc.) compared with energy waveforms, and the current amplitude may vary more often (e.g., between component waveforms) than with energy component waveforms. In contrast, the energy ensemble waveforms may typically have a lower range of frequency waveform parameters (e.g., down to 750 Hz), and may not need short circuiting (capacitive discharge). In addition, the percentage of charge imbalance in the energy waveforms may be in a 30-50 percent range. In addition, in energy ensemble waveforms there may be more shifting of frequency between component waveforms than with calm ensemble waveforms (e.g., shifting from 11 KHz to 7500 Hz to 9 kHz, etc., typically shifting by approximately 1-3 kHz, e.g., 2 kHz jumps), which may occur on a longer time scale (e.g., longer than every 30 seconds) or over a very brief timescale of less than 10 seconds.

There may also be general features that are shared between many of the ensemble waveforms described herein. For example, in general, when ensemble parameters are changed after longer duration blocks, two or more waveform parameters may be adjusted at once. Further, when shifting frequency between component waveforms by 2 kHz or more, at least one other waveform component may also be shifted. In general, rapid shifts in frequency or current amplitude (e.g., shifting down and back up within a 10 sec, period, e.g., 1 sec, 2 sec, 5 sec, etc. period) may be useful to intensify the desired effect for either calm or energy. For example, FIG. 6 illustrates one example of an add-in that may be applied onto an ensemble waveform to intensify an effect. In this example, the add-in provides a gradual ramp down of the intensity (e.g., applied current amplitude) of the ensemble waveform currently being applied by scaling it by the intensity factor shown (intensity factor %) over the duration (e.g., 0.8 s) provided; thereafter the intensity may be quickly returned to 100% of the value otherwise delivered but for the add-in (e.g., which may also be adjusted by a user-selected intensity control and by the value of the ensemble waveform at that time). The result of the add-in shown in FIG. 6 may, in some users, be to intensify the cognitive effect being evoked (e.g., enhanced calm, increased energy, etc.).

Another exemplary ensemble waveform to induce a state of increased energy (e.g. with electrodes positioned on the right temple/forehead area and the right mastoid, as described above) is approximately 10 minutes in length and incorporates capacitive discharge current (discharges) after each positive-going and negative-going pulse of the waveform. For example, this TES ensemble waveform for inducing an increase in energy (or related cognitive effects of alertness and physiological arousal, etc.) may include three component waveform types delivered in sequence. A first component waveform ("A") of the ensemble waveform has a duration of 60 seconds, during which time the peak intensity gradually and linearly increases from 0 mA to 14 mA with waveform parameters including: 7 kHz frequency, 85% charge imbalance, 49% duty cycle, 90 Hz bursting frequency, and 50% bursting duty cycle. A second component waveform ("B") of the ensemble waveform has a duration of 535 seconds, during which time all parameters of the waveform remain constant except the duty cycle percentage, which gradually increases to 55%. In a third and final component waveform ("C") of the ensemble waveform has a duration of five seconds, and the current ramps down to 6 mA (and then to zero mA, as the ensemble waveform completes) while all other waveform parameters (frequency, percent duty cycle, etc.) are identical to those during the second waveform segment of the ensemble waveform. These component waveforms (e.g., A, B, C) may then be repeated (or may be repeated as A, B, A, B, A, B, . . . , C).

Another exemplary ensemble waveform has a five minute total duration, and may be used to induce a state of increased energy (physiological arousal, etc. as described above). This example includes two core waveforms with component waveforms of an ensemble providing gradual onsets, offsets, and shifts of these waveform components. A first set of waveform parameters ("A1") of this component of the ensemble waveform gradually ramps the intensity of stimulation up to 12 mA over 30 seconds for a waveform with a frequency of 7600 Hz, a charge imbalance of 81%, a duty cycle of 52%, a bursting frequency of 90 Hz, and a bursting duty cycle of 22%. A second set of component waveform parameters ("B1") of this ensemble waveform gradually increases the peak intensity to 13 mA with all other parameters identical to the first ensemble component. The gradual increase in intensity over 120 seconds of the second component may help counteract any habituation that may occur in response to electrical stimulation of the subject's skin. A third set of component waveform parameters ("C1") of the ensemble waveform shifts several waveform parameters gradually over 25 seconds to: 8600 Hz frequency, 14 mA peak intensity, 81% charge imbalance (unchanged from the preceding waveform component), 57% duty cycle, 90 Hz bursting frequency (unchanged from the preceding waveform component), and a 32% bursting duty cycle. By slightly increasing the duty cycle, bursting duty cycle, and peak intensity, the relative (perceived) intensity of the waveform to the subject may be minimally changed despite increasing the stimulation frequency by 1 kHz. In general, higher stimulation frequencies in this range may correspond to more comfortable waveforms. In a fourth set of component waveform parameters (D1), the parameters to which the waveform adjusted during the preceding waveform component are maintained for 120 seconds, then in a fifth set of component waveform parameters (E1) the intensity of stimulation is gradually ramped down to 7 mA over 5 seconds (then, as the ensemble waveform completes, the intensity gradually ramps to 0 mA over a duration of a few seconds).

In general, an ensemble TES waveform may include component waveforms with continuous stimulation (i.e. no quiescent periods between presentations of a waveform cycle). In a third exemplary ensemble waveform, which may be used to induce an increase in energy, alertness, physiological arousal, etc., no bursting occurs in waveform components for the first 8 minutes of the ensemble waveform (e.g., no amplitude modulation is applied over this time), then the last two minutes of the ensemble waveform include components with bursting (amplitude modulation using a square pulse waveform, as described in greater detail below).

In any of the ensemble waveforms described herein, the peak intensity may generally be scaled according to a user input to a peak intensity value that is a percentage of the peak intensity indicated (e.g. 5%, 30% of the peak intensity, 40%, 50%, 60%, 70%, 80%, 90%, 100% and values there between).

The use of ensemble waveforms, which are made up of discrete periods of component waveforms each having one or more distinct parameters as described above have proven to be particularly effective when evoking cognitive states by TES. In part, this may be because the use of ensemble waveforms may help avoid habituation. Further, the inventors have found from empirical data across a population of users that different users prefer different parameter sets for comfort and efficacy of inducing a cognitive effect. The application of ensemble waveforms as described herein allows cycling through multiple different parameter sets that, while perhaps not optimal for all users, has proven surprisingly effective for a wider range of people. Shifting parameters as described herein when using ensemble waveforms may also be more effective than static waveforms by both preventing desensitization on one time scale (e.g. at the neuronal level) while evoking cognitive effects at a different level (e.g., neural network) over a longer timescale.

For example, the use of multiple (e.g., greater than 3, 4, 5, etc.) component waveforms each having a duration of between 100 msec and about 600 seconds may also provide functional translation between cranial nerve modulation and brainstem modulation. The component waveforms themselves are configured to penetrate the skin and soft tissue to reach the nerves. For example, the high-frequency, higher-intensity component waveforms may allow relatively deeper penetration than lower-intensity signals. However, the cognitive effects seen are not just due to the activation/modulation of nerves. The evoked effects may depend on these nerves reliably modulating brainstem nuclei. An analogy may be found with TENS for the gate control theory of pain; whereas nerves can be activated in the first second of stimulation, in many systems, the durations used are instead on the order of 30-45 seconds to (hypothetically) modulate brainstem nuclei involved in pain control. This suggests that the time course for nerve modulation to yield brainstem modulation is much slower (seconds to tens of seconds) than the time course for nerve modulation (which is less than a second). Most neural circuits typically adapt to constant inputs and become less sensitive. To avoid adaptation in cranial nerves, the ensemble waveforms described herein may use rapid changes in the underlying waveform that occur, e.g., in less than a second. Similarly, these signals may be at least partially amplitude modulated, which may also help prevent adaption in the brainstem, using transitions that occur on the timescale that it takes to modulate the brainstem using cranial nerve inputs (e.g., seconds to tens of seconds). Slower effects may be mediated by signal processing and signal transduction cascades involving brain stem nuclei. This may be analogous to descending pain control systems for example which are well understood to involve a cascade of second messenger systems. In pain applications TENS also rather immediately affects brainstem and spinal pathways. Delayed effects may be due to slower intracellular second messenger systems.

Amplitude Modulation (AM)

As mentioned above, any of the waveforms (compound or ensemble waveforms) described herein may be amplitude modulated, which may modify, including enhancing, the cognitive effects achieved. In particular a subset of the component waveforms forming an ensemble waveform may be amplitude modulated as described herein. Any of the apparatuses and methods described herein may include amplitude modulation of all or some of the component waveforms, and the amplitude modulation applied to different component waveforms may be the same or it may be different, for example, having different AM envelope shapes (square, sawtooth, sinusoidal, etc.), different AM frequency (burst frequency), different AM percent duty cycle (e.g., burst duration), etc.

Thus, any of the component or ensemble waveforms described herein may be modified by amplitude modulation so that a second, generally lower, frequency component (and this second frequency component may be varied or constant) may be applied atop the component or ensemble waveform. Amplitude modulation may be considered another type of add-on effect, because it may intensify or qualitatively modify (i.e. cause a distinct subjective cognitive experience) the desired cognitive effect.

In general, the inventors have found that amplitude modulation (AM) is a beneficial feature in the use of TES waveforms, because cognitive effects can be induced with improved comfort.

Amplitude modulation as described herein typically results in overlaying a bursting of some or all of the component waveforms of an ensemble waveform, which may both decrease the overall power requirement of the system, since less overall current is applied (thereby potentially expanding battery life or reducing the demand for larger power sources), and may also be more effective in evoking a modification of a subject's cognitive state, as mentioned above. Finally, the use of amplitude modulation has been found to enhance comfort, and surprisingly allow even greater current intensities to be used, despite decreasing desensitization.

The frequency of the applied AM is typically lower than the carrier frequencies of stimulation (the component and/or ensemble waveform frequencies), and may generally be between about 0.5 Hz and 1 kHz; strictly speaking any frequency below a dominant frequency of a carrier wave may be used for AM, although particularly effective AM frequencies may be between about 10 Hz and about 1 kHz, including neurobiologically relevant frequencies below about 200 Hz.

One advantage of amplitude modulation may be that the total energy delivered transdermally per unit time may be reduced while still evoking a robust response. This principle motivates the use of amplitude modulation duty cycles less than 100% (preferably less than 80%, less than 70%, less than 60%, etc.). However, significantly lower duty cycles (i.e. less than 20%) may be less effective due to discomfort occurring as a result of a larger proportion of the frequency-spectrum power of stimulation in a lower frequency range for which skin impedance is lower and somatosensory receptors are more likely to be activated.

The amplitude modulation waveform applied may be any appropriate shape, including square waves, triangular ("sawtooth") waves, sinusoidal waves, or the like. For example, amplitude modulation by a sine wave or similar smoothly varying curve may be particularly beneficial for modulating (i.e. entraining, strengthening, phase-shifting) brain rhythms. Brain rhythms are well known in the art and include frequencies of oscillation associated with brain function (i.e. delta, beta, alpha, theta, gamma, etc.).

TES waveforms that include bursting generally deliver pulsed stimulation waveforms with high peak currents (i.e. greater than 2 mA, greater than 5 mA, etc.) and a relatively high carrier frequency of greater than 750 Hz (i.e. above 1 kHz, above 5 kHz, above 10 kHz, etc.) that are delivered intermittently, with periods of lower (preferably, zero) stimulation. Burst mode TES waveforms are a form of amplitude modulation TES waveform. Any of the amplitude modulation waveforms described herein may further incorporate other time-varying features of ensemble waveforms. That is, amplitude modulation may be an additional control structure that can be used to deliver more comfortable electrical stimulation for inducing a cognitive effect, as illustrated and described below.

For example, FIGS. 8A-8D, 9A-9D, 10A, 10D, and 12A all illustrate amplitude modulation on a zero to one (or −1 to 1) scale, where a value of zero represents a cessation of stimulation of the underlying carrier wave (defined by frequency, pulsing regimen, duty cycle, intensity, etc. as outlined herein), a value of one represents a maximum stimulation intensity as defined by the underlying carrier wave, a value of negative one represents a maximum stimulation intensity in the negative-going direction, and values intermediate between zero and one represent a modulation of the underlying waveform to have an associated intermediate intensity (e.g. envelope).

FIG. 8A shows an exemplar AM burst stimulation framework for TES and defines terms used to describe AM herein. The extent of amplitude modulation is generally defined from 0 to 1 and may represent a time-varying multiplier for a pulsed stimulation regime. In the example shown in FIG. 8A, the amplitude modulation is applied by square wave pulses (which may result in bursts of the applied component waveforms in the ensemble waveform applied). In this example, either a multiplier of zero (i.e. no current delivered) or one (full amplitude of stimulation delivered) is applied to the ensemble waveform (or a component portion thereof). The relative length of a pulse and inter-pulse time may define the duty cycle of the resulting bursting due to amplitude modulation in the applied ensemble waveform. The combined time may be equal to a burst period which is equal to the inverse of the AM pulse frequency. Bursting generally continues due to the multiple cycles of amplitude modulation. In FIG. 8A, the amplitude modulation duty cycle (AM duty cycle) is the percentage defined as the burst length 811 divided by the burst period 813, which is approximately 30% in FIG. 8A.

FIG. 8B shows how a duty cycle of AM (and therefore the 'bursting' duty cycle seen in the resulting ensemble waveform) may vary between TES waveforms. The AM applied by the AM waveform in FIG. 8B has a similar frequency as shown in FIG. 8A, but a larger (approximately 50%) AM duty cycle resulting in the larger bursting duty cycle in the resulting applied waveform (ensemble waveform or one or more component waveforms in the ensemble). The total charge transfer when applying the waveform of FIG. 8B is higher than that of FIG. 8A (for a fixed ensemble, or 'carrier', wave structure, intensity, and frequency), which may be beneficial for more strongly modulating a nerve or brain region.

FIG. 8C shows an AM waveform with the same AM pulse width ("burst length") as FIG. 8A and higher AM pulse frequency ("AM frequency" or "burst frequency"). Changing the frequency or duty cycle of the AM waveform may induce stronger cognitive effects. For example, effective TES waveforms may shift the frequency and/or duty cycle of stimulation during an ensemble waveform on a timescale between 1 sec and 10 minutes (optimally, 10 seconds to 5 minutes). FIG. 8D shows a set of AM pulses for TES with fixed length, but the AM wave applied changes frequency, which may be a beneficial characteristic of some ensemble AM waveforms.

Figure 11:
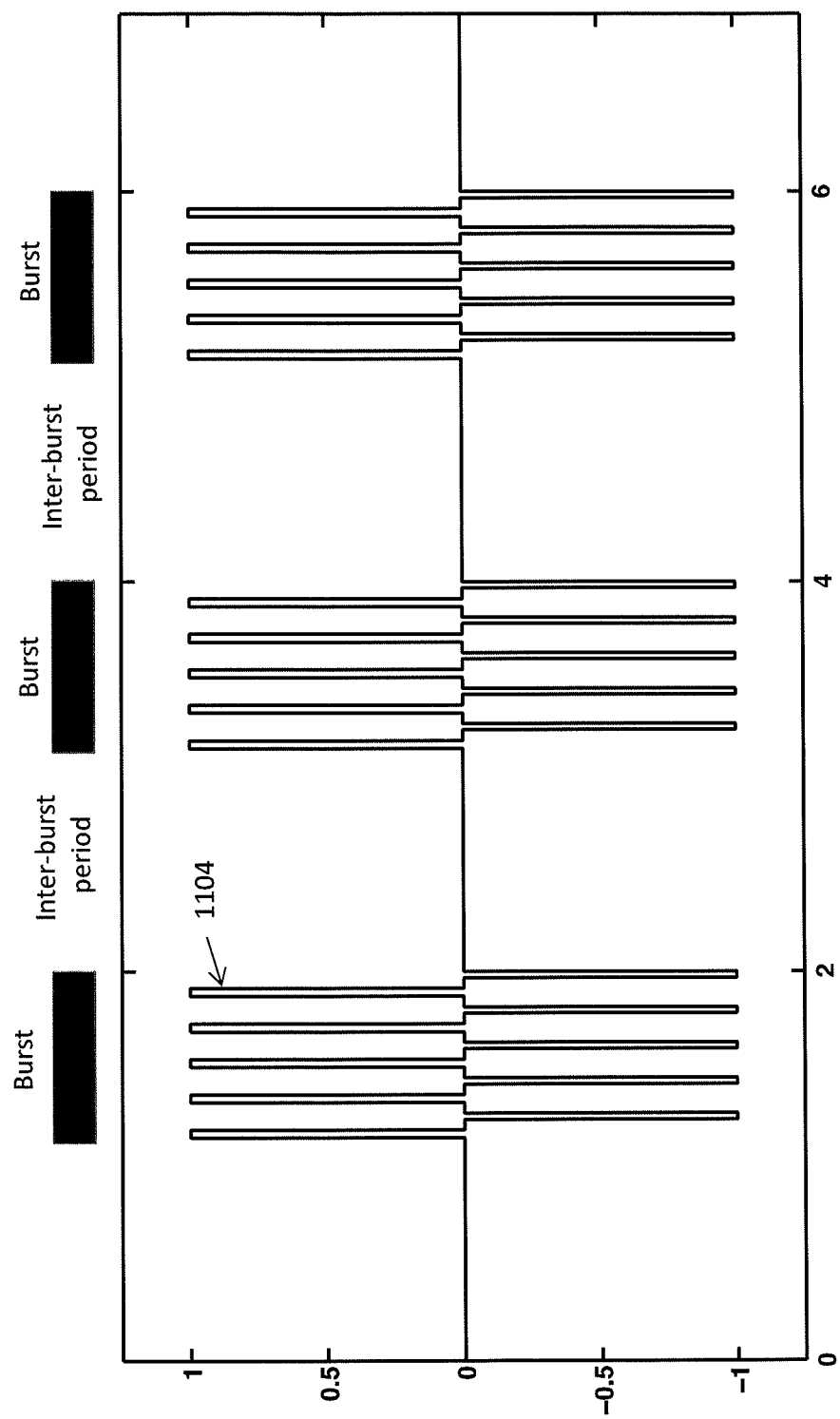
FIG. 11 graphically depicts the use of amplitude modulation (AM) with a square pulse AM modulating waveform.

FIG. 11 illustrates one example of a square-wave envelope for amplitude modulation shown modulating an exemplary portion of one component waveform of an ensemble waveform. In this example, three burst cycles are shown (as indicated by black rectangles at top of figure). The AM is applied to a portion of an ensemble waveform (or component waveform) having a biphasic pulsed 5 kHz carrier signal delivered with a 50% bursting duty cycle and a 500 Hz burst frequency. The resulting waveform has defined bursting periods ("bursts") and quiescent periods ("inter-burst periods"). Without amplitude modulation, these quite periods would resemble the bursts; the AM in this example acts to turn off the current during the inter-burst periods (when the AM envelope is zero). As described in greater detail below, the burst duration (e.g., percent duty cycle of the amplitude modulation waveform) as well as the amplitude modulation frequency (AM frequency) may be selected so that the bipolar pulses in the underlying component waveform (the base pulses 1104) are not truncated, e.g., so that the edge of the burst envelope does not cut off a burst but instead corresponds with the start of the next pulse cycle.

Figure 9A:
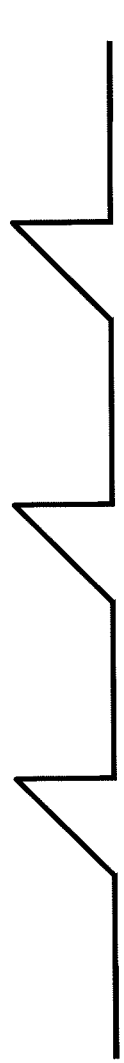
FIGS. 9A-9D show examples of various amplitude modulation waveform shapes that may be used to provide a repeating and time-varying scaling factor of waveform intensity.
Figure 9B:
Figure 9C:
Figure 9D:

The amplitude modulation envelope shapes are not limited to square waves. Other shapes for applied amplitude modulation may be effective for improving comfort and/or enhancing or modifying a cognitive effect induced in a user receiving TES. FIG. 9A shows a sawtooth wave-shaped amplitude modulation for bursts in which the start of each burst ramps up the intensity of stimulation gradually (i.e. which may improve comfort). FIG. 9B shows a triangle wave-shaped amplitude modulation for bursts in which the start and end of each burst ramps the intensity of stimulation gradually. FIG. 9C shows a roughly exponential-shaped amplitude modulation for bursts in which the start of each burst ramps up the intensity of stimulation gradually (i.e. to improve comfort). FIG. 9D shows a roughly exponential wave-shaped amplitude modulation for bursts in which the start and end of each burst ramps the intensity of stimulation gradually.

Another envelope shape for amplitude modulation is sine-wave amplitude modulation, which may result in gradually shifting peak intensities. One skilled in the art will recognize that various smoothly varying forms of AM may be as potentially effective (and comfortable) as a sine-wave AM envelope. FIG. 10A shows three cycles of a sine-wave amplitude modulation between zero and one (though other sine-wave AM frameworks are also possible that vary between values greater than zero and/or less than one, such as that shown in FIG. 10D, where amplitude modulation occurs with a minimum value greater than zero during the sine wave modulation). The arrows pointing to FIGS. 10B and 10C illustrate two cycles of pulsed waveforms as in FIG. 1C, where the cycles from FIG. 10B are roughly half the amplitude of those in FIG. 10C based on the time during the AM cycle when they are delivered.

Figure 12A:
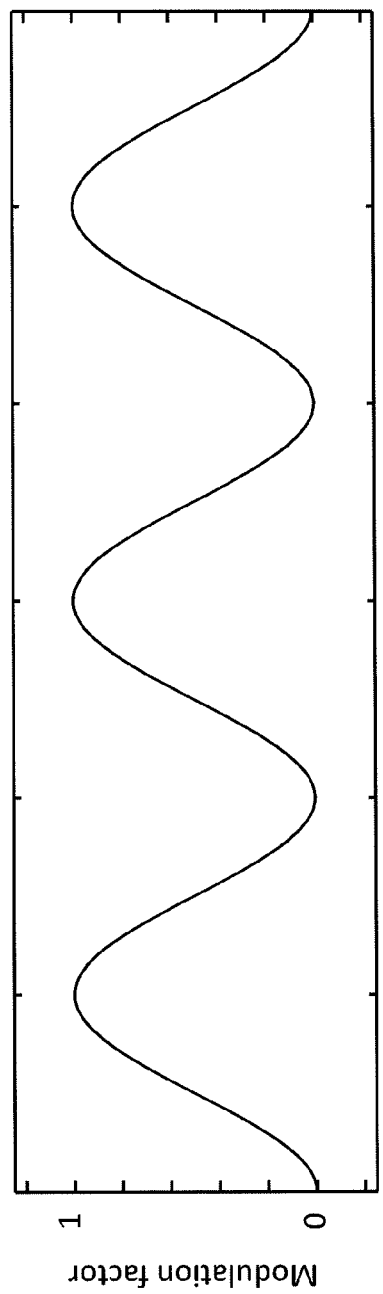
FIGS. 12A and 12B graphically illustrate the use of amplitude modulation (where the modulating waveform is a sinusoid as shown in FIG. 12A) to modulate a component (or ensemble) waveform as shown.
Figure 12B:
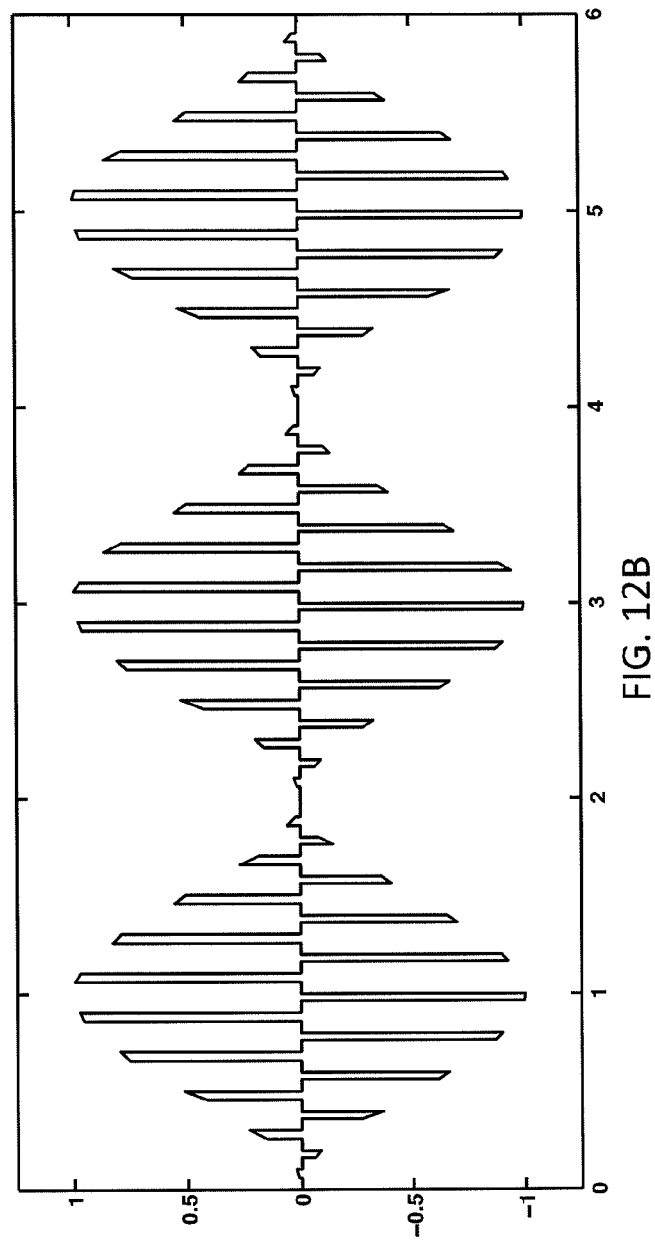

FIG. 12A shows another example, including a 500 Hz sine-wave amplitude modulation curve, and FIG. 12B shows the stimulation waveform delivered with a constant 5 kHz pulsed frequency (e.g., "carrier wave", which may correspond to the component waveform parameters) throughout the three cycles of amplitude modulation displayed. In some ensemble waveforms, the frequency, shape, or modulation factor of amplitude modulation may vary while the higher frequency carrier wave remains constant. In some ensemble waveforms, the frequency, shape, or modulation factor of amplitude modulation may remain constant while the higher frequency carrier wave changes by one or more intensity, frequency, duty cycle, charge imbalance, capacitive discharge, ramping, etc.

Amplitude modulation may allow a reduction of the applied intensity while retaining the robustness of the cognitive effect. For example, an ensemble waveform applied at 750 Hz, 4 mA with 30-40% duty cycle without applied AM may be equivalent to a 750 Hz, 3 mA, 30-40% duty cycle stimulation. In general, the use of amplitude modulation within the lower frequency ranges described herein may therefore allow a reduction in one or more of current amplitude, duty cycle and/or frequency. For example, one way to comfortably achieve the effects attributed to low duty cycle stimulation (including invoking cognitive effects, and/or, for example, phosphenes) may be to apply somewhat low frequency AM (e.g., between 100 Hz and 1 kHz, e.g. 200 Hz) to an ensemble waveform having carrier frequency values outside of this range that are more easily tolerated, e.g., the carrier waveform may have a frequency of 8 KHz and an amplitude of 10 mA). The amplitude modulation envelope may define in an AM burst mode of the carrier waveform resulting in a comfortable while still robust effect.

For example, FIG. 7 illustrates one variation of an ensemble waveform designed for use to evoke a calming cognitive effect. In this example, the 10 minute waveform includes square-wave modulated AM (resulting in "bursts") of the ensemble waveform at frequencies between 500-800 Hz, with an AM duty cycle (atop the ensemble waveform duty cycles) of between 40-85%. In some variations, the use of AM at a burst (e.g., pulse) frequency of between about 200-900 Hz, and between about 20-95% duty cycle (e.g., AM duty cycle or burst duty cycle) may be particularly effective to potentiate the cognitive effects seen with the non-AM ensemble waveforms, particularly when the AM parameter (e.g., frequency and/or duty cycle) is changed during the application of the ensemble waveform. This may be referred to as AM mode stimulation or the application of amplitude modulated ensemble waveforms, which may make the evoked cognitive effect experienced by the user stronger. Rapid shifts in the AM within a few seconds to minutes may be particularly helpful.

For example, FIGS. 13-15 show examples of the stimulation parameters that may be used (e.g., by a neurostimulator) to deliver ensemble waveforms. For example, in FIG. 13, the parameters of a 5 minute ensemble waveform configured to evoke a calm cognitive state are shown. In this example the ensemble waveform has 3 component waveforms of different durations. For example, the first component waveform is a brief, 1 sec, ramp to 1 mA at 7000 Hz and 85% duty cycle; the second component waveform is 60 seconds long, during which time the current increases to 11 mA; the third component waveform lasts for 540 additional seconds, during which the duty cycle increase from 49% to 70%. The entire ensemble waveform is amplitude modulated by a 70 Hz modulation (e.g., using a square pulse modulation) having a duty cycle of 35%. Each of the intensities listed is a maximum intensity, and a user may manually adjust intensity (or another variable such as the duty cycle or frequency of the carrier wave) to achieve a desired subjective intensity of stimulation. This user adjustment may result in modifying the ensemble waveform during application by a user intensity adjustment factor. A user intensity adjustment factor may be transmitted by a controller, and may scale one or more parameters (e.g., current amplitude, percent duty cycle, frequency, etc.) of each of the component waveforms of the ensemble waveform.

FIG. 14 illustrates another example of an ensemble waveform, showing (in tabular form) the parameters of each of the component waveforms, including the use of a specific, and potentially distinct amplitude modulating for some or all of the component waveforms making up the ensemble waveform. In the example of FIG. 14, the ensemble waveform has 11 component waveforms. The amplitude modulation varies multiple times during the application of the ensemble waveform (in this example, between each of the $2^{nd}$ to $11^{th}$ component waveforms). Thus, the applied amplitude modulation is configured so that the AM frequency and/or duty cycle changes over the application of the component waveforms, even as the ensemble waveform ("carrier") changes or remains constant between different component waveforms (e.g., component waveforms 2-4 in the series are identical except for the applied amplitude modulation). Also, in general, the change in amplitude modulation between different component waveforms may be instantaneous (e.g., applying the AM parameters and envelope immediately at the start of the component waveform), or they may be ramped up, as with changes in other component waveform parameters (e.g., current, percent duty cycle, charge offset, frequency, as discussed above).

FIG. 15 shows another example of a "calm" evoking waveform having a 10 minute duration in which the amplitude modulation (e.g., AM duty cycle and AM frequency) change during the application of the ensemble waveform with different sequential component waveforms forming the ensemble waveform.

Although the examples shown above are configured to evoke a calm cognitive state, waveforms configured to evoke any other cognitive states (in conjunction with proper electrode placement) may also be used. For example, waveforms configured to evoke a cognitive state of energy (as described above) may be amplitude modulated (see, e.g., FIGS. 10A-10C). Amplitude modulation frequencies between 20 and 200 Hz may be particularly useful for energy ensemble waveforms. Amplitude modulation of energy waveforms may allow comfortable and effective stimulation at a broader range of frequencies (including as high as 10-11 KHz or higher), and for duty cycle of component waveforms that may be higher than would be comfortable and effective for inducing a cognitive effect without amplitude modulation. Interestingly, lower frequency AM (e.g., less than 20 Hz, such as around 8-10 Hz AM) may result in evoking phosphenes. In some variations this may be desirable and AM may offer one means of reliably triggering phosphenes. For example, the apparatuses and methods described herein may be configured to allow a user to select triggering of phosphenes by selecting a control (e.g., button, knob, key, slider, etc.) which adjusts the amplitude modulation (e.g., percent duty cycle of AM and/or frequency of AM), e.g., triggering the apparatus to adjust the frequency of the AM to between about 5 and about 50 Hz (e.g., between about 5-30 Hz, between about 5-20 Hz, between about 5-15 Hz, etc.). The AM frequency may be maintained ongoing, or for a predetermined period (e.g., 1 sec, 2 sec, 3 sec, 4 sec, 5 sec, 10 sec, 20 sec, 30 sec, 40 sec, 50 sec, 1 min, 2 min, 5 min, etc., or less than any of these times, e.g., less than 1 sec, less than 2 sec, etc.) to induce repeated or ongoing phosphenes experienced by a user.

As mentioned above, in any of the examples of amplitude modulation described above, the frequency and/or percent duty cycle of the amplitude modulation (e.g., burst frequency and/or burst duration) may be adjusted to prevent truncation of pulses (e.g., bipolar pulses) of the component waveform. In general, this may be achieved in any appropriate manner, but may be done by setting and/or adjusting the frequency and/or percent duty cycle of the amplitude modulation relative to the frequency of the fundamental (e.g., base) pulses of the underlying component waveform (the "carrier wave" that is being amplitude modulated or made to burst, as described above).

For example, FIG. 16 illustrates the correction, adjustment or selection of a modulation frequency for an amplitude modulated component waveform. As mentioned above, each component waveform of an ensemble waveform may be separately amplitude modulated (or not amplitude modulated), and thus, may have a different burst frequency and/or burst duration. In general, the use of square-wave (burst inducing) amplitude modulation envelopes may be adjusted or configured to avoid truncation of the base/fundamental pulses 1601 within the component waveforms. FIG. 16A shows a simplified example of a portion of a component waveform. In this example the frequency of the component waveform is shown as 5 Hz, merely for purposes of this general illustration. As illustrated and described above, the frequency of a component waveform may typically be much higher, e.g. between 500 Hz and 30 kHz, etc. FIG. 16B shows an example of an amplitude modulation signal envelope (shown here as a square pulse envelope) having a frequency of 2 Hz; as described above, the frequency of the amplitude modulation (envelope) may be different, and typically may be one or more orders of magnitude less than the frequency of the component waveform. In this example, when amplitude modulation of the component waveform of FIG. 16A is applied using the envelope of FIG. 16B, the amplitude modulated component waveform (shown in FIG. 16C) includes truncated (partial) fundamental pulses 1603, 1605. Truncated pulses may be tolerated, and even, in some variations, beneficial, however, in general they may be eliminated by modifying the frequency of the amplitude modulation envelope.

Preventing truncation within the component waveforms forming the ensemble waveform may improve the cognitive effect and prevent undesirable and potentially painful charge imbalance and pH changes in the skin beneath the electrodes. As mentioned, any appropriate technique to remove or eliminate the truncated pulses may be used, including filtering of the signal (to remove truncated signals) or modification of the frequency of the amplitude modulation. For example, the duration (and therefore the frequency, which is one over the duration) of the amplitude modulation envelope may be set or adjusted to be a multiple of the duration of one period of a cycle of the component waveform ($t_s$), which may help prevent truncation of pulses of the component waveform; similarly, the burst length of the amplitude modulation may be set or adjusted to be a multiple of the $t_s$.

In some variations, it may be beneficial to adjust a target frequency and/or percent duty cycle (burst length) so that the resulting AM does not truncate pulses of the component waveform. For example, the duration of an amplitude modulation waveform may be adjusted to subtract out the fraction of the component waveform that is truncated. The original desired frequency for amplitude modulation may be adjusted by determining the duration of the fraction of the initial fundamental pulse of the component waveform that is truncated by the envelope, and subtracting the duration (e.g., when both the envelope and the component waveforms start at the same time) from the duration of the amplitude modulation envelope.

In FIG. 16D, the duration of the amplitude modulation envelope has been adjusted by subtracting the duration of the partial pulse 1603. The resulting AM duration (burst period) is close to the desired initial frequency and is a multiple of the component waveform duration (as is the burst duration) thereby preventing truncation of pulses within the component waveform. This is illustrated in FIG. 16E. In this example, the resulting envelope (burst) duration is twice the duration of the fundament frequency of the component waveform (e.g., the duration of the adjusted/corrected amplitude modulation envelope in this example is 0.4 seconds, with a frequency of 2.5 Hz).

Waveform Controller

Figure 17B:
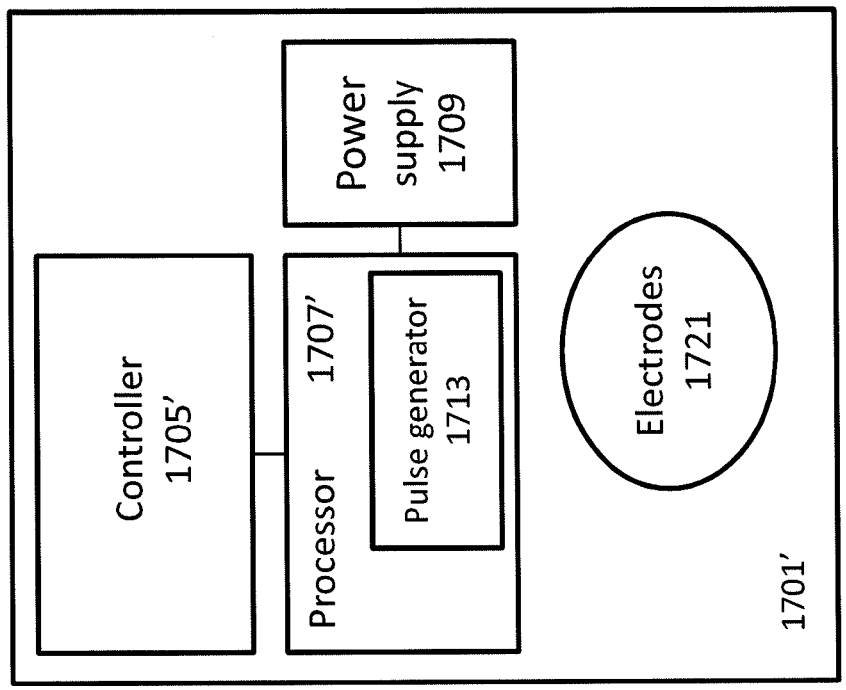
FIG. 17B is a schematic illustration of another example of a system in which the controller and processor are directly connected, rather than wirelessly connected.
Figure 17A:
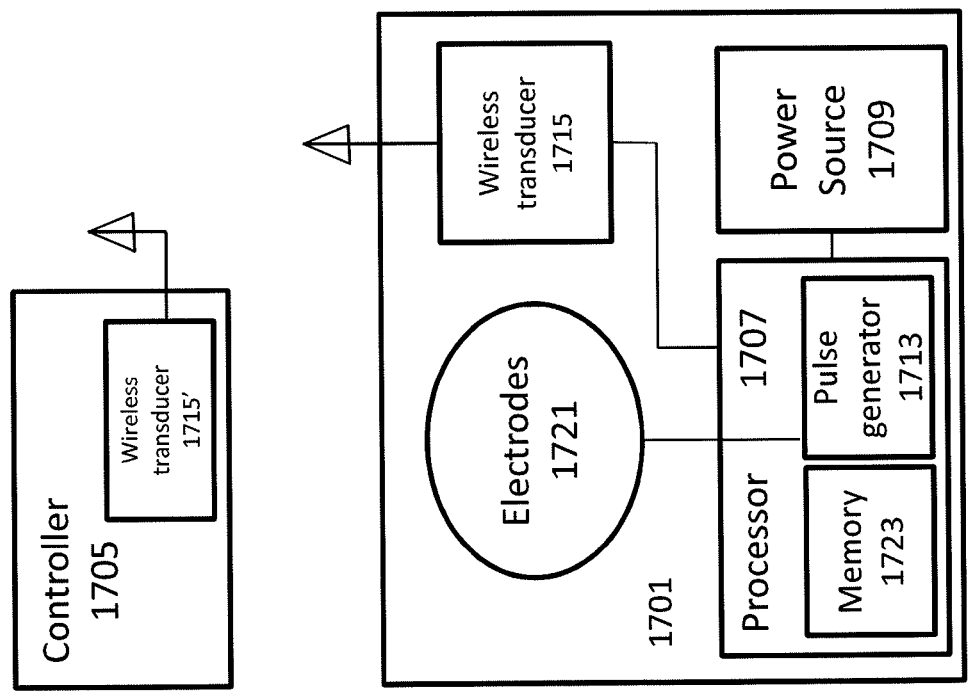
FIG. 17A is a schematic illustration of one example of an apparatus (e.g., system) including a wireless controller that sends command instructions, including ensemble waveform information, to a wearable neurostimulator having a processor adapted to receive and interpret this information, which may be sent in an abbreviated and efficient message encoding system.

Also described herein are method for efficient, compact and rapid communication of ensemble waveform control information from a controller (waveform controller) to a wearable neurostimulator. The controller may be remotely located relative to the wearable neurostimulator. FIG. 17A is a schematic illustration of a wearable neurostimulator 1701 such as the ones described herein (e.g., FIGS. 3A-3Q), which may wirelessly receive control information (e.g., ensemble waveform information and/or command controls from a waveform controller 1705). In this example, the wearable neurostimulator includes at least two electrodes 1721 that are integral with or connectable to the neurostimulator 1701, and a processor 1707 that connects to wireless communication circuitry 1715 (e.g., wireless transducer), a power source 1709, and a pulse generator 1713 to apply the waveforms via the electrodes 1721. The processor may also include a memory 1723 having one or more registers for storing waveform information, including one or more of a: a current and/or next component waveform. The waveform controller 1705 may also include wireless communication circuitry 1715' for transmitting (and/or receiving) control information, including component waveform control information.

The processor 1707 is generally configured to receive and handle waveform information. Specifically, the processor described herein is configured to operate in real-time to communicate with and receive information from the waveform controller. The waveform controller may transmit (e.g., in real-time or near-real time) sequential component waveforms from the series of waveforms forming an ensemble waveform; to achieve this, the controller and processor share a specific communication architecture that allows the rapid and reliable transmission of component waveforms to the wearable apparatus, allowing the wearable apparatus to deliver the potentially complex ensemble waveform in an energy-efficient and reliable manner.

Specifically, the controller may transmit one or more control codes that may be received by the processor. A variety of control codes may be transmitted, for controlling any of the functions of the wearable neurostimulator, including self-reporting codes (instructing the device to run and/or return diagnostic information including power charge status), LED controls, pairing controls, power-down controls, and the like. In particular, the controller may transmit control codes instructing the neurostimulator to receive waveform information and in particular component waveform information. A command control may tell the processor to prepare to receive and/or deliver a new component waveform, or it may tell the processor to edit or modify an existing component waveform; the command control may also specific the number of segments to expect for the new component waveform or which segments in a stored (including currently running) component waveform to modify.

For example, a first command message (e.g., "new waveform" message/command control) may instruct the processor of the wearable apparatus to prepare a memory register ("shadow register") to receive waveform information. This message may indicate that the processor should start a "new" component waveform or use a component waveform already stored (which may be the waveform most recently delivered by the device). In general, the command messages may be structured to include a message identifier (message ID) that indicates what the message will contain (e.g., which may be recognized by the processor via a look-up table or other mechanism), and/or routing information (e.g., destination and/or source endpoints), and a message payload, which may be the message, such as the new waveform message or the waveform segment message discussed below.

Figure 18A:
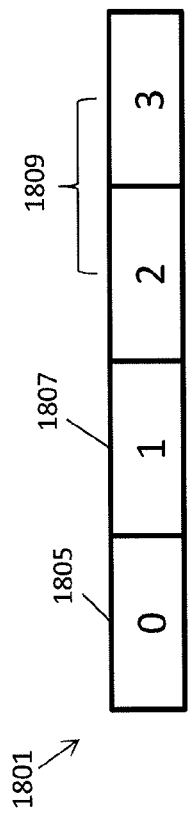
FIG. 18A schematically illustrates a generic message (e.g., a message format having a size, in this example, of 20 bytes) configured for transmission between the controller and the processor of the neurostimulator.

FIG. 18A is a schematic illustration of a generic command message structure that may be used. In this example, the message is a finite size (e.g., 20 bytes, though the systems described herein may be configured to handle any appropriate size, more or less than 20 bytes, e.g., 21, 22, 23, 24, 25, 26, 27, 28, 29, 30 bytes, etc.). The message includes a message identifier (Message ID) and a message payload. The command message may also (optionally) include destination and source endpoints. This message structure may be used for any of the command messages described herein, including the new waveform command messages (see FIG. 18B) and segment command messages (see FIG. 18C).

Figure 18B:
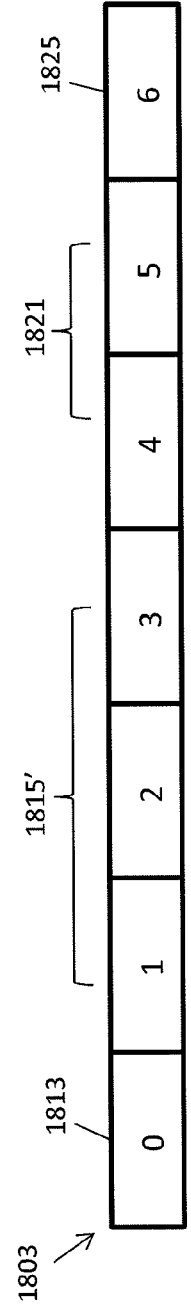
FIG. 18B illustrates one example of a first control signal (e.g., the message payload of the first control signal) that may be sent by a remote controller to a processor of a wearable neurostimulation device in order to prepare the device (e.g., prepare space in the processors memory) to start a new waveform (new component waveform of an ensemble waveform) or modify an existing component waveform. The neurostimulator apparatus may be configured to receive this signal.

FIG. 18B illustrates one example of a message payload portion of a first command message (e.g., a new waveform message 1801) to instruct the wearable neurostimulator to prepare to receive a new set of waveform parameters or a modification of a stored set of waveform parameters. In this example, the controller is configured to transmit, and the processor to receive, a 4 byte message payload that instructs the processor to prepare to either receive a new set of component waveform parameters into a set of memory registers, or to copy and/or modify a stored set of component waveform parameters.

In the message payload for the first command message shown in FIG. 18B, one byte (e.g., byte 0) 1805 indicates what component waveform to expect, e.g., a modification of a currently playing component waveform, a new waveform, or a saved component waveform (e.g., already in a register or set of registers). The new waveform command message payload may also indicate (e.g., byte 1) 1807 a number of segments to expect encoding particular waveform parameters (e.g., when a 'new' waveform will be expected). In this example, the new waveform message payload may also indicate if amplitude modulation is going to be applied (e.g., bytes 3-2) 1809, and may indicate information about the amplitude modulation (e.g., burst frequency, burst duration, etc.), or may indicate if bursting (amplitude modulation) is not to be used.

Figure 18C:
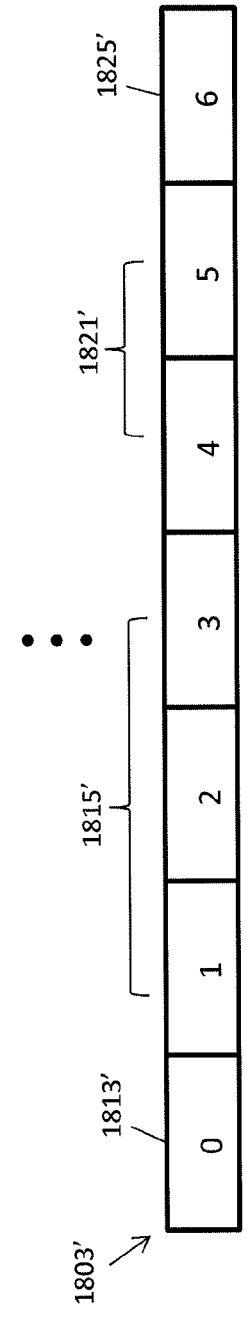
FIG. 18C illustrates one example of a second (and additional, e.g., n) control signal in a series of segments (segment message payloads) encoding information sufficient to allow the neurostimulator to drive the component (and therefore ensemble) waveform signals. A total of n different segment control messages (including message payloads as shown here) may be sent and received as illustrated to efficiently and effectively guide the controller (e.g., a smartphone or other apparatus) in applying effective neurostimulation.

FIG. 18C also illustrates the transmission of one or more (e.g., n) segment command message payloads 1803 from the controller to the processor. In this example, each segment command payload includes the waveform parameters for a component waveform of an ensemble waveform. For example, the segment command message payloads may be (as a non-limiting example) a seven byte message in which the segment command information ("waveform segment message") includes the segment definition information for running a portion of an ensemble waveform (e.g. a component waveform or portion of a component waveform). For example, a message waveform segment may include a segment index (e.g., byte 0) 1813 which corresponds to the sequence of the segment in the waveform when bursting is on (e.g., with amplitude modulation 'on'). The segment may also define the duration of the portion of the waveform (component waveform) being transmitted. For example, bytes one to three 1815 in FIG. 18B may indicate as a 24 bit number the duration in counts of 12 MHz. The segment message may also indicate the current amplitude (peak current amplitude), e.g., in mA as an 8 fraction bit (e.g., in bytes 4 and 5) 1821. Finally, the segment message may include a state indicator (e.g., state byte, shown in FIG. 18B as byte 6), which may include a code indicating what state the applied current for the waveform is, such as positive current, negative current, capacitive discharge, and open circuit (no current delivered). Additional segment messages (segment message payloads 1803') may be transmitted (e.g., a total of n), as shown schematically in FIG. 18B, and may each encode a portion of a component waveform.

Other command messages may include waveform control messages (e.g., commands to start or stop waveforms), and/or to exchange/swap an actual playing waveform with a stored ('shadow') waveform in a memory register.

In general, any of the apparatuses described herein (e.g., within the processor of the neurostimulator) may include firmware and communication protocols for receiving and responding to the command messages. Any of the processors (neurostimulators) described herein may also be configured to transmit error codes back to the controller. For example, the processor may, during communication (e.g., via a communication circuit) check whether received waveform parameters comply with limitations of hardware and safety standards. Examples of error codes that may be safety conditions (e.g., current requested too high, electrode contact lost or poor connection, DC limit reached, communication lost), error codes related to the received command messages/communication (e.g., too many wave segments, fewer segments received than expected, received segments too short, received segments too long, etc.)

Any of the apparatuses for neurostimulation described herein may be configured to receive a plurality of neurostimulation command messages, including in particular the new waveform message and subsequent segment messages, which may include parameters from a controller such as a computing device (e.g., smartphone, etc.) and apply them as stimulation. The neurostimulator may also adjust them and/or send one or more response error messages back to the controller if the parameters contained in the messages do not comply with hardware limitations and/or safety limits which may be included in the neurostimulator.

FIGS. 18A-18C described above illustrate one possible framework for transmitting waveforms parameters and/or instructions (e.g., as 400 ms segments). This framework, including the specific segment definitions included herein provide a robust way to send waveform parameters in small and manageable pieces that allow very quick response between the controller and the neurostimulator (allowing the system to nearly-immediately respond to user modifications, stops or changes in the applied waveforms), while transmitting a minimum of required information.

In use, the system may be configured so that the controller (e.g., a control apparatus) controls the wearable neurostimulator by transmitting a first message (e.g., new waveform message) from the control apparatus instructing the wearable neurostimulator to prepare to receive a new set of waveform parameters or a modification of a stored set of waveform parameters. The controller may then transmit one (or more likely, more than one) segment messages from the control apparatus, where each segment message defining a segment of the new waveform parameters or the modification to the stored waveform parameters. The segment messages may each comprise a message encoding: a segment index number, a segment duration, a current amplitude, and a state code, wherein the state code indicates one of: positive current, negative current, capacitive discharge, and open circuit.

In general, the segments may correspond to sub-regions of the ensemble waveform that have a particular value (e.g. positive-going current, negative-going current, capacitive discharge current, no current), and segments may be sequentially stitched together to form a single unit pulse, then repeated to form the component waveform of an ensemble waveform.

In general, the hardware of a controller (waveform controller) may be a dedicated device or it may be an apparatus, such as a smartphone, etc. that can be configured to wirelessly transmit the control information as described above. Although wireless configurations are described above, FIG. 17B also provides an example of an integrated or hardwired connection between a controller 1705' and a processor 1707', in which the two components are attached to the same apparatus 1701', such as a single-use neurostimulator which may be formed, e.g., as a device in which the processor and controller are physically connected (e.g., by a wire or trace) rather than wirelessly connected.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of controlling a wearable neurostimulator from a control apparatus, the method comprising:
   transmitting a first message from the control apparatus instructing the wearable neurostimulator to prepare to receive a new set of waveform parameters or a modification of a stored set of waveform parameters; and
   transmitting one or more segment messages from the control apparatus, the segment messages defining segments of the new waveform parameters or the modification to the stored waveform parameters, the segment messages each comprising a message encoding: a segment index number, a segment duration, a current amplitude, and a state code, wherein the state code indicates one of: positive current, negative current, capacitive discharge, and open circuit.

2. The method of claim 1, wherein the first message comprises a message identification code identifying the first message as containing instructions instructing the wearable neurostimulator to prepare to receive the new set of waveform parameters or the modification of the stored waveform parameters.

3. The method of claim 1, wherein the one or more segment messages comprise a message identification code identifying them as segment messages.

4. The method of claim 1, wherein transmitting the first message comprises transmitting the first message comprising a four byte message payload.

5. The method of claim 1, wherein the segment messages each comprise a seven byte message payload.

6. The method of claim 1, wherein transmitting the first message and the one or more segment messages comprise wirelessly transmitting from the control apparatus to the wearable neurostimulator.

7. The method of claim 1, wherein transmitting from the first message and the one or more segment messages comprise transmitting through a physical connection between the control apparatus and the wearable neurostimulator.

8. The method of claim 1, further comprising pairing or synchronizing the wearable neurostimulator and the remote control apparatus.

9. The method of claim 1, wherein the first message includes: a code indicating transmission of a new waveform or transmission of a modification of a stored waveform, a number of segments to expect, and an indication that the waveform will be burst modulated.

10. The method of claim 1, wherein the control apparatus transmits the first message and/or the one or more segment messages about every 400 milliseconds.

11. The method of claim 1, wherein the control apparatus transmits the first message and the one or more segment messages by Bluetooth.

12. A method of controlling a wearable neurostimulator from a control apparatus, the method comprising:
transmitting a first message from the control apparatus instructing the wearable neurostimulator to prepare to receive a new set of waveform parameters or a modification of a stored set of waveform parameters, the first message comprising a four byte message payload, wherein the first message includes: a code indicating transmission of a new waveform or transmission of a modification of a stored waveform, a number of segments to expect, and an indication that the waveform will be burst modulated; and
transmitting one or more segment messages from the control apparatus, the segment messages defining segments of the new waveform parameters or the modification to the stored waveform parameters, the segment messages each comprising a seven byte message payload encoding: a segment index number, a segment duration, a current amplitude, and a state code, wherein the state code indicates one of: positive current, negative current, capacitive discharge, and open circuit.

13. The method of claim 11, wherein the first message comprises a message identification code identifying the first message as containing instructions instructing the wearable neurostimulator to prepare to receive the new set of waveform parameters or the modification of the stored waveform parameters.

14. The method of claim 11, wherein the one or more segment messages comprise a message identification code identifying them as segment messages.

15. The method of claim 11, wherein transmitting the first message and the one or more segment messages comprise wirelessly transmitting from the control apparatus to the wearable neurostimulator.

16. The method of claim 11, further comprising pairing or synchronizing the wearable neurostimulator and the control apparatus.

17. The method of claim 11, wherein transmitting from the first message and the one or more segment messages comprise transmitting through a physical connection between the control apparatus and the wearable neurostimulator.

18. The method of claim 11, wherein transmitting the first message and the one or more segment messages comprise wirelessly transmitting from the control apparatus to the wearable neurostimulator.

19. The method of claim 11, wherein the control apparatus transmits the first message and/or the one or more segment messages about every 400 msec or multiples of 400 msec.

20. The method of claim 11, wherein the control apparatus transmits the first message and the one or more segment messages by Bluetooth.

21. A control apparatus for controlling a wearable neurostimulator, the apparatus comprising:
a processor, the processor configured to:
transmit a first message instructing the wearable neurostimulator to prepare to receive a new set of waveform parameters or a modification of a stored set of waveform parameters, the first message comprising: a code indicating transmission of a new waveform or transmission of a modification of a stored waveform, a number of segments to expect, and an indication that the waveform will be burst modulated; and
transmit one or more segment messages from the control apparatus, the segment messages defining segments of the new waveform parameters or the modification to the stored waveform parameters, the segment messages each encoding: a segment index number, a segment duration, a current amplitude, and a state code, wherein the state code indicates one of: positive current, negative current, capacitive discharge, and open circuit.

22. The apparatus of claim 21, wherein the processor is configured to transmit the first message as a 20 byte or smaller message including a four byte message payload.

23. The apparatus of claim 21, wherein the processor is configured to transmit the one or more segment messages as a 20 byte or smaller messages that include a seven byte message payload.

24. The apparatus of claim 21, wherein the processor is configured to transmit the first message to include a message identification code identifying the first message as containing instructions instructing the wearable neurostimulator to prepare to receive the new set of waveform parameters or the modification of the stored waveform parameters.

25. The apparatus of claim 21, wherein the processor is configured to transmit the one or more segment messages to each include a message identification code identifying them as segment messages.

26. The apparatus of claim 21, wherein the processor is configured to wirelessly transmit the first message and the one or more segment messages.

27. The apparatus of claim 21, wherein the processor is connected via a physical connection to the wearable neurostimulator, and/or is integrated into the wearable neurostimulator, so that the processor transmits the first message and the one or more segment messages through the physical connection between the control apparatus and the wearable neurostimulator.

28. The apparatus of claim 21, wherein the processor is configured to wirelessly transmit the first message and the one or more segment messages from the control apparatus.

29. The apparatus of claim 21, wherein the control apparatus is configured to transmit the first message and/or the one or more segment messages about every 400 msec or multiples of 400 msec.

* * * * *